US012163921B2

United States Patent
Braganca et al.

(10) Patent No.: US 12,163,921 B2
(45) Date of Patent: Dec. 10, 2024

(54) BASED ON THERMAL STABILITIES OF MAGNETIC NANOPARTICLES

(71) Applicant: Western Digital Technologies, Inc., San Jose, CA (US)

(72) Inventors: Patrick Braganca, San Jose, CA (US); Daniel Bedau, San Jose, CA (US)

(73) Assignee: Western Digital Technologies, Inc., San Jose, CA (US)

( * ) Notice: Subject to any disclaimer, the term of this patent is extended or adjusted under 35 U.S.C. 154(b) by 0 days.

(21) Appl. No.: 18/165,089

(22) Filed: Feb. 6, 2023

(65) Prior Publication Data
US 2023/0184716 A1 Jun. 15, 2023

Related U.S. Application Data

(62) Division of application No. 16/727,064, filed on Dec. 26, 2019, now Pat. No. 11,609,208.

(60) Provisional application No. 62/833,206, filed on Apr. 12, 2019.

(51) Int. Cl.
*G01N 27/74* (2006.01)
*B01L 3/00* (2006.01)
*B01L 7/00* (2006.01)
*C12Q 1/6874* (2018.01)

(52) U.S. Cl.
CPC ...... *G01N 27/745* (2013.01); *B01L 3/502715* (2013.01); *B01L 7/52* (2013.01); *C12Q 1/6874* (2013.01); *B01L 2200/0647* (2013.01); *B01L 2300/0627* (2013.01); *B01L 2300/0809* (2013.01); *B01L 2300/1805* (2013.01)

(58) Field of Classification Search
None
See application file for complete search history.

(56) References Cited

U.S. PATENT DOCUMENTS

| | | |
|---|---|---|
| 5,200,084 A | 4/1993 | Liberti et al. |
| 5,302,509 A | 4/1994 | Cheeseman |
| 6,037,167 A | 3/2000 | Adelman et al. |
| 6,046,585 A | 4/2000 | Simmonds |
| 6,197,520 B1 | 3/2001 | Wittwer et al. |
| 6,406,848 B1 | 6/2002 | Bridgham et al. |
| 6,654,505 B2 | 11/2003 | Bridgham et al. |
| 6,806,052 B2 | 10/2004 | Bridgham et al. |
| 6,831,994 B2 | 12/2004 | Bridgham et al. |
| 6,833,246 B2 | 12/2004 | Balasubramanian |
| 6,905,736 B1 | 6/2005 | Chow et al. |
| 6,969,488 B2 | 11/2005 | Bridgham et al. |
| 6,969,679 B2 | 11/2005 | Okamura et al. |
| 7,057,026 B2 | 6/2006 | Barnes et al. |
| 7,115,400 B1 | 10/2006 | Adessi et al. |
| 7,282,370 B2 | 10/2007 | Bridgham et al. |
| 7,382,586 B2 | 6/2008 | Carey et al. |
| 7,405,281 B2 | 7/2008 | Xu et al. |
| 7,414,116 B2 | 8/2008 | Milton et al. |
| 7,427,673 B2 | 9/2008 | Balasubramanian et al. |
| 7,473,031 B2 | 1/2009 | Wolkin et al. |
| 7,541,444 B2 | 6/2009 | Milton et al. |
| 7,566,537 B2 | 7/2009 | Balasubramanian et al. |
| 7,771,973 B2 | 8/2010 | Milton et al. |
| 7,772,384 B2 | 8/2010 | Balasubramanian et al. |
| 7,920,032 B2 | 4/2011 | Makinwa et al. |
| 8,053,244 B2 | 11/2011 | Ryan et al. |
| 8,058,031 B2 | 11/2011 | Xu et al. |
| 8,071,739 B2 | 12/2011 | Milton et al. |
| 8,130,072 B2 | 3/2012 | De Bruyker et al. |
| 8,158,346 B2 | 4/2012 | Balasubramanian et al. |
| 8,252,910 B2 | 8/2012 | Korlach et al. |
| 8,259,409 B2 | 9/2012 | Braganca et al. |
| 8,361,713 B2 | 1/2013 | Bridgham et al. |
| 8,367,813 B2 | 2/2013 | Korlach |
| 8,432,644 B2 | 4/2013 | Braganca et al. |
| 8,462,461 B2 | 6/2013 | Braganca et al. |
| 8,513,029 B2 | 8/2013 | Zhou |
| 8,553,346 B2 | 10/2013 | Braganca et al. |
| 8,570,677 B2 | 10/2013 | Braganca et al. |
| 8,597,881 B2 | 12/2013 | Milton et al. |
| 8,652,810 B2 | 2/2014 | Adessi et al. |
| 8,654,465 B2 | 2/2014 | Braganca et al. |

(Continued)

FOREIGN PATENT DOCUMENTS

| | | |
|---|---|---|
| CN | 1605031 A | 4/2005 |
| CN | 1608206 A | 4/2005 |

(Continued)

OTHER PUBLICATIONS

R. Sato, K. Kudo, T. Nagasawa, H. Suto, and K. Mizushima, "Simulations and Experiments Toward High-Data-Transfer-Rate Readers Composed of a Spin-Torque Oscillator," IEEE Transactions on Magnetics, vol. 48, 1758, 2012.
Rabehi, A., Electromagnetic microsystem for the detection of magnetic nanoparticles in a microfluidic structure for Immunoassays (Doctoral dissertation). Jan. 29, 2020.
Rauwerdink, A. M., Giustini, A. J., & Weaver, J. B. (2010). Simultaneous quantification of multiple magnetic nanoparticles. Nanotechnology, 21(45), 455101.
Riedinger, A., Guardia, P., Curcio, A., Garcia, M. A., Cingolani, R., Manna, L., & Pellegrino, T. (2013). Subnanometer local temperature probing and remotely controlled drug release based on azo-functionalized iron oxide nanoparticles. Nano letters, 13(6), 2399-2406.

(Continued)

*Primary Examiner* — Katherine D Salmon

(57) ABSTRACT

Disclosed herein are detection methods that use magnetic nanoparticles (MNPs) to allow molecules to be identified. Embodiments of this disclosure include methods of using magnetic sensors (e.g., magnetoresistive sensors) to detect temperature-dependent magnetic fields (or changes in magnetic fields) emitted by MNPs, and, specifically to distinguish between the presence and absence of magnetic fields emitted, or not emitted, by MNPs at different temperatures selected to take advantage of knowledge of how the MNPs' magnetic properties change with temperature. Embodiments disclosed herein may be used for nucleic acid sequencing, such as deoxyribonucleic acid (DNA) sequencing.

26 Claims, 20 Drawing Sheets

(56) References Cited

U.S. PATENT DOCUMENTS

| | | |
|---|---|---|
| 8,675,309 B2 | 3/2014 | Braganca et al. |
| 8,728,729 B2 | 5/2014 | Bridgham et al. |
| 8,728,825 B2 | 5/2014 | Wang et al. |
| 9,121,062 B2 | 9/2015 | Balasubramanian et al. |
| 9,273,354 B2 | 3/2016 | Bridgham et al. |
| 9,297,006 B2 | 3/2016 | Adessi et al. |
| 9,435,791 B2 | 9/2016 | Acosta et al. |
| 9,453,258 B2 | 9/2016 | Kain et al. |
| 9,464,107 B2 | 10/2016 | Wegener et al. |
| 9,587,275 B2 | 3/2017 | Emig et al. |
| 9,605,310 B2 | 3/2017 | Balasubramanian et al. |
| 9,640,748 B2 | 5/2017 | Gotsmann et al. |
| 10,203,379 B2 | 2/2019 | Wang et al. |
| 10,260,095 B2 | 4/2019 | Esfandyarpour et al. |
| 10,591,440 B2 | 3/2020 | Astier et al. |
| 2003/0008308 A1 | 1/2003 | Enzelberger et al. |
| 2004/0043479 A1 | 3/2004 | Briscoe et al. |
| 2004/0219695 A1 | 11/2004 | Fox |
| 2005/0054081 A1 | 3/2005 | Hassard et al. |
| 2005/0100930 A1 | 5/2005 | Wang et al. |
| 2005/0118102 A1 | 6/2005 | Xiang et al. |
| 2007/0114180 A1 | 5/2007 | Ramanathan et al. |
| 2007/0218567 A1 | 9/2007 | Tanaka et al. |
| 2007/0224700 A1 | 9/2007 | Masters |
| 2007/0264159 A1 | 11/2007 | Graham et al. |
| 2008/0218165 A1 | 9/2008 | Kahlman et al. |
| 2008/0221432 A1 | 9/2008 | Zhou |
| 2008/0241569 A1 | 10/2008 | Qin et al. |
| 2009/0148857 A1 | 6/2009 | Srivastava et al. |
| 2009/0206832 A1 | 8/2009 | Kahlman et al. |
| 2009/0208957 A1 | 8/2009 | Korlach et al. |
| 2010/0039105 A1 | 2/2010 | Ryan et al. |
| 2010/0111768 A1 | 5/2010 | Banerjee et al. |
| 2010/0194386 A1 | 8/2010 | Prins et al. |
| 2010/0207631 A1 | 8/2010 | McDowell |
| 2010/0231214 A1 | 9/2010 | Zhou |
| 2010/0248973 A1 | 9/2010 | Lankvelt et al. |
| 2010/0291558 A1 | 11/2010 | Kim |
| 2011/0223612 A1 | 9/2011 | Wang et al. |
| 2012/0214171 A1 | 8/2012 | Kotseroglou |
| 2012/0295262 A1 | 11/2012 | Ronaghi et al. |
| 2014/0008281 A1 | 1/2014 | Ramanathan et al. |
| 2014/0099663 A1 | 4/2014 | Wang et al. |
| 2014/0139214 A1 | 5/2014 | Park et al. |
| 2014/0292318 A1 | 10/2014 | Wang et al. |
| 2016/0131613 A1 | 5/2016 | Jayant et al. |
| 2017/0097337 A1 | 4/2017 | Shultz et al. |
| 2017/0191852 A1 | 7/2017 | Foletto et al. |
| 2017/0304825 A1 | 10/2017 | Issadore et al. |
| 2018/0074016 A1 | 3/2018 | Chen et al. |
| 2018/0100190 A1 | 4/2018 | Esfandyarpour et al. |
| 2018/0128822 A1 | 5/2018 | Wang et al. |
| 2018/0237850 A1 | 8/2018 | Mandell et al. |
| 2018/0284200 A1 | 10/2018 | Chen et al. |
| 2019/0032114 A1 | 1/2019 | Trivedi |
| 2019/0170680 A1 | 6/2019 | Sikora et al. |
| 2019/0390267 A1 | 12/2019 | Astier et al. |
| 2021/0047681 A1 | 2/2021 | Mendonsa et al. |
| 2021/0047682 A1 | 2/2021 | Mendonsa et al. |

FOREIGN PATENT DOCUMENTS

| | | |
|---|---|---|
| CN | 101375424 A | 2/2009 |
| CN | 102246034 A | 11/2011 |
| CN | 102928596 A | 2/2013 |
| CN | 103885000 A | 6/2014 |
| CN | 103892809 A | 7/2014 |
| CN | 104644138 A | 5/2015 |
| CN | 105112516 A | 12/2015 |
| CN | 106137519 A | 11/2016 |
| CN | 107873060 A | 4/2018 |
| CN | 107923910 A | 4/2018 |
| CN | 108138229 A | 6/2018 |
| CN | 107051597 B | 8/2019 |
| EP | 1544310 A2 | 6/2005 |
| EP | 2674264 A2 | 12/2013 |
| EP | 3208627 A1 | 8/2017 |
| ES | 2674264 | 6/2018 |
| WO | 2005047864 A3 | 9/2005 |
| WO | 2005124345 A3 | 4/2006 |
| WO | 2015031691 A1 | 3/2015 |
| WO | 2016183218 A1 | 11/2016 |
| WO | 2017030999 A1 | 2/2017 |
| WO | 2017061129 A1 | 4/2017 |
| WO | 2017140877 A1 | 8/2017 |
| WO | 2018017884 A1 | 1/2018 |
| WO | 2018186539 A1 | 10/2018 |
| WO | 2018226876 A1 | 12/2018 |
| WO | 2019060628 A1 | 3/2019 |
| WO | 2019068204 A1 | 4/2019 |
| WO | 2020210370 A1 | 10/2020 |

OTHER PUBLICATIONS

S. Dutz and R. Hergt, "Magnetic nanoparticle heating and heat transfer on a microscale: Basic principles, realities and physical limitations of hyperthermia for tumour therapy," Int J Hyperthermia, 2013; 29(8): 790-800.

S.I. Kiselev et al., "Microwave oscillations of a nanomagnet driven by a spin-polarized current," Nature 425, pp. 380-383, 2003.

Srimani T. et al., "High Sensitivity Biosensor using Injection Locked Spin Torque Nano-Oscillators," arXiv: 1511.09072, Nov. 2015.

T. Nagasawa et al., "Delay detection of frequency modulation signal from a spin-torque oscillator under a nanosecond-pulsed magnetic field," Journal of Applied Physics, vol. 111, 07C908 (2012).

Tang, C., He, Z., Liu, H., Xu, Y., Huang, H., Yang, G., . . . & Chen, Z. (2020). Application of magnetic nanoparticles in nucleic acid detection. Journal of Nanobiotechnology, 18, 1-19. Apr. 21, 2020.

W. Andrä et al., "Temperature distribution as function of time around a small spherical heat source of local magnetic hyperthermia," Journal of Magnetism and Magnetic Materials, vol. 194, Issues 1-3, Apr. 1999, pp. 197-203.

Wang, W., & Jiang, Z., "Thermally assisted magnetic tunneling junction for biosensing applications," IEEE Transactions on Magnetics, 43(6), 2406-2408, Jun. 30, 2007.

Weifeng Shen et al., "Detection of DNA labeled with magnetic nanoparticles using MgO-based magnetic tunnel junction sensors," Journal of Applied Physics 103, 07A306 (2008).

Weijun Zhou, et al., "Novel dual fluorescence temperature-sensitive chameleon DNA-templated nanocluster pair for Intracellular thermometry" Nano Research (2018), vol. 11, pp. 2012-2023, Mar. 19, 2018, https://doi.org/10.1007/s12274-017-1817-7 Mar. 19, 2018 (Mar. 19, 2018).

Xia, Haiyan et al., "Micromagnetic simulation for detection of magnetic nanobeads by spin torque oscillator," Journal of Magnetism and Magnetic Materials 2017, vol. 432, pp. 387-390, Feb. 4, 2017.

Y.-C. Liang, L. Chang, W. Qiu, A. G. Kolhatkar, B. Vu, K. Kourentzi, T. R. Lee, Y. Zu, R. Willson, and D. Litvinov, "Ultrasensitive Magnetic Nanoparticle Detector for Biosensor Applications," Sensors, vol. 17, 1296, 2017.

Ye, F., Zhao, Y., El-Sayed, R., Muhammed, M., & Hassan, M. (2018). Advances in nanotechnology for cancer biomarkers. Nano Today, 18, 103-123.

Yu, L., Liu, J., Wu, K., Klein, T., Jiang, Y., & Wang, J. P. (2014). Evaluation of hyperthermia of magnetic nanoparticles by dehydrating DNA. Scientific reports, 4, 7216.

U.S. Appl. No. 62/833,130, filed Apr. 12, 2019, Yann Astier.

A. Seki, et al., "Study of the heating characteristics and mechanisms of magnetic nanoparticles over a wide range of frequencies and amplitudes of an alternating magnetic field," Journal of Physics: Conference Series 521 (2014).

A.M. Sydor et al., "Super-Resolution Microscopy: From Single Molecules to Supramolecular Assemblies," Trends in Cell Biology, Dec. 2015, vol. 25, No. 12, pp. 730-748.

(56) References Cited

OTHER PUBLICATIONS

B. N. Engel, et al., "A 4-Mb Toggle MRAM Based on a Novel Bit and Switching Method," IEEE Transactions on Magnetics, vol. 41, No. 1, Jan. 2005.
C. Chappert et al., "The emergence of spin electronics in data storage," Nature Materials, Dec. 2007.
C.H. Smith et al., "High-resolution giant magnetoresistance on-chip arrays for magnetic imaging," Journal of Applied Physics 93, 6864 (2003).
D. Ross et al., "Temperature Measurement in Microfluidic Systems Using a Temperature-Dependent Fluorescent Dye," Anal. Chem. 2001, 73, 17, 4117-4123, Jul. 24, 2001.
Daschiel et al. The holy grail of microfluidics: sub-laminar drag by layout of periodically embedded microgrooves (2013) MicrofluidNanofluid 15, 675-687.
E. du Trémolet de Lacheisserie, D. Gignoux, and M. Schlenker (editors), Magnetism: Materials and Applications, vol. 2. Springer, 2005.
E. Hall, "On a New Action of the Magnet on Electric Currents," American Journal of Mathematics, vol. 2, 287, 1879.
ePHOTOzine.com, "Complete Guide to Image Sensor Pixel Size," Aug. 2, 2016, available at https://www.ephotozine.com/article/complete-guide-to-image-sensor-pixel-size-29652.
F. Grasset et al., "Synthesis, magnetic properties, surface modification and cytotoxicity evaluation of Y3Fe5-xAlxO12 (0?x?2) garnet submicron particles for biomedical applications," Journal of Magnetism and Magnetic Materials, vol. 234, Issue 3, Sep. 2001, pp. 409-418.
F. Menges et al., "Temperature mapping of operating nanoscale devices by scanning probe thermometry," Nature Communications, 7:10874, Mar. 3, 2016.
G. Li, S. Sun, R. J. Wilson, R. L. White, N. Pourmand, S. X. Wang, "Spin valve sensors for ultrasensitive detection of superparamagnetic nanoparticles for biological applications," Sensors and Actuators, vol. 126, 98, 2006.
Illumina, "Illumina CMOS Chip and One-Channel SBS Chemistry," document No. 770-2013-054-B, 2018 (available at https://www.illumina.com/content/dam/illumina-marketing/documents/products/techspotlights/cmos-tech-note-770-2013-054.pdf).
Illumina, "NovaSeq 6000 Sequencing System," 2019, available at https://www.illumina.com/systems/sequencing-platforms/novaseq.html.
International Search Report and Written Opinion from PCT Application No. PCT/US2019/068131 (filed Dec. 20, 2019), mailed Apr. 1, 2020.
International Search Report and Written Opinion from PCT Application No. PCT/US2019/068535 (filed Dec. 26, 2019), mailed Apr. 26, 2020.
International Search Report and Written Opinion from PCT Application No. PCT/US2020/014707 (filed Jan. 23, 2020), mailed May 11, 2020.
International Search Report and Written Opinion from PCT Application No. PCT/US2020/021776 (filed Mar. 9, 2020), mailed Sep. 1, 2020.
International Search Report and Written Opinion from PCT Application No. PCT/US2020/023069 (filed Mar. 17, 2020), mailed Jul. 20, 2020.
International Search Report and Written Opinion from PCT Application No. PCT/US2020/023078 (filed Mar. 17, 2020), mailed Jul. 19, 2020.
International Search Report and Written Opinion from PCT Application No. PCT/US2020/027290 (filed Apr. 8, 2020), mailed Jun. 25, 2020.
International Search Report and Written Opinion from PCT Application No. PCT/US2020/035915 (filed Jun. 3, 2020), mailed Aug. 26, 2020.
International Search Report and Written Opinion from PCT Application No. PCT/US2021/021274 (filed Mar. 7, 2021), mailed Sep. 28, 2021.
International Search Report and Written Opinion from PCT Application No. PCT/US2021/028263 (filed Apr. 21, 2021), mailed Aug. 26, 2021.
International Search Report and Written Opinion from PCT Application No. PCT/US2021/040767 (filed Jul. 8, 2021), mailed Oct. 25, 2021.
International Search Report from PCT App. No. PCT/US2016/046888, mailed Oct. 26, 2016.
J. C. Slonczewski, "Current-driven excitation of magnetic multilayers," Journal of Magnetism and Magnetic Materials, vol. 159, L1, 1996.
J. Sakakibara et al., "Measurements of thermally stratified pipe flow using image-processing techniques," Experiments in Fluids, Dec. 1993, vol. 16, Issue 2, pp. 82-96.
John PEARCE, et al., "Magnetic Heating of Nanoparticles: The Importance of Particle Clustering to Achieve Therapeutic Temperatures," Journal of Nanotechnology in Engineering and Medicine, Feb. 2014, vol. 4 / 011007-1.
L. Berger, "Emission of spin waves by a magnetic multilayer traversed by a current," Physical Review B, vol. 54, 9353, 1996.
Lany, M., G. Boero, and R. S. Popovic. "Superparamagnetic microbead inductive detector". Review of scientific Instruments 76.8 (2005): 084301.
Latha, G., Kumar, P. D., Gopi, K., Srikanth, P., Kusumalatha, Y., & Babu, G. V. (2017). A review on magnetic micro/nanoparticles. World J. Pharm. Res, 6, 341-366.
Lin Gui and Carolyn L. Ren, "Temperature measurement in microfluidic chips using photobleaching of a fluorescent thin film," Applied Physics Letters 92, 024102, 2008.
M. Aslam et al., "Silica encapsulation and magnetic properties of FePt nanoparticles," Journal of Colloid and Interface Science 290 (2005) 444-449.
M. Diaz-Michelena, "Small Magnetic Sensors for Space Applications," Sensors, vol. 9, 2271, 2009.
M. Hisham Alnasir et al., "Magnetic and magnetothermal studies of pure and doped gadolinium silicide nanoparticles for self-controlled hyperthermia applications," Journal of Magnetism and Magnetic Materials, vol. 449, Mar. 1, 2018, pp. 137-144.
M.T. Tlili et al., "Magnetic, Electrical Properties and Spin-Glass Effect of Substitution of Ca for Pr in Ca2-xPrxMnO4 Compounds," The Open Surface Science Journal, 2009, vol. 1, pp. 54-58.
Mao et al. A Microfluidic Device with a Linear Temperature Gradient for Parallel and Combinatorial Measurements (2002) J AmChem Soc 124, 4432-4435.
Michael L. Metzker, "Sequencing Technologies—the Next Generation," Nature Rev. Genet. 11: 31-46 (2009).
Miller, M. M., et al. "A DNA array sensor utilizing magnetic microbeads and magnetoelectronic detection". Journal of Magnetism and Magnetic Materials 225.1-2 (2001): 138-144.
N. X. Phuc, et al., "Tuning of the Curie Temperature in La1-xSrxMn1-yTiyO3" J. Korean Phy. Soc., vol. 52, No. 5, May 2008, pp. 1492-1495.
N.R. Patil et al., "Effect of temperature on the fluorescence emission of ENCTTTC in different nonpolar solvents," Can. J. Phys. 91: 971-975 (2013).
P. Anderson, J. Rowell, "Probable Observation of the Josephson Superconducting Tunneling Effect," Physical Review Letters, vol. 10, 230, 1963.
P. M. Braganca, B. A. Gurney, B. A. Wilson, J. A. Katine, S. Maat and J. R. Childress, "Nanoscale magnetic field detection using a spin torque oscillator," Nanotechnology, vol. 21, 235202, 2010.
P. Namdari, H. Daraee, and A. Eatemadi, "Recent Advances in Silicon Nanowire Biosensors: Synthesis Methods, Properties and Applications", Nanoscale Research Letters, vol. 11, 406, 2016.
Qiu et al. Instrument-free point-of-care molecular diagnosis of H 1 N 1 based on microfluidic convective PCR (2017) Sensors andActuators B: Chemical 243, 738-744.
Quynh, L. K., et al. Detection of magnetic nanoparticles using simple AMR sensors in Wheatstone bridge. Journal of Science: Advanced Materials and Devices, 2016, 1.1: 98-102.
R. C. Jaklevic, J. Lambe, A. H. Silver & J. E. Mercereau, "Quantum Interference Effects in Josephson Tunneling," Physical Review Letters, vol. 12, 159, 1964.

(56) References Cited

OTHER PUBLICATIONS

R. Giri, "Temperature effect study upon the fluorescence emission of substituted coumarins," Spectrochimica Acta Part A: Molecular Spectroscopy, vol. 48, Issue 6, Jun. 1992, p. 843-848.

Zhi-Dong, P., et al., "Study on Thermal Conductivity of Magnetic Nanofluid in Magnetic Field", School of Materials Science and Engineering, Issue 11, vol. 44, pp. 1554-1557 (2013).

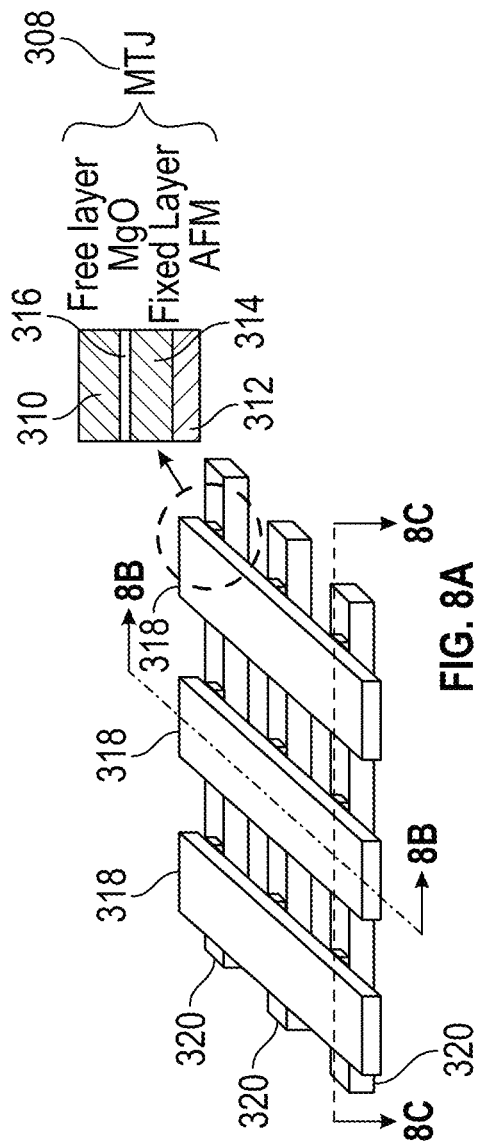
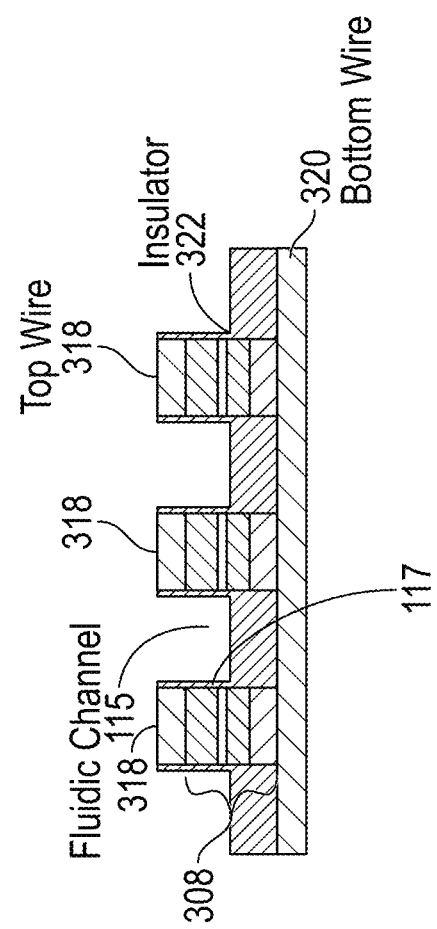
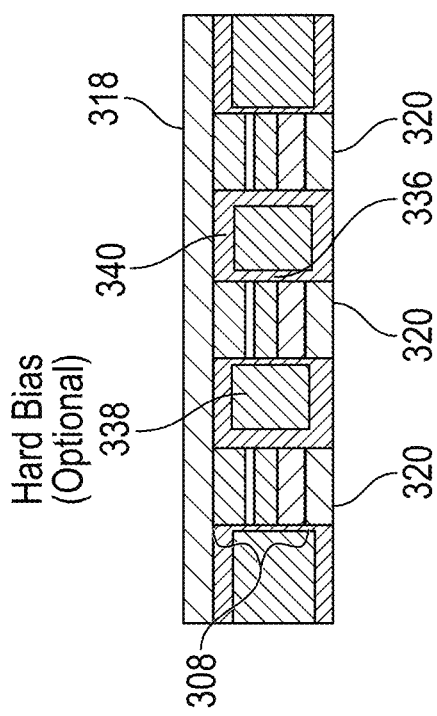
FIG. 8A
FIG. 8B
FIG. 8C

BASED ON THERMAL STABILITIES OF MAGNETIC NANOPARTICLES

CROSS-REFERENCE TO RELATED APPLICATIONS

This application is a divisional of U.S. patent application Ser. No. 16/727,064, filed Dec. 26, 2019 and entitled "DEVICES AND METHODS FOR MOLECULE DETECTION BASED ON THERMAL STABILITIES OF MAGNETIC NANOPARTICLES", which claims the benefit of U.S. Provisional Application No. 62/833,206, filed Apr. 12, 2019 and entitled "MAGNETORESISTIVE SENSOR ELEMENTS FOR NUCLEIC ACID SEQUENCING ARRAYS AND DETECTION SCHEMES FOR NUCLEIC ACID SEQUENCING USING MAGNETIC NANOPARTICLES WITH DIFFERENT THERMAL STABILITY." Both of the above-referenced applications are hereby incorporated by reference in their entireties for all purposes.

BACKGROUND

Field of the Disclosure

Embodiments of the present disclosure generally relate to devices and methods for using a magnetoresistive (MR) sensor array for molecule detection, such as for nucleic acid sequencing (e.g., deoxyribonucleic acid (DNA) sequencing).

Description of the Related Art

Current state-of-the-art sequencing systems are based on fluorescence signal detection and provide throughputs of 20 billion reads per run (www.illumina.com/systems/sequencing-platforms/novaseq.html). Achieving such performance, however, can require large-area flow cells, high-precision free-space imaging optics, and expensive high-power lasers to generate sufficient fluorescence signals for successful base detection.

One type of nucleic acid sequencing used for DNA sequencing is known as "sequencing by synthesis" (SBS). SBS involves binding of primer-hybridized template DNA, incorporation of a deoxynucleoside triphosphate (dNTP), and detection of incorporated dNTP. Gradual increases in SBS throughput have been accomplished in two ways, the first being an outward scaling, where the size and the number of flow cells in the sequencers is increased. This approach increases both the cost of reagents and the price of the sequencing system, as more high-power lasers and high-precision nano-positioners must be employed. The second approach involves inward scaling, where the density of DNA testing sites is increased so that the total number of sequenced DNA strands in a fixed-size flow cell is higher. To accomplish inward scaling, increasingly higher numerical aperture (NA) lenses must be employed to distinguish the signal from neighboring fluorophores as the spacing between them decreases. However, this approach cannot be implemented indefinitely, as the Rayleigh criterion puts the distance between resolvable light point sources at $0.61\lambda/NA$, constraining the minimum distance between two sequenced DNA strands to be no smaller than approximately 400 nm. Similar resolution limits apply to sequencing directly on top of imaging arrays (similar to cell phone cameras), where the smallest pixel size achieved so far is approximately 1 µm (www.ephotozine.com/article/complete-guide-to-image-sensor-pixel-size-29652).

The Rayleigh criterion currently represents the fundamental limitation for inward scaling of optical SBS systems, which can only be overcome by applying super-resolution imaging techniques (see A. M. Sydor, K. J. Czymmek, E. M. Puchner, and V. Mannella, "Super-Resolution Microscopy: From Single Molecules to Supramolecular Assemblies," Special Issue: Quantitative Cell Biology, Vol. 25, 730, 2015) and has not yet been achieved in highly multiplexed systems. Hence, increasing throughput and decreasing cost of optical SBS sequencers has been slow due to the need to build bigger flow cells and implement more expensive optical scanning and imaging systems.

Therefore, there is a need for new and improved apparatuses for and methods of detecting the presence of molecules such as nucleic acids that overcome the limitations of conventional apparatuses and methods.

SUMMARY

This summary represents non-limiting embodiments of the disclosure.

Disclosed herein are detection devices, systems, and methods that use magnetic nanoparticles (MNPs) to allow molecules labeled by MNPs to be detected. Embodiments of this disclosure are directed to various detection device and system embodiments using magnetic sensors capable of providing outputs indicating the presence or absence of MNPs near the magnetic sensors, and detection method embodiments designed to determine (e.g., measure or obtain) magnetic sensor outputs (e.g., a resistance, a voltage, a current, a frequency, a noise, or a change in resistance, voltage, current, frequency, or noise) indicative of the presence of MNPs. Embodiments of the present disclosure generally relate to devices and methods for using a magnetoresistive (MR) sensor array to detect molecules. Embodiments disclosed herein may be used for nucleic acid sequencing, such as deoxyribonucleic acid (DNA) sequencing.

In some embodiments, a method of detecting molecules using a sequencing device comprising at least one fluidic channel and a plurality of magnetic sensors configured to detect MNPs within the fluidic channel comprises, in one or more rounds of addition, adding, to the at least one fluidic channel, first and second pluralities of molecules to be detected. At least some of the first plurality of molecules to be detected have been labeled by a first type of MNP, wherein, in a first temperature range, a magnitude of a magnetic field generated by the first type of MNP is greater than or equal to a first threshold, and, in a second temperature range, the magnitude of magnetic field generated by the first type of MNP is less than the first threshold, wherein the first temperature range is lower than the second temperature range. At least some of the second plurality of molecules to be detected have been labeled by a second type of MNP, wherein, in the first and second temperature ranges, a magnitude of a magnetic field generated by the second type of MNP is greater than or equal to a second threshold, which may be the same as or different from the first threshold. The method further comprises setting a temperature within the fluidic channel to be within the first temperature range, and obtaining an output from a selected one of the plurality of magnetic sensors while the temperature of the fluidic channel is within the first temperature range, the output indicating a magnitude of a first detected magnetic field. The method further comprises setting the temperature within the fluidic channel to be within the second temperature range, and obtaining the output from the selected one of the plurality of magnetic sensors while the temperature of the fluidic channel is within the second temperature range, the output indicating a magnitude of a second detected magnetic field. The method further comprises determining, based at least in part on the magnitude of the first detected magnetic field and the magnitude of the second detected magnetic field, whether the first type of MNP or the second type of MNP has been detected by the selected one of the plurality of magnetic sensors.

In some embodiments, the output comprises one or more of a resistance, a voltage, a current, a frequency, a noise, or a change in resistance, voltage, current, frequency, or noise.

In some embodiments, determining whether the first type of MNP or the second type of MNP has been detected by the selected one of the plurality of magnetic sensors comprises (a) in response to the magnitude of the first detected magnetic field being greater than or equal to the first threshold and the magnitude of the second detected magnetic field being less than the first threshold, determining that the first type of MNP has been detected by the selected one of the plurality of magnetic sensors, or (b) in response to the magnitude of the first detected magnetic field being greater than or equal to the second threshold and the magnitude of the second detected magnetic field being greater than or equal to the second threshold, determining that the second type of MNP has been detected by the selected one of the plurality of magnetic sensors.

In some embodiments, a Curie temperature of the first type of MNP differs from a Curie temperature of the second type of MNP. In some such embodiments, the Curie temperature of the second type of MNP is greater than the Curie temperature of the first type of MNP, and the method further comprises setting the temperature within the fluidic channel to a temperature value higher than the Curie temperatures of the first and second types of MNP before adding the first and second pluralities of molecules to be detected to the fluidic channel, and adding the first and second pluralities of molecules to be detected to the fluidic channel occurs while the temperature within the fluidic channel is at the temperature value higher than the Curie temperatures of the first and second types of MNP. In some embodiments in which the Curie temperature of the first type of MNP differs from the Curie temperature of the second type of MNP, the method further comprises setting a temperature of a mixture of the first and second pluralities of molecules to be detected to a temperature value higher than the Curie temperatures of the first and second types of MNP before adding the first and second pluralities of molecules to be detected to the fluidic channel.

In some embodiments, a blocking temperature of the first type of MNP differs from a blocking temperature of the second type of MNP.

In some embodiments, each of the first and second types of MNP is characterized by a blocking temperature, and the method further comprises setting the temperature within the fluidic channel to a temperature value higher than both of the blocking temperatures of the first and second types of MNP before adding the first and second pluralities of molecules to be detected to the fluidic channel, and adding the first and second pluralities of molecules to be detected to the fluidic channel occurs while the temperature within the fluidic channel is at the temperature value higher than the blocking temperatures of the first and second types of MNP. In some embodiments, each of the first and second types of MNP is characterized by a blocking temperature, and the method further comprises setting a temperature of a mixture of the first and second pluralities of molecules to be detected to a temperature value higher than both of the blocking temperatures of the first and second types of MNP before adding the first and second pluralities of molecules to be detected to the fluidic channel.

In some embodiments, first, second, and third pluralities of molecules are added to the fluidic channel. In some such embodiments, the magnitude of the magnetic field generated by the first type of MNP is less than the first threshold in a third temperature range, the third temperature range being higher than the second temperature range, and the magnitude of the magnetic field generated by the second type of MNP is less than the second threshold in the third temperature range. In some such embodiments, the method further comprises adding a third plurality of molecules to be detected to the fluidic channel, at least some of the third plurality of molecules to be detected being labeled by a third type of MNP, wherein, in the first, second, and third temperature ranges, a magnitude of a magnetic field generated by the third type of MNP is greater than or equal to a third threshold; setting the temperature within the fluidic channel to be within the third temperature range; obtaining the output of the selected one of the plurality of magnetic sensors while the temperature of the fluidic channel is within the third temperature range, the output indicating a magnitude of a third detected magnetic field; and determining, based at least in part on the magnitude of the third detected magnetic field, whether the third type of MNP has been detected by the selected one of the plurality of magnetic sensors. In some such embodiments, determining, based at least in part on the magnitude of the third detected magnetic field, whether the third type of MNP has been detected by the selected one of the plurality of magnetic sensors comprises, in response to the magnitude of the first detected magnetic field being greater than or equal to the third threshold, and the magnitude of the second detected magnetic field being greater than or equal to the third threshold, and the magnitude of the third detected magnetic field being greater than or equal to the third threshold, determining that the third type of MNP has been detected by the selected one of the plurality of magnetic sensors. In some embodiments, at least two of the first, second, and third thresholds are different.

In some embodiments in which first, second, and third pluralities of molecules are added to the fluidic channel, the first, second, and third pluralities of molecules are added to the fluidic channel at a substantially same time.

In some embodiments in which first, second, and third pluralities of molecules are added to the fluidic channel, a Curie temperature of the third type of MNP is higher than a Curie temperature of the second type of MNP, and the Curie temperature of the second type of MNP is higher than a Curie temperature of the first type of MNP.

In some embodiments in which first, second, and third pluralities of molecules are added to the fluidic channel, the method further comprises setting the temperature within the fluidic channel to a temperature value higher than the Curie temperatures of the first, second, and third types of MNP before adding the first, second, and third pluralities of molecules to be detected to the fluidic channel, and adding the first, second, and third pluralities of molecules to be detected to the fluidic channel occurs while the temperature within the fluidic channel is at the temperature value higher than the Curie temperatures of the first, second, and third types of MNP.

In some embodiments in which first, second, and third pluralities of molecules are added to the fluidic channel, a blocking temperature of the third type of MNP differs from a blocking temperature of the second type of MNP, and the blocking temperature of the second type of MNP differs from a blocking temperature of the first type of MNP.

In some embodiments, first, second, third, and fourth pluralities of molecules are added to the fluidic channel. In some such embodiments, the magnitude of the magnetic field generated by the first type of MNP is less than the first threshold in a fourth temperature range, the fourth temperature range being higher than the third temperature range, the magnitude of the magnetic field generated by the second type of MNP is less than the second threshold in the fourth temperature range, and the magnitude of the magnetic field generated by the third type of MNP is less than the third threshold in the fourth temperature range. In some such embodiments, the method further comprises adding a fourth plurality of molecules to be detected to the fluidic channel, at least some of the fourth plurality of molecules to be detected being labeled by a fourth type of MNP, wherein, in the first, second, third, and fourth temperature ranges, a magnitude of a magnetic field generated by the fourth type of MNP is greater than or equal to a fourth threshold; setting the temperature within the fluidic channel to be within the fourth temperature range; obtaining the output of the selected one of the plurality of magnetic sensors while the temperature of the fluidic channel is within the fourth temperature range, the output indicating a magnitude of a fourth detected magnetic field; and determining, based at least in part on the magnitude of the fourth detected magnetic field, whether the fourth type of MNP has been detected by the selected one of the plurality of magnetic sensors.

In some embodiments in which first, second, third, and fourth pluralities of molecules are added to the fluidic channel, determining whether the fourth type of MNP has been detected by the selected one of the plurality of magnetic sensors comprises, in response to the magnitude of the first detected magnetic field being greater than or equal to the fourth threshold, and the magnitude of the second detected magnetic field being greater than or equal to the fourth threshold, and the magnitude of the third detected magnetic field being greater than or equal to the fourth threshold, and the magnitude of the fourth detected magnetic field being greater than or equal to the fourth threshold, determining that the fourth type of MNP has been detected by the selected one of the plurality of magnetic sensors. In some such embodiments, two or more of the first, second, third, and fourth thresholds are different.

In some embodiments in which first, second, third, and fourth pluralities of molecules are added to the fluidic channel, the first, second, third, and fourth plurality of molecules to be detected are added to the fluidic channel at a substantially same time.

In some embodiments in which first, second, third, and fourth pluralities of molecules are added to the fluidic channel, a Curie temperature of the fourth type of MNP is higher than a Curie temperature of the third type of MNP, the Curie temperature of the third type of MNP is higher than a Curie temperature of the second type of MNP, and the Curie temperature of the second type of MNP is higher than a Curie temperature of the first type of MNP.

In some embodiments in which first, second, third, and fourth pluralities of molecules are added to the fluidic channel, the method further comprises setting the temperature within the fluidic channel to a temperature value higher than the Curie temperatures of the first, second, third, and fourth types of MNP before adding the first, second, third, and fourth pluralities of molecules to be detected to the fluidic channel, and adding the first, second, third, and fourth pluralities of molecules to be detected to the fluidic channel occurs while the temperature within the fluidic channel is at the temperature value higher than the Curie temperatures of the first, second, third, and fourth types of MNP.

In some embodiments in which first, second, third, and fourth pluralities of molecules are added to the fluidic channel, a blocking temperature of the fourth type of MNP differs from a blocking temperature of the third type of MNP, the blocking temperature of the third type of MNP differs from a blocking temperature of the second type of MNP, and the blocking temperature of the second type of MNP differs from a blocking temperature of the first type of MNP.

In some embodiments in which first, second, third, and fourth pluralities of molecules are added to the fluidic channel, the magnitude of the magnetic field generated by the first type of MNP is less than the first threshold in a fourth temperature range, the fourth temperature range being higher than the third temperature range, the magnitude of the magnetic field generated by the second type of MNP is less than the second threshold in the fourth temperature range, and the magnitude of the magnetic field generated by the third type of MNP is less than the third threshold in the fourth temperature range. In some such embodiments, the method further comprises adding a fourth, unlabeled plurality of molecules to be detected to the fluidic channel, setting the temperature within the fluidic channel to be within the fourth temperature range, obtaining the output of the selected one of the plurality of magnetic sensors while the temperature of the fluidic channel is within the fourth temperature range, the output indicating a magnitude of a fourth detected magnetic field, and, in response to the magnitude of the fourth detected magnetic field being less than the first threshold, less than the second threshold, and less than the third threshold, determining that none of the first, second, or third types of MNP has been detected by the selected one of the plurality of magnetic sensors.

In some embodiments in which first, second, third, and fourth pluralities of molecules are added to the fluidic channel, the magnitude of the magnetic field generated by the first type of MNP is less than the first threshold in a fourth temperature range, the fourth temperature range being higher than the third temperature range, the magnitude of the magnetic field generated by the second type of MNP is less than the second threshold in the fourth temperature range, and the magnitude of the magnetic field generated by the third type of MNP is less than the third threshold in the fourth temperature range. In some such embodiments, the method further comprises adding, to the fluidic channel, a fourth, unlabeled plurality of molecules to be detected, setting the temperature within the fluidic channel to be within the fourth temperature range, obtaining the output of the selected one of the plurality of magnetic sensors while the temperature of the fluidic channel is within the fourth temperature range, the output indicating a magnitude of a fourth detected magnetic field, and in response to the magnitude of the fourth detected magnetic field being less than the first threshold, less than the second threshold, and less than the third threshold, determining that one of the fourth, unlabeled plurality of molecules has been detected by the selected on of the plurality of magnetic sensors.

In some embodiments, a system for sequencing nucleic acid comprises (a) a fluidic channel having a plurality of sites for attaching, to a surface of the fluidic channel, a plurality of nucleic acid strands to be sequenced, (b) a temperature control device coupled to the fluidic channel for setting a temperature of a contents of the fluidic channel to be within any of first, second, and third temperature ranges, wherein the first, second, and third temperature ranges are nonoverlapping, (c) a plurality of magnetic sensors configured to detect a magnetic field emitted by one or more magnetic nanoparticles (MNPs) at each of the plurality of sites in each of the first, second, and third temperature ranges, and (d) at least one processor coupled to the magnetic sensors and to the temperature control device and configured to execute at least one machine-executable instruction. In some embodiments, at least one of the plurality of magnetic sensors comprises a magnetoresistive (MR) sensor. In some embodiments, the at least one machine-executable instruction, when executed, causes the at least one processor to (i) direct the temperature control device to set the temperature of the contents of the fluidic channel to be within the first temperature range, (ii) obtain a first output from a magnetic sensor associated with a particular site of the plurality of sites, the first output indicating a magnitude of a first detected magnetic field, (iii) direct the temperature control device to set the temperature of the contents of the fluidic channel to be within the second temperature range, (iv) obtain a second output of the magnetic sensor associated with the particular site of the plurality of sites, the second output indicating a magnitude of a second detected magnetic field, (v) direct the temperature control device to set the temperature of the contents of the fluidic channel to be within the third temperature range, (vi) obtain a third output of the magnetic sensor associated with the particular site of the plurality of sites, the third output indicating a magnitude of a third detected magnetic field, and (vii) determine, based at least in part on the magnitude of the first detected magnetic field, the magnitude of the second detected magnetic field, and the magnitude of the third detected magnetic field, whether a MNP of a particular type has been detected by the magnetic sensor. In some embodiments, at least one of the first, second, or third outputs comprises one or more of a resistance, a voltage, a current, a frequency, a noise, or a change in resistance, voltage, current, frequency, or noise. In some embodiments, the first temperature range is lower than the second temperature range, and the second temperature range is lower than the third temperature range.

In some embodiments, the fluidic channel comprises a structure comprising the plurality of sites for attaching, to the surface of the fluidic channel, the plurality of nucleic acid strands to be sequenced. In some such embodiments, the structure comprises a cavity or a ridge.

In some embodiments, the at least one machine-executable instruction, when executed, causes the at least one processor to determine whether a MNP of a particular type has been detected by the magnetic sensor by one or more of: (a) in response to the magnitude of the first detected magnetic field meeting or exceeding a first threshold, and the magnitude of the second detected magnetic field not meeting the first threshold, and the magnitude of the third detected magnetic field not meeting the first threshold, determining that a MNP of a first type has been detected by the magnetic sensor, (b) in response to the magnitude of the first detected magnetic field meeting or exceeding a second threshold, the magnitude of the second detected magnetic field meeting or exceeding the second threshold, and the magnitude of the third detected magnetic field not meeting the second threshold, determining that a MNP of a second type has been detected by the magnetic sensor, or (c) in response to the magnitude of the first detected magnetic field meeting or exceeding a third threshold, and the magnitude of the second detected magnetic field meeting or exceeding the third threshold, and the magnitude of the third detected magnetic field meeting or exceeding the third threshold, determining that a MNP of a third type has been detected by the magnetic sensor.

In some embodiments, when executed by the at least one processor, the at least one machine-executable instruction further causes the at least one processor to (a) direct the temperature control device to set the temperature of the contents of the fluidic channel to be within a fourth temperature range, the fourth temperature range being higher than the third temperature range, (b) obtain a fourth output from a magnetic sensor associated with a particular site of the plurality of sites, the fourth output indicating a magnitude of a fourth detected magnetic field, and (c) in response to the magnitude of the first detected magnetic field meeting or exceeding a fourth threshold, and the magnitude of the second detected magnetic field meeting or exceeding the fourth threshold, and the magnitude of the third detected magnetic field meeting or exceeding the fourth threshold, and the fourth detected magnetic field meeting or exceeding the fourth threshold, determining that a MNP of a fourth type has been detected by the magnetic sensor.

In some embodiments including a temperature control device, the temperature control device comprises at least one of a thermal sensor or a microprocessor. In some embodiments including a temperature control device, the temperature control device comprises a heater.

In some embodiments, a system for detecting magnetic nanoparticles (MNPs) coupled to molecules, the MNPs being characterized by a characteristic temperature below which the MNPs emit a magnetic field having a magnitude higher than a threshold and above which the MNPs do not emit the magnetic field having the magnitude higher than the threshold, comprises (a) a fluidic channel, (b) a temperature control device coupled to the fluidic channel for setting a temperature of a contents of the fluidic channel, (c) control circuitry coupled to the temperature control device and configured to direct the temperature control device to set the temperature of the contents of the fluidic channel to a first temperature and to a second temperature, the first temperature being higher than the characteristic temperature of the MNPs and the second temperature being lower than the characteristic temperature of the MNPs, (d) a magnetic sensor configured to detect a magnetic field emitted by one or more MNPs in the fluidic channel, and (e) detection circuitry coupled to the magnetic sensor and configured to obtain, from the magnetic sensor, an output indicating a magnetic field magnitude detected by the magnetic sensor.

In some embodiments, the characteristic temperature is a Curie temperature. In some embodiments, the characteristic temperature is a blocking temperature.

In some embodiments, the control circuitry is further configured to determine, based at least in part on the magnetic field magnitude detected by the magnetic sensor, whether a MNP has been detected by the magnetic sensor.

In some embodiments, the temperature of the contents of the fluidic channel is less than the characteristic temperature, and the at least one processor is configured to determine whether a MNP has been detected by the magnetic sensor by (i) comparing the magnetic field magnitude detected by the magnetic sensor to the threshold, and (ii) in response to the magnetic field magnitude detected by the magnetic sensor being greater than the threshold, determining that the MNP has been detected by the magnetic sensor.

In some embodiments, the temperature of the contents of the fluidic channel is greater than the characteristic temperature, and the at least one processor is configured to determine whether a MNP has been detected by the magnetic sensor by (i) comparing the magnetic field magnitude detected by the magnetic sensor to the threshold, and (ii) in response to the magnetic field magnitude detected by the magnetic sensor being less than the threshold, determining that the MNP has been detected by the magnetic sensor.

In some embodiments, the fluidic channel comprises a structure, and the structure comprises the plurality of sites for attaching, to the surface of the fluidic channel, a plurality of unidentified molecules to be identified. In some such embodiments, the structure comprises a cavity or a ridge.

In some embodiments, the temperature control device comprises at least one of a thermal sensor or a microprocessor. In some embodiments, the temperature control device comprises a heater.

In some embodiments, the magnetic sensor comprises a magnetoresistive (MR) sensor. In some embodiments, the output comprises one or more of a resistance, a voltage, a current, a frequency, a noise, or a change in resistance, voltage, current, frequency, or noise.

BRIEF DESCRIPTION OF THE DRAWINGS

So that the manner in which the above-recited features of the present disclosure can be understood in detail, a more particular description of the disclosure is provided in reference to embodiments, some of which are illustrated in the appended drawings. It is to be noted, however, that the appended drawings illustrate only typical embodiments of this disclosure and are therefore not to be considered limiting of its scope, for the disclosure may admit to other equally-effective embodiments. Objects, features, and advantages of the disclosure will be readily apparent from the following description of certain embodiments taken in conjunction with the accompanying drawings in which:

FIGS. 8A, 8B, and 8C illustrate a cross-point array architecture of MR sensor elements in accordance with some embodiments.

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION

Figure 1:
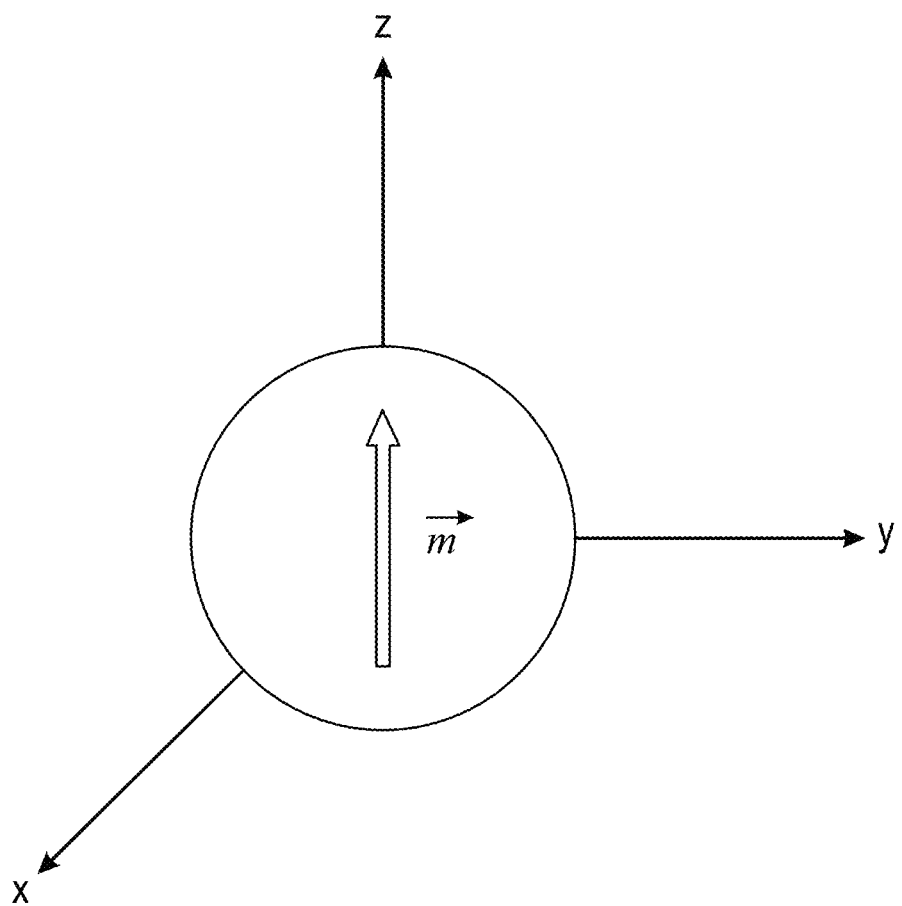
FIG. 1 illustrates an exemplary MNP, suitable for use in accordance with some embodiments, having a magnetization that is illustratively fixed along the z-axis due to magnetic anisotropy.

Disclosed herein are improved detection devices, systems, and methods that use magnetic nanoparticles (MNPs) to allow molecules to be identified. Embodiments of this disclosure are directed to various detection device and system embodiments using magnetic sensors capable of detecting the presence or absence of MNPs near the magnetic sensors, and detection method embodiments designed to determine (e.g., measure or obtain) outputs (e.g., resistance or change in resistance) indicative of the presence of MNPs. Embodiments of the present disclosure generally relate to devices and methods for using a magnetoresistive (MR) sensor array to detect molecules. For example, embodiments disclosed herein may be used for nucleic acid sequencing, such as deoxyribonucleic acid (DNA) sequencing.

Specifically, embodiments of this disclosure include magnetic sensors (e.g., magnetoresistive sensors) that can be used to detect temperature-dependent magnetic fields (or temperature-dependent changes in magnetic fields) emitted by MNPs, and, specifically to distinguish between the presence and absence of magnetic fields emitted, or not emitted, by MNPs at different temperatures selected to take advantage of knowledge of the MNPs' Curie temperatures.

In the following description, reference is made to embodiments of the disclosure. It should be understood, however, that the disclosure is not limited to specific described embodiments. Instead, any combination of the following features and elements, whether related to different embodiments or not, is contemplated to implement and practice the disclosure. Furthermore, although embodiments of the disclosure may achieve advantages over other possible solutions and/or over the prior art, whether or not a particular advantage is achieved by a given embodiment is not limiting of the disclosure. Thus, the following aspects, features, embodiments and advantages are merely illustrative. Likewise, reference to "the disclosure" shall not be construed as a generalization of any inventive subject matter disclosed herein.

The terms "over," "under," "between," "on," and other similar terms as used herein refer to a relative position of one layer with respect to other layers. As such, for example, one layer disposed over or under another layer may be directly in contact with the other layer or may have one or more intervening layers. Moreover, one layer disposed between layers may be directly in contact with the two layers or may have one or more intervening layers. In contrast, a first layer "on" a second layer is in contact with the second layer. The relative position of the terms does not define or limit the layers to a vector space orientation of the layers.

The term "coupled" is used herein to refer to elements that are either directly connected or connected through one or more intervening elements. For example, as explained below, a line (e.g., for selecting or reading an output from a magnetic sensor) may be directly connected to a magnetic sensor, or it may be connected to the sensor via intervening elements.

The terms "sense" and "detect" are used interchangeably herein to mean obtain information from a physical stimulus. Sensing and detecting include measuring.

Although some of the disclosure herein is provided in the context of nucleic acid sequencing, and specifically DNA sequencing, it is to be understood that the embodiments herein generally may be used to detect any type of molecule to which a magnetic particle (e.g., a magnetic nanoparticle) can be attached. The disclosure presumes that the particles attached are magnetic nanoparticles, but this presumption is exemplary and is not intended to be limiting. Any molecule type that can be labeled by a magnetic nanoparticle may be detected using the methods and detection devices disclosed herein. Such molecule types may be biologic molecule types, such as proteins, antibodies, etc. For example, the disclosures herein may be used to detect nucleic acids (e.g., in DNA sequencing). The disclosures herein may also be used to detect non-biologic (inorganic or non-living) molecules, such as contaminants, minerals, chemical compounds, etc. The presentation of portions of the disclosure in the context of nucleic acid sequencing is solely exemplary and is not intended to limit the scope of the present disclosure.

Furthermore, although the description herein focuses on DNA as an exemplary nucleic acid, the various embodiments described can be applied to nucleic acid sequencing in general. Similarly, although SBS is used for illustrative purposes in the following description, the various embodiments are not so limited to SBS sequencing protocols (e.g., dynamic sequencing could be used instead).

Conventional nucleic acid sequencing, such as that used for DNA sequencing, typically relies on the detection of fluorescence. Specifically, fluorescence-based technologies used to differentiate between different bases in a sample (e.g., in fluorescence-based nucleic acid sequencing technologies) rely on, for example, the quality of a signal generated by a detection moiety that is associated with a particular type of nucleotide. For example, conventional fluorescent sequencing technologies utilize identifiably-distinct fluorescent moieties, each attached to one of the four nucleotides A, T, C, and G that are utilized in a sequencing reaction.

One conventional method of DNA sequencing involves adapting single-strand DNA (ssDNA) for attachment to a solid support of a sequencing apparatus and amplifying the quantity of the ssDNA using techniques such as the polymerase chain reaction to create many DNA molecules with a short leader. An oligo complementary to the short leader may then be added so that there is a short section of double-stranded DNA (dsDNA) at the leader. The double stranded portion of the bound molecule is a primer for a suitable DNA polymerase, such as, for example, Taq polymerase, which is operable at high temperatures.

The sequencing can then take one of several approaches. For example, the sequencing can use a mixture of four fluorescently-labeled 3'-blocked dNTPs (fluorescently labeled dideoxynucleotide terminators), where the fluorescent label is part of the 3'-blocking group. The fluorescent label serves as a "reversible terminator" for polymerization. Each of the NTPs is labeled by a different label (i.e., each of the A, G, C, and T nucleotides has a different label), and the different labels are distinguishable by fluorescent spectroscopy or by other optical means.

Four fluorescently-labeled nucleotide precursors can be used to sequence millions of clusters of DNA strands in parallel. DNA polymerase catalyzes the incorporation of fluorescently-labeled dNTPs into a DNA template strand during sequential cycles of DNA synthesis. In each sequencing cycle, the bound double strand DNA molecule is exposed to DNA polymerase and a mixture of the four fluorescently-labeled 3'-blocked NTPs. The polymerase adds one of the four dNTPs to the growing oligonucleotide chain (whichever dNTP is complementary to the next unpaired base in the ssDNA). The unincorporated dNTPs and other impurities that are either left unreacted or generated during the reactions are then separated from the vicinity of the support-bound DNA by washing at a temperature that prevents the free dNTPs from binding to the ssDNA but is not so high as to dehybridize the dsDNA.

Because only one of the four types of dNTP will have been added to the oligonucleotide, and the four fluorescent labels are distinguishable, the identity of the incorporated dNTP can be identified through laser excitation and imaging. Specifically, each of four filters is used to determine whether light of a particular wavelength (e.g., color) is emitted. The fluorescent label can then be enzymatically cleaved to allow the next round of incorporation. Because each base type can pair with one and only one other base type, the identity of the just-paired base in the unknown sequence of the ssDNA is known from the identity of the incorporated dNTP (which is known from the wavelength of emitted light). Thus, the base is identified directly from fluorescence measurements during each cycle.

One disadvantage of the above-described approach is that a complicated optics system is needed to filter out different wavelengths of light to detect the fluorescent labels of the incorporated dNTPs and to distinguish between the different emitted colors. Other approaches have been developed to simplify the optics system, but they are slower to sequence and require intermediate chemistry steps within each sequencing cycle. Thus, these approaches have been introduced in smaller, less expensive entry-level sequencing systems but not in higher-level systems requiring fast throughput.

Disclosed herein are improved detection devices, systems, and methods that use magnetic nanoparticles (MNPs) to allow molecules to be identified. Embodiments of this disclosure are directed to various detection device and system embodiments using magnetic sensors capable of obtaining outputs indicating the presence or absence of MNPs near the magnetic sensors, and detection method embodiments designed to determine (e.g., measure or obtain) outputs (e.g., resistance or change in resistance) indicative of the presence of MNPs.

As explained previously, the disclosures herein may be used to detect any type of molecule (e.g., biologic, organic, inorganic, or non-living) to which a magnetic particle (e.g., a MNP) can be attached. Apparatuses and methods disclosed herein use MNPs and magnetic sensors to perform detection of molecules, such as in nucleic acid sequencing (e.g., DNA sequencing using SBS chemistry methods). Specifically, embodiments of this disclosure include magnetic sensors (e.g., magnetoresistive sensors) that can be used to detect temperature-dependent magnetic fields (or changes in magnetic fields) emitted by MNPs, and, specifically to distinguish between the presence and absence of magnetic fields emitted, or not emitted, by MNPs at different temperatures selected to take advantage of knowledge of the MNPs' Curie temperatures. Embodiments that use the same MNP type for all molecules to be detected are disclosed, as are embodiments that use multiple MNP types, each type labeling a different molecule type and having a different Curie temperature. The disclosed embodiments allow different types of detected molecules to be distinguished. Moreover, by appropriate selection of the MNPs and their Curie temperatures, and the temperature at which MNP-labeled molecules are added to a fluidic channel of a detection device, clumping or clustering of MNP-labeled molecules added to a detection device can be mitigated.

Certain embodiments of the present disclosure also include various detection methods to obtain or determine (e.g., measure) outputs of the magnetic sensors (e.g., a resistance, a voltage, a current, a frequency, a noise, and/or a change in resistance, voltage, current, frequency, and/or noise) caused by MNPs used as labels being near the magnetic sensors. Knowledge of which particular molecule type (e.g., in DNA sequencing applications, the type of base) to which the particular MNP label has been attached, and the Curie temperature of that molecule, may then be used to identify the particular molecule type (e.g., in DNA sequencing applications, the last-paired base of the ssDNA strand).

MNPs

MNPs that are suitable for use in biologic molecule detection applications have a wide range of sizes (e.g., tens to hundreds of nanometers (nm)) and shapes (e.g., spherical, cubic, pyramidal, etc.). The magnetism in these particles is due to exchange interactions in the materials that align unpaired core electrons in the material's lattice in the same direction, resulting in a net moment of angular momentum in the material that is also called the magnetic moment or magnetization of the nanoparticle. (The terms "magnetic moment" and "magnetization" are used interchangeably herein.) The magnetic moment (a dipole moment within an atom that originates from the angular momentum and spin of electrons) of the MNP, at least at some temperatures, gives rise to magnetic fields that, as described further below, can be used to detect the presence of the MNP. Additional magnetic anisotropy energies (e.g., magnetocrystalline, demagnetization) also help define stable orientations for the magnetization of the MNP, so that, when the spatial orientation of a particle is well defined, so is the magnetization direction of the particle. FIG. 1 illustrates an exemplary MNP having a magnetization that is illustratively fixed along the z-axis due to magnetic anisotropy. It is to be understood that if the particle is mechanically rotated, so is the magnetization direction.

The magnetization of a MNP is temperature-dependent, and for MNPs that are sufficiently small, there are two temperatures at which their magnetic properties change significantly. The first change occurs at what is referred to as the blocking temperature, denoted as $T_B$. When a nanoparticle is sufficiently small, its magnetization can flip direction randomly in the absence of an external magnetic field. At this point, the thermal energy of the particle (kT) is sufficiently larger than the anisotropy energies such that the magnetization no longer points along a single axis. Instead, the magnetization can randomly flip or rotate between two or more orientations, at which point the MNP transitions from being ferromagnetic to being considered superparamagnetic. (Magnetic nanoparticles are said to be "superparamagnetic" when the loop area of their hysteresis loop, when measured under quasi-static conditions, is zero, which occurs when the nanoparticle cores are small enough to support only one magnetic domain per core, in which case they are single-domain particles.)

The magnetic properties of a MNP also change at or around the Curie temperature, denoted as $T_C$, which is greater than or equal to the blocking temperature. The Curie temperature (sometimes referred to as the ferromagnetic transition temperature) is the temperature above which ferromagnetic materials lose their permanent magnetic properties and become paramagnetic. Ferromagnetic and paramagnetic materials have different intrinsic magnetic moment structures, and these properties change at a material's Curie temperature. Stated another way, ferromagnetism appears only below the Curie temperature. At temperatures above the Curie temperature, the thermal energies are large enough to overcome the exchange interactions amongst the core electrons and eliminate the net moment of the MNP. Consequently, the ordered magnetic moments change and become disordered (e.g., oriented randomly, resulting in a zero net magnetization). Below the Curie temperature, a MNP is ferromagnetic (has moments that are magnetized spontaneously) and, as such, generates a magnetic field, but above the Curie temperature, the particle is in a paramagnetic state and does not generate a spontaneous magnetic field of its own.

The inventors of the present disclosure had the insight that the differences in MNPs' magnetic properties around the blocking temperature and around the Curie temperature can be exploited for molecule detection, as explained in further detail below.

As will be appreciated by those having ordinary skill in the art, there are many suitable MNPs that can be used with the systems and methods described below. For example, the Curie temperature of a MNP may be adjusted over a small range between room temperature and 100° C. by changing the composition of compounds. For example, $Y_3Fe_{5-x}Al_xO_{12}$ particles with an average diameter of 100 nm and with Curie temperatures varying from 7 to 140° C. by varying the aluminum content in the MNP have been synthesized (see, e.g., Grasset et al., "Synthesis, magnetic properties, surface modification and cytotoxicity evaluation of $Y_3Fe_{5-x}Al_xO_{12}$ garnet submicron particles for biomedical applications," JMMM, 234 (2001) 409-418, which is hereby incorporated by reference in its entirety for all purposes). $La_{1-x}Sr_xMn_{1-y}Ti_yO_3$ particles having Curie temperatures between 20 and 90° C. by varying the titanium content have also been synthesized (see, e.g., Phuc et al., "Tuning of the Curie Temperature in $La_{1-x}Sr_xMn_{1-y}Ti_yO_3$," Journal of the Korean Physical Society, Vol. 52, No. 5, May 2008, pp. 1492-1495, which is hereby incorporated by reference in its entirety for all purposes). Finally, GdSi alloys doped with elements such as germanium, erbium, and rhodium have shown Curie temperatures in a range around room temperature with smaller (approximately 40 nm diameter) sizes and more regular spherical shapes (see, e.g., Alnasir et. al, "Magnetic and magnetothermal studies of pure and doped gadolinium silicide nanoparticles for self-controlled hyperthermia applications," JMMM, 449 (2018) 137-144, which is hereby incorporated by reference in its entirety for all purposes). These examples represent only a small sample of possible materials for generating MNPs suitable for use with the disclosed embodiments and are not meant to be limiting. Those having skill in the art will understand that many MNPs having the properties described in this disclosure exist or can be developed without substantial experimentation. Moreover, those skilled in the art will recognize that the blocking temperature may also be adjusted by doping, for example, by changing the crystalline structure of a material.

Once the MNPs have been selected, there are a number of ways to attach the MNPs to the molecules to be detected and (if applicable) to cleave the MNPs following detection. For example, the MNPs may be attached to a base or a molecule to be detected, in which case the MNPs may be cleaved chemically. As another example, the MNPs may be attached to a phosphate, in which case the MNPs may be cleaved by, for example, polymerase or, if attached via a linker, by cleaving the linker.

In some embodiments for nucleic acid sequencing, the MNP is linked to the nitrogenous base (e.g., A, C, T, G, or a derivative) of the nucleotide precursor. After incorporation of the nucleotide precursor and detection by a detection device (e.g., as described below), the MNP may be cleaved from the incorporated nucleotide.

In some embodiments, the MNP is attached via a cleavable linker. Cleavable linkers are known in the art and have been described, e.g., in U.S. Pat. Nos. 7,057,026, 7,414,116 and continuations and improvements thereof. In some embodiments, the MNP is attached to the 5-position in pyrimidines or the 7-position in purines via a linker comprising an allyl or azido group. In some embodiments, the linker comprises a disulfide, indole, a Sieber group, a t-butyl Sieber group, and/or a dialkoxybenzyl group. The linker may further contain one or more substituents selected from alkyl (such as $C_{1-6}$) or alkoxy (such as $C_{1-6}$), nitro, cyano, fluoro groups or groups with similar properties. Briefly, the linker can be cleaved by water-soluble phosphines and/or phosphine-based transition metal-containing catalysts. Other linkers and linker cleavage mechanisms are known in the art. For example, linkers comprising trityl groups, p-alkoxybenzyl ester groups, p-alkoxybenzyl amide groups, tert-butyloxycarbonyl (Boc) groups, and acetal-based groups can be cleaved under acidic conditions by a proton-releasing cleavage agent such as an acid. A thioacetal or other sulfur-containing linker can be cleaved using a thiophilic metals, such as nickel, silver, and/or mercury. The cleavage protecting groups can also be considered for the preparation of suitable linker molecules. Ester- and disulfide containing linkers can be cleaved under reductive conditions. Linkers containing triisopropyl silane (TIPS) or t-butyldimethyl silane (TBDMS) can be cleaved in the presence of F ions. Photocleavable linkers cleaved by a wavelength that does not affect other components of the reaction mixture include linkers comprising o-nitrobenzyl groups. Linkers comprising benzyloxycarbonyl groups can be cleaved by Pd-based catalysts.

In some embodiments, the nucleotide precursor comprises a MNP label attached to a polyphosphate moiety as described in, e.g., U.S. Pat. Nos. 7,405,281 and 8,058,031. Briefly, the nucleotide precursor comprises a nucleoside moiety and a chain of 3 or more phosphate groups where one or more of the oxygen atoms are optionally substituted, e.g., with S. The label may be attached to the $\alpha$, $\beta$, $\gamma$ or higher phosphate group (if present) directly or via a linker. In some embodiments, the MNP label is attached to a phosphate group via a non-covalent linker as described, e.g., in U.S. Pat. No. 8,252,910. In some embodiments, the linker is a hydrocarbon selected from substituted or unsubstituted alkyl, substituted or unsubstituted heteroalkyl, substituted or unsubstituted aryl, substituted or unsubstituted heteroaryl, substituted or unsubstituted cycloalkyl, and substituted or unsubstituted heterocycloalkyl; see, e.g., U.S. Pat. No. 8,367,813. The linker may also comprise a nucleic acid strand; see, e.g., U.S. Pat. No. 9,464,107.

In embodiments in which the MNP is linked to a phosphate group, the nucleotide precursor may be incorporated into the nascent chain by the nucleic acid polymerase, which also cleaves and releases the detectable MNP. In some embodiments, the MNP is removed by cleaving the linker, e.g., as described in U.S. Pat. No. 9,587,275.

In some embodiments, the nucleotide precursors are non-extendable "terminator" nucleotides, i.e., the nucleotides that have a 3'-end blocked from addition of the next nucleotide by a blocking "terminator" group. The blocking groups are reversible terminators that can be removed in order to continue the strand synthesis process as described herein. Attaching removable blocking groups to nucleotide precursors is known in the art. See, e.g., U.S. Pat. Nos. 7,541,444, 8,071,739 and continuations and improvements thereof. Briefly, the blocking group may comprise an allyl group that can be cleaved by reacting in aqueous solution with a metal-allyl complex in the presence of phosphine or nitrogen-phosphine ligands.

Detection Methods

Some embodiments herein are directed to detection methods that use a detection device and exploit the temperature-dependence of the magnetic properties of MNPs to detect the presence of molecules within a fluidic channel (also referred to herein as a nanochannel, a nanofluidic channel, and/or a microfluidic channel) of a detection device (exemplary embodiments of which are described in the discussions of, for example, FIGS. 8A through 15).

In some embodiments, MNPs are coupled to molecules to be detected (e.g., dNTPs in DNA sequencing applications) in any suitable way (e.g., as described above). Using magnetic sensors (e.g., any of a variety of embodiments of the magnetic sensors 105 described in further detail below), the detection device can then sense the presence and/or absence of MNPs in one or more fluidic channels. By performing detection at temperatures both below and above what is referred to herein as a characteristic temperature (e.g., the Curie temperature(s), the blocking temperature(s), or any other temperature around which the magnetic properties of the MNP change) of the MNP(s) labeling the molecules to be detected, the detection device can determine that a MNP is present when it detects a magnetic field exceeding a threshold at a characteristic temperature below the applicable characteristic temperature but not at a characteristic temperature above the applicable characteristic temperature (e.g., the Curie temperature(s) or the blocking temperature(s)).

At various points in this document, it is assumed for convenience and simplification of the explanation that the magnetic properties of a MNP change abruptly around a characteristic temperature (e.g., the blocking temperature, Curie temperature, etc.). It is to be understood, however, that the magnetic properties of a MNP might not, and need not, change abruptly at the characteristic temperature. For example, at temperatures in a range below but near the Curie temperature, the magnetization may generally decrease with increasing temperature (monotonically or non-monotonically), eventually reaching a minimum value of about zero at the Curie temperature. Accordingly, it will be appreciated that in various embodiments disclosed herein, when detection below the characteristic temperature (e.g., Curie temperature or blocking temperature) is performed, it may be desirable to perform detection at a temperature that is some number of degrees below the characteristic temperature. For example, it may be desirable, when performing detection at a temperature below the Curie temperature, to set the temperature to some percentage or fraction of the Curie temperature (e.g., $T_m = p \times T_c$, where $T_m$ is the temperature at which the detection is performed and $0 < p < 1$). As another example, it may be desirable to set the temperature within a specified range below the Curie temperature, where there is a buffer between the top end of the specified range and the Curie temperature (e.g., $T_1 \leq T_m \leq T_2$, where $T_m$ is the temperature at which the detection is performed, $T_1 \ll T_c$, and $T_2 < T_c$, and there is a buffer between $T_c$ and $T_2$). The objective is to detect, based on a sensed magnetic property, whether a MNP is in the vicinity of a magnetic sensor, and those having ordinary skill in the art will understand how to select an appropriate temperature at which to perform detection based on knowledge of the characteristic temperature, the magnetic properties of the selected MNP type at temperatures around the characteristic temperature, and the disclosures herein.

As a specific example of the use of MNPs for molecule detection, in DNA sequencing applications, molecules of each of the four types of nucleotide precursors (A, T, C, and G) can be labeled by a MNP. As individual dNTPs are incorporated into target DNA strands present within the fluidic channel in the vicinities of magnetic sensors, the presence, at a particular magnetic sensor, of a sensed magnetic field associated with a MNP at a temperature below a characteristic temperature (e.g., its Curie or blocking temperature) and the absence of a sensed magnetic field at a temperature above this characteristic temperature indicates that a nucleotide precursor labeled by that MNP has been incorporated in a DNA strand being sequenced and sensed by that particular magnetic sensor. Conversely, when a particular magnetic sensor fails to detect a magnetic field associated with the MNP at a temperature below the characteristic temperature (e.g., the Curie temperature or blocking temperature), it can be deduced that the nucleotide precursor labeled by that MNP has not been incorporated into a DNA strand in the vicinity of the particular sensor.

Continuing with the example of DNA sequencing, there are at least two ways to perform DNA sequencing: (1) using a sequential binary method with one MNP type used to label all four nucleotide precursors, and (2) using multiple distinguishable MNP types, each labeling a different one of the nucleotide precursors.

In a sequential binary method, the magnetically-labeled nucleotide precursors (each labeled by the same type of MNP) are added one by one to a detection device (e.g., to a fluidic channel of such a detection device). A detection process follows the introduction of each nucleotide precursor to detect whether that nucleotide precursor was incorporated into a DNA strand near each of one or more magnetic sensors. Following the addition of the MNP-labeled nucleotide precursor being tested, the temperature is set to be within a first range that is either below or above a characteristic (e.g., Curie or blocking) temperature of the MNP being used as a magnetic label, and the magnetic sensors are used to detect magnetic fields emanating from MNPs in their vicinities. The magnetic sensors may detect magnetic fields by detecting, for example, a resistance, a voltage, a current, a frequency, a noise, and/or a change in resistance, voltage, current, frequency, and/or noise, and the output of each magnetic sensor may indicate the magnitude of the field detected.

Figure 2A:
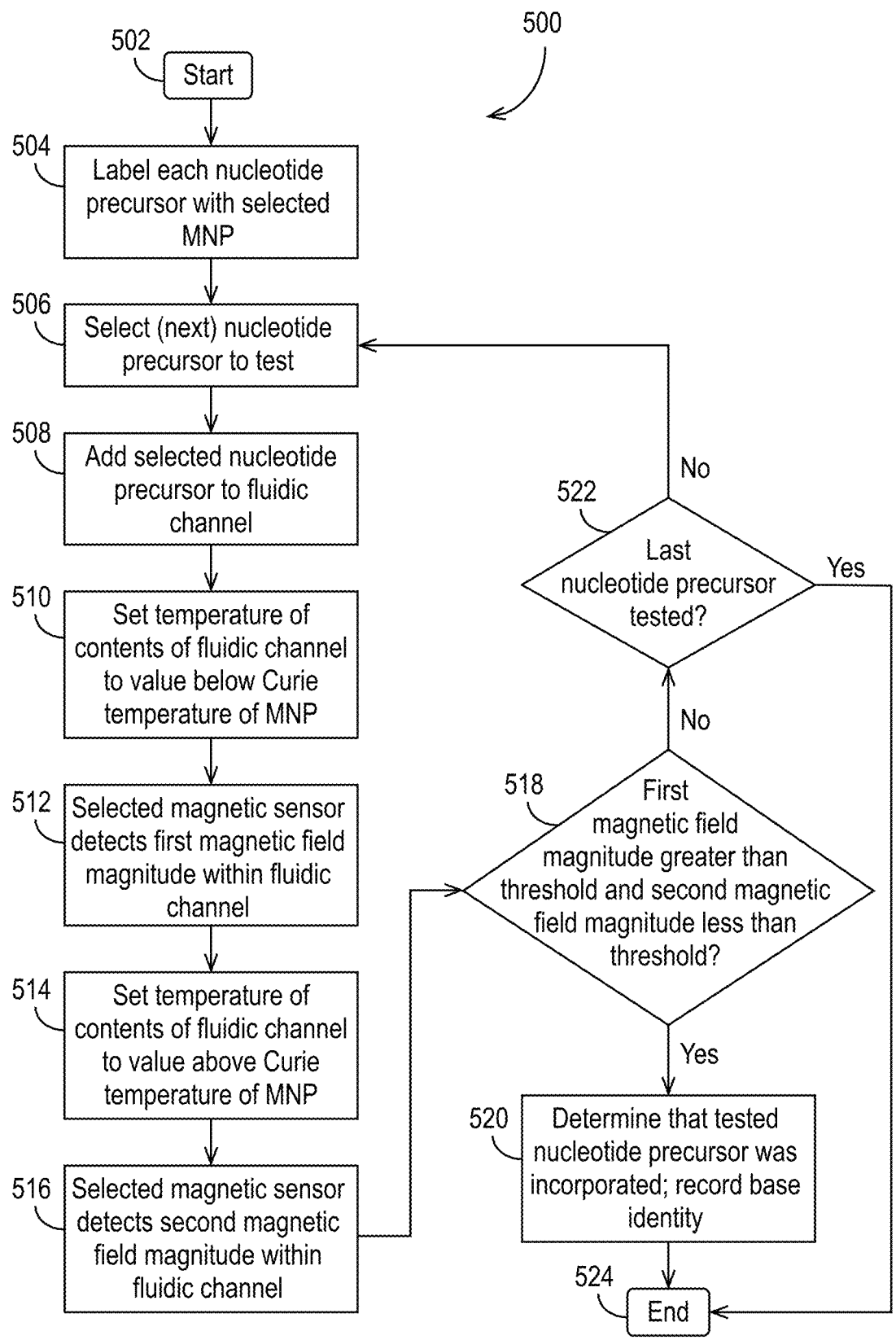
FIG. 2A illustrates an exemplary sequential binary method suitable for DNA sequencing in accordance with some embodiments.

FIG. 2A illustrates an exemplary sequential binary method 500 suitable for DNA sequencing in accordance with some embodiments. FIG. 2A illustrates the exemplary method 500 assuming the Curie temperature is exploited, but it is to be appreciated that other characteristic temperatures, such as the blocking temperature, may be used instead. At 502, the method begins. At 504, molecules of each the four nucleotide precursors (A, T, C, and G) are all labeled by the same type of MNP. The different nucleotide precursors, each labeled by the same MNP type, are then introduced one at a time into, for example, a fluidic channel of a detection device. Thus, at 506, a first nucleotide precursor to be tested is selected. At 508, the selected (magnetically-labeled) nucleotide precursor is added to the fluidic channel of a detection device. At 510, the temperature of the contents of the fluidic channel is set to a value below the Curie temperature of the MNP being used as the magnetic label. The temperature may be set, for example, using a temperature control device (e.g., a heater) to heat the contents of the fluidic channel. Alternatively or in addition, the nucleotide precursor may be heated (or cooled) prior to being added to the fluidic channel. At 512, a selected magnetic sensor detects a first magnetic field magnitude in its vicinity (e.g., presumed to be caused by MNPs within the fluidic channel). As explained above, the magnetic sensor(s) may sense the magnetic field emitted by one or more MNPs by detecting a resistance, a voltage, a current, a frequency, a noise, and/or a change in resistance, voltage, current, frequency, and/or noise. The sensing may take place over a specified time period sufficient to reduce or eliminate transient effects (e.g., to provide an average). The sensed magnetic field magnitude may be recorded.

At 514, the temperature of the contents of the fluidic channel is set to a value above the Curie temperature of the MNP being used as the label. The temperature may be set, for example, using a temperature control device (e.g., a heater) to heat the contents of the fluidic channel. Alternatively or in addition, the nucleotide precursor may be heated (or cooled) prior to being added to the fluidic channel. At 516, each of the selected one or more magnetic sensors detects a second magnetic field magnitude in its vicinity (e.g., if present, presumed to be caused by MNPs within the fluidic channel). The sensed magnetic field magnitude may be recorded. At 518, a binary (yes/no, 1/0, etc.) determination may be made based on the sensed magnetic fields at the two temperatures as to whether the magnetically-labeled nucleotide precursor being tested has been incorporated into a DNA strand near each of the one or more magnetic sensors. As shown in the exemplary method of FIG. 2A, if the first magnetic field magnitude is greater than a threshold (e.g., a magnetic field magnitude expected from a MNP in the magnetic sensor's vicinity) and the second magnetic field magnitude is less than the threshold, then at 520 it is determined that the nucleotide precursor selected at 506 was incorporated into the target DNA strand(s) associated with (e.g., being sensed by) the magnetic sensor. The identity of either the nucleotide precursor itself or the complementary base of the target DNA strand may be recorded, and the method ends at 524.

If, however, it is determined at 518 that the first magnetic field magnitude is not greater than the threshold or the second magnetic field magnitude is not less than the threshold, then at 522 it is determined whether there are more nucleotide precursors to be tested during the sequencing cycle. If so, the MNPs may be cleaved from the DNA sub-strands, and the next nucleotide precursor may be introduced and detected in a similar manner. In the exemplary embodiment of FIG. 2A, the method returns to 506, where another nucleotide precursor is selected, and the procedure described above is repeated. If, at 522, it is determined there are no more nucleotide precursors to be tested during the current sequencing cycle, the method ends at 524.

Although FIG. 2A illustrates first setting the temperature of the contents of the fluidic channel to a value below the Curie temperature, sensing the magnetic field, and then setting the temperature to a value above the Curie temperature and sensing the magnetic field, it is to be understood that the order of the temperature-setting steps may be reversed. For example, the temperature may first be set to a value above the Curie temperature for the first magnetic field magnitude sensing step (514), and the contents of the fluidic channel may be cooled to a value below the Curie temperature for the second magnetic field magnitude sensing step (510). In other words, the second temperature is within a range that is above the Curie temperature if the first temperature was within a range below the Curie temperature, and the second temperature is within a range that is below the Curie temperature if the first temperature was within a range above the Curie temperature.

Moreover, although FIG. 2A assumes that each of the nucleotide precursors is labeled by the same type of MNP, it is not a requirement to use the same type of MNP for each of the nucleotide precursors. For example, it may be convenient to use the same type of MNP for each of the nucleotide precursors, but, alternatively, different nucleotide precursors may be labeled by different types of MNP. In other words, two or more of the nucleotide precursors may be labeled by the same type of MNP, or two or more nucleotide precursors may be labeled by different types of MNP.

The method 500 can be performed using one or more magnetic sensors. It is to be appreciated that when more than one magnetic sensor is used, the decision at 518 can differ for different magnetic sensors. For example, in some types of SBS, a long strand of DNA is (or a plurality of long strands of DNA from a single donor organism are) cut into smaller, random-length segments prior to sequencing. All of these smaller strands, which are from the same donor, are randomized sub-strands of the complete strand to be sequenced. For example, if the complete strand includes the sequence ATGGCTTAG, the smaller strands could include, for example, distinct sub-strands (e.g., ATGG and TTAG) as well as, if a plurality of the longer strands are cut into sub-strands, sub-strands that partially or completely overlap other sub-strands (e.g., GGCTT and ATGGCT). All of the smaller, randomized sub-strands may be sequenced at the same time, potentially after being amplified. In such applications, it will be appreciated that because the sub-strands do not represent the same sub-sequences, it may be desirable for each magnetic sensor to detect magnetic fields and/or changes in magnetic fields caused by single MNPs because the sequencing of the sub-strands will not be coordinated (or synchronized) amongst sub-strands. For example, during a single sequencing cycle, a first sub-strand may incorporate cytosine, a second sub-strand might incorporate thymine, and a third sub-strand might incorporate adenine. In order to sequence multiple random segments of a larger nucleic acid strand, it is desirable, in each sequencing cycle, to determine whether and at which physical location(s) each dNTP type has been incorporated. Accordingly, when using the exemplary method 500 shown in FIG. 2A, the decision at 518 may be "yes" for one magnetic sensor and "no" for another. Thus, when sequencing randomized sub-strands of a nucleic acid such as DNA, it may be desirable to test all four nucleotide precursors during each sequencing cycle, even though for some of the magnetic sensors the decision at 218 is "yes" for the first, second, or third tested nucleotide precursor.

Various other embodiments are directed to using multiple MNP types (for example, MNP 1, 2, 3, and 4), each with, for example, a different $T_B$ or $T_c$ within a range of temperatures, from, for example, room temperature up to the temperatures used for different DNA sequencing chemistries (which can be on the order of 80-100 degrees Celsius). Focusing on the DNA example for illustration, each individual base (A, T, C, G) can be labeled by a different type of MNP (e.g., base A with MNP 1, base C with MNP 2, base G with MNP 3, and base T with MNP 4) by either tagging each base separately and mixing them together or functionalizing each type of MNP differently so that it has an affinity for a particular (e.g., its assigned) base. In a single chemistry run, all tagged (magnetically-labeled) bases may be introduced into a microfluidic cell (e.g., the fluidic channel of the detection device described in detail below) in which DNA strands (e.g., fragments) to be sequenced have been attached within the microfluidic cell (e.g., as described in the discussion below of the detection device).

Accordingly, in some embodiments, instead of using a binary method with four chemistry steps for each base read (sequencing cycle) as described above, either three or four different MNPs, each having, for example, a different Curie temperature, can be used as the magnetic labels, and all of them can be detected in a single chemistry step. For example, each type of molecule (e.g., in DNA sequencing applications, each dNTP type) can be labeled by a different MNP type, where each MNP type has a different Curie temperature and/or different temperature dependence around the Curie temperature enabling it to be distinguished from all other MNPs being used as magnetic labels. For example, in a DNA sequencing application, A can be labeled by MNP1, T by MNP2, C by MNP3, and G either by MNP4 or left unlabeled, where the Curie temperatures of MNP1, MNP2, MNP3, and (if used) MNP4 are all different enough that the three or four types of MNPs can be distinguished by detecting whether, at a particular temperature, a magnetic field exceeding a threshold (which may be MNP-dependent or temperature-dependent, for example) is being emitted in the vicinity of a magnetic sensor. Then all three or four magnetically-labeled nucleotide precursors can be introduced into the fluidic channel at the same time, and changes in magnetic fields in the vicinities of the magnetic sensors of the detection device can be used to identify which MNP (and, therefore, type of base), if any, has been incorporated in the vicinity of each magnetic sensor. The target DNA strands to be sequenced have already been attached to the detection device with polymerase, which acts to incorporate nucleotide precursors that are complementary to those in the target strand.

Because the different MNP types coupled to different nucleotide precursors have different Curie temperatures, and therefore switch from being ferromagnetic to being paramagnetic (or vice versa) at different, distinguishable temperatures, all four bases can be detected during a single chemistry step. For example, in some embodiments, a first molecule type (e.g., adenine (A) in a DNA sequencing application) is tagged by a first MNP type that has a first Curie temperature $T_1$, a second molecule type (e.g., cytosine (C) in a DNA sequencing application) is tagged by a second MNP type that has a second Curie temperature a third molecule type (e.g., guanine (G) in a DNA sequencing application) is tagged by a third MNP type that has a third Curie temperature $T_{c,3}$; and a fourth molecule type (e.g., thymine (T) in a DNA sequencing application) is tagged by a fourth MNP type that has a fourth Curie temperature $T_{c,4}$. The four molecule types can then be distinguished by varying the temperature of the contents of the fluidic channel and detecting, at each selected temperature, using magnetic sensors, the magnetic field magnitude in the vicinity of each of the sensors. By comparing the magnetic field magnitudes at the various temperatures, it can be determined which, if any, of the four MNP types is in the vicinity of each of the sensors.

For example, assume the Curie temperatures are in the relationship $T_{c,1} < T_{c,2} < T_{c,3} < T_{c,4}$. Assume further, for the sake of explanation, that the magnetizations of the MNPs are step-like about their Curie temperatures, such that the first MNP type ("MNP1") emits a magnetic field having a magnitude above a first threshold ("Th1") at temperatures below $T_{c,1}$ and below the first threshold at temperatures above $T_1$; the second MNP type ("MNP2") emits a magnetic field having a magnitude above a second threshold ("Th2") at temperatures below $T_{c,2}$ and below the second threshold at temperatures above $T_{c,2}$; the third MNP type ("MNP3") emits a magnetic field having a magnitude above a third threshold ("Th3") at temperatures below $T_{c,3}$ and below the third threshold at temperatures above $T_{c,3}$; and the fourth MNP type ("MNP4") emits a magnetic field having a magnitude above a fourth threshold ("Th4") at temperatures below $T_{c,4}$ and below the fourth threshold at temperatures above $T_{c,4}$. (As explained above, the magnetization may change less abruptly about the Curie temperature than the step-like behavior assumed here, in which case "at temperatures below [the Curie temperature]" may be interpreted as "at temperatures below [the Curie temperature minus a suitable buffer]." Similarly, "at temperatures above [the Curie temperature]" may be interpreted as "at temperatures above [the Curie temperature plus a suitable buffer].") The thresholds may be in some kind of relationship (e.g., two or more of the thresholds can be the same, or all of the thresholds can be the same), or there may be no relationship between the thresholds (e.g., some or all of the thresholds can be different. In a DNA sequencing application, for example, the identity of the MNP, and therefore the identity of the incorporated nucleotide precursor (base incorporated in a target ssDNA) labeled by the MNP, can be determined using Table A below:

Thus, if, for example, the magnitude of the magnetic field detected by a particular magnetic sensor is above a specified threshold, Th2, in temperature ranges 1 and 2, but below that threshold in ranges 3 and 4, it can be determined that MNP type 2 has been detected. In the exemplary DNA sequencing application, therefore, the incorporated nucleotide precursor is cytosine (C), and the identity of the last-paired base in the DNA strand being sequenced is the complement of cytosine, which is guanine (G).

In embodiments in which each nucleotide precursor is labeled by a different MNP type, each different MNP type having a different Curie temperature, detection in the temperature range below the lowest Curie temperature of the MNPs (Range 1 in the table above) may be skipped because, as shown in the table above, all of the MNPs emit magnetic fields having magnitudes exceeding their applicable thresholds. Alternatively, it may be desirable to perform detection in Range 1 to differentiate between a sensor that has detected a MNP that transitions between being ferromagnetic and paramagnetic and a sensor that is not near any molecules being detected (or that does not have any molecules to be detected in its vicinity). For example, in a DNA sequencing application, the results obtained in Range 1 can be used to determine whether a particular magnetic sensor is in the vicinity of a DNA strand being sequenced. Because all of the MNPs emit magnetic fields in Range 1, if a particular sensor does not detect a magnetic field having a magnitude exceeding one of the thresholds in Range 1, it can be concluded that there is no DNA strand being sequenced in the region detectable by the particular sensor.

After some or all magnetic sensors have been read in each of the temperature ranges, the MNPs may be cleaved from the incorporated magnetically-labeled nucleotide precursor using, for example, enzymatic or chemical cleavage, as is known in the art. The process can then be repeated for the next unpaired base in the strand being sequenced. For at least DNA sequencing applications, this embodiment allows for a single chemistry step per base read.

Thus, some embodiments herein that are suitable for DNA sequencing applications are directed to a method of introducing all four nucleotide precursors, each labeled by a different MNP type, into a detection device fluidic channel (e.g., a flow cell array of magnetic sensors, described in more detail below) simultaneously or approximately simultaneously to enable a single template DNA base read. MNP types suitable for such embodiments become paramagnetic at the temperatures used for the chemistries that functionalize the nucleotide precursors (typically 80-100 degrees Celsius), and have different thermal stabilities so that they can be distinguished from each other. As explained above, the use of such MNP types allows the use of a single chemistry cycle per base read, which can significantly increase the sequencing data collection throughput and decrease the amount of time needed to sequence a genome.

TABLE A

| | Magnetic field magnitude emitted as a function of temperature (T) | | | | Base |
|---|---|---|---|---|---|
| MNP type | Range 1: $T < T_{c,1}$ | Range 2: $T_{c,1} < T < T_{c,2}$ | Range 3: $T_{c,2} < T < T_{c,3}$ | Range 4: $T_{c,3} < T < T_{c,4}$ | (Precursor) |
| 4 | >=Th4 | >=Th4 | >=Th4 | >=Th4 | T |
| 3 | >=Th3 | >=Th3 | >=Th3 | <Th3 | G |
| 2 | >=Th2 | >=Th2 | <Th2 | <Th2 | C |
| 1 | >=Th1 | <Th1 | <Th1 | <Th1 | A |

In some embodiments, the four nucleotide precursors are introduced into the fluidic channel substantially simultaneously at a temperature exceeding the highest blocking or Curie temperature of the MNP types being used as magnetic labels. Under such conditions, all of the MNPs labeling nucleotide precursors are superparamagnetic or paramagnetic. This approach can mitigate (and, ideally, eliminate) magnetic interactions between the MNPs that might otherwise cause clumping or clustering of MNPs labeling different nucleotide precursors. In other words, as long as the magnetically-labeled nucleotide precursors are added to the fluidic channel at a temperature above the highest blocking temperature or Curie temperature, there will be little or no magnetic interaction between the MNPs when they are added to the fluidic channel(s), which avoids clumping or clustering of multiple MNPs that could otherwise complicate detection of the individual bases and/or hamper the incorporation of the introduced nucleotide precursors with the target DNA strands. The nucleotide precursors are given time to be incorporated into the target DNA strands (e.g., the polymerase incorporates whichever of the nucleotide precursors is a match for the next unpaired base of the DNA strand). The system may then be cooled to a lower temperature (e.g., room temperature) at which all of the introduced MNPs are ferromagnetic to begin the measurement (sequencing) cycle, which could involve any number of magnetic detection schemes, including those mentioned above.

In some embodiments, the chemistry step to cleave and flush MNPs from the fluidic channel is also performed at a temperature above the blocking temperature or Curie temperature, also to prevent clumping and magnetic interactions between MNPs being washed away.

Because the MNPs are ferromagnetic at the selected starting temperature (e.g., room temperature), any magnetic sensor configured to detect magnetic fields at a site where a nucleotide precursor was incorporated should detect a MNP, but the identity of the MNP likely cannot be determined. By increasing the temperature of the system above the Curie temperature of one of the MNP types, however, that MNP type can be made paramagnetic. Once paramagnetic, that MNP type will not generate a magnetic field, and it will no longer be detected by the magnetic sensor. Therefore, subsequent measurements made after increasing the system temperature first above the Curie temperature of MNP1, then MNP1 and 2, and finally MNP1, 2, and 3 will see more and more MNPs "drop out" and allow the sequencing system to distinguish which MNP, and therefore which base, was incorporated at a particular site in the array. A chemistry step can then be run to cleave and flush the MNPs, and the process can be repeated for the next unpaired base in the target DNA strand. Here, the number of chemistry steps required is reduced to speed up the read process, which is primarily limited only by local heating/cooling times in the fluidic channel(s).

It is to be understood that, as explained previously, the temperatures at which magnetic fields are detected need not be monotonically increasing. For example, once the magnetically-labeled nucleotide precursors have been added to the fluidic channel at a temperature above the highest Curie temperature of all of the MNPs being used, the temperature can be cooled to be below only that highest Curie temperature. In general, the temperature can be varied in any selected way to determine which, if any, MNP is being detected by a particular sensor.

Figure 2B:
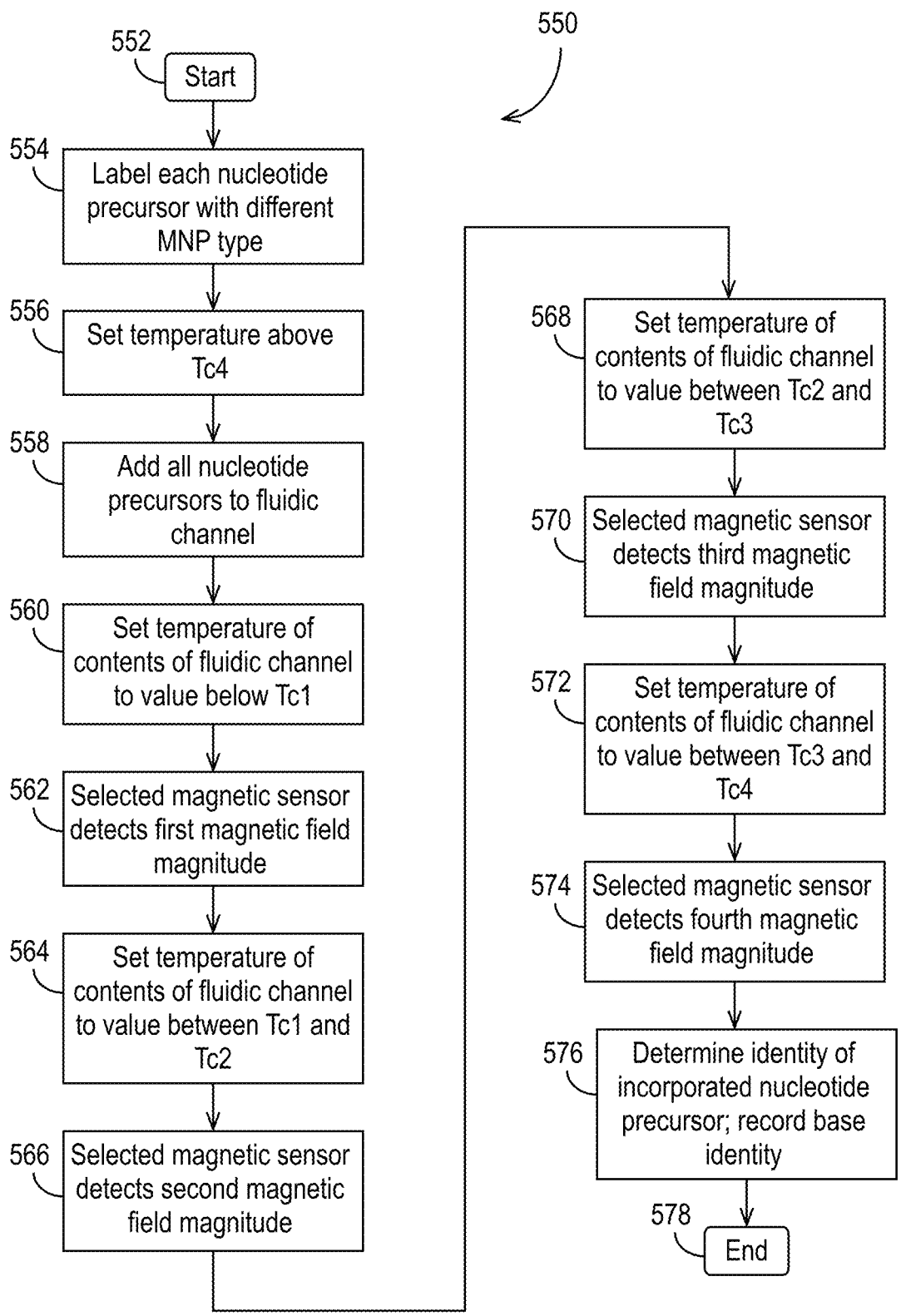
FIG. 2B illustrates an exemplary method suitable for DNA sequencing in accordance with some embodiments.

FIG. 2B illustrates an exemplary method 550 suitable for DNA sequencing in which all four magnetically-labeled nucleotide precursors are added to a fluidic channel of a detection device at the same (or substantially the same) time in accordance with some embodiments. FIG. 2B illustrates the exemplary method 550 assuming the Curie temperature is exploited, but it is to be appreciated that other characteristic temperatures at which the MNP magnetic properties change, such as the blocking temperature, may be used instead. At 552, the method begins. At 554, each nucleotide precursor is labeled by a different MNP type (e.g., A is labeled by MNP1, C by MNP2, G by MNP3, and T by MNP4, where MNP1, MNP2, MNP3, and MNP4 have distinguishable temperature-dependent thermal stabilities). For exemplary purposes, assume that the first MNP type ("MNP1") emits a magnetic field having a magnitude above a first threshold ("Th1") at temperatures below $T_{c,1}$ and below the first threshold at temperatures above $T_1$; the second MNP type ("MNP2") emits a magnetic field having a magnitude above a second threshold ("Th2") at temperatures below $T_{c,2}$ and below the second threshold at temperatures above $T_2$; the third MNP type ("MNP3") emits a magnetic field having a magnitude above a third threshold ("Th3") at temperatures below $T_{c,3}$ and below the third threshold at temperatures above $T_{c,3}$; and the fourth MNP type ("MNP4") emits a magnetic field having a magnitude above a fourth threshold ("Th4") at temperatures below $T_{c,4}$ and below the fourth threshold at temperatures above $T_{c,4}$. (Again, as explained above, the magnetization may change less abruptly about the Curie temperature than the step-like behavior assumed here, in which case "at temperatures below [the Curie temperature]" may be interpreted as "at temperatures below [the Curie temperature minus a suitable buffer]." Similarly, "at temperatures above [the Curie temperature]" may be interpreted as "at temperatures above [the Curie temperature plus a suitable buffer].")

At 556, the temperature of the mixture of magnetically-labeled nucleotide precursors (or the temperature of the fluidic channel of the detection device) is set to a value above the highest Curie temperature of the four MNP types. The temperature may be set, for example, using a temperature control device (e.g., a heater) to heat the contents of the fluidic channel. Alternatively or in addition, the nucleotide precursors may be heated (or cooled) prior to being added to the fluidic channel. With the assumptions set forth above, the highest Curie temperature is $T_{c,4}$. At this temperature, all of the MNPs labeling the nucleotide precursors are paramagnetic and are less likely to interact magnetically and cause clumping or clustering. At 558, all of the nucleotide precursors are added to the fluidic channel of the detection device (e.g., at the same time, at substantially the same time, or sequentially before step 560 begins). After some period of time during which the nucleotide precursors are given time to be incorporated into target DNA strands, at 560, the temperature of the fluidic channel is set to a value below the lowest Curie temperature, $T_1$. (Again, as explained above, the choice to detect first at a temperature below the lowest Curie temperature is arbitrary and is not a requirement.) At 562, each of a selected one or more magnetic sensors detects a first magnetic field magnitude in its vicinity (e.g., caused by MNPs within the fluidic channel). As explained above, the magnetic sensor(s) may sense the magnetic field emitted by one or more MNPs by detecting a resistance, a voltage, a current, a frequency, a noise, and/or a change in resistance, voltage, current, frequency, and/or noise. The sensed first magnetic field magnitude may be recorded.

At 564, the temperature of the contents of the fluidic channel is set to a value between the lowest Curie temperature, $T_1$, and the second-to-lowest Curie temperature, $T_2$. The temperature may be set, for example, using a temperature control device (e.g., a heater) to heat the contents of the fluidic channel. At 566, each of the selected one or more magnetic sensors detects a second magnetic field magnitude in its vicinity (e.g., caused by MNPs within the fluidic channel). The sensed second magnetic field magnitude may be recorded.

At 568, the temperature of the fluidic channel is set to a value between the second-to-lowest Curie temperature, $T_2$, and the second-to-highest Curie temperature, $T_{c,3}$. The temperature may be set, for example, using a temperature control device (e.g., a heater) to heat the contents of the fluidic channel. At 570, each of the selected one or more magnetic sensors detects a third magnetic field magnitude in its vicinity (e.g., caused by MNPs within the fluidic channel). The sensed third magnetic field magnitude may be recorded.

At 572, the temperature of the fluidic channel is set to a value between the second-to-highest Curie temperature, $T_{c,3}$, and the highest Curie temperature, $T_{c,4}$. The temperature may be set, for example, using a temperature control device (e.g., a heater) to heat the contents of the fluidic channel. At 574, each of the selected one or more magnetic sensors detects a fourth magnetic field magnitude in its vicinity (e.g., caused by MNPs within the fluidic channel). The sensed fourth magnetic field magnitude may be recorded.

At 576, the identity of the incorporated nucleotide precursor is determined based on an analysis of the first, second, third, and fourth magnetic field magnitudes. The analysis may be conducted using a logic table similar to Table A shown above. Once the identity of the incorporated nucleotide precursor has been determined, it or the identity of the complementary base may be recorded.

As explained above, it is to be understood that the order of certain of the steps shown in FIG. 2B can be modified. For example, although FIG. 2B shows the first temperature at which magnetic fields are detected as being below the lowest Curie temperature, it should be appreciated that the first temperature could be in any of the ranges defined by the Curie temperatures of the MNPs. Specifically, it may be convenient to set the first temperature to a value between $T_{c,3}$ and $T_{c,4}$ so that the temperature change between steps 556 and 560 is less than it would be if the first temperature were below $T_1$. Generally, temperature ranges may be tested in any order. Accordingly, it is to be understood the positions of steps 560 and 562, steps 564 and 566, steps 568 and 570, and steps 572 and 574 relative to each other may be modified (e.g., steps 560 and 562 can be before or after any or all of steps 564 and 566, steps 568 and 570, and steps 572 and 574).

Furthermore, it is to be understood that at step 556, the temperature of the mixture of magnetically-labeled nucleotide precursors (or the temperature of the fluidic channel of the detection device) may be set to a value above the highest blocking temperature of the four MNP types (which may be less than the highest Curie temperature of the four MNP types). At this temperature, all of the MNPs labeling the nucleotide precursors are superparamagnetic and are less likely to interact magnetically and cause clumping or clustering.

After some or all magnetic sensors have been read in each of the temperature ranges, the MNPs may be cleaved from the incorporated magnetically-labeled nucleotide precursors using, for example, enzymatic or chemical cleavage, as is known in the art. As explained above, the chemistry step to cleave and flush MNPs from the fluidic channel may be performed at a temperature above the highest blocking temperature or Curie temperature, also to prevent clumping and magnetic interactions between MNPs being washed away. A temperature control device (e.g., a heater) may be used to adjust the temperature of the contents of the fluidic channel prior to or during the washing step. The steps of the method 550 can then be repeated for the next unpaired base in the strand being sequenced. For at least DNA sequencing applications, this embodiment allows for a single chemistry step per base read.

Figure 3A:
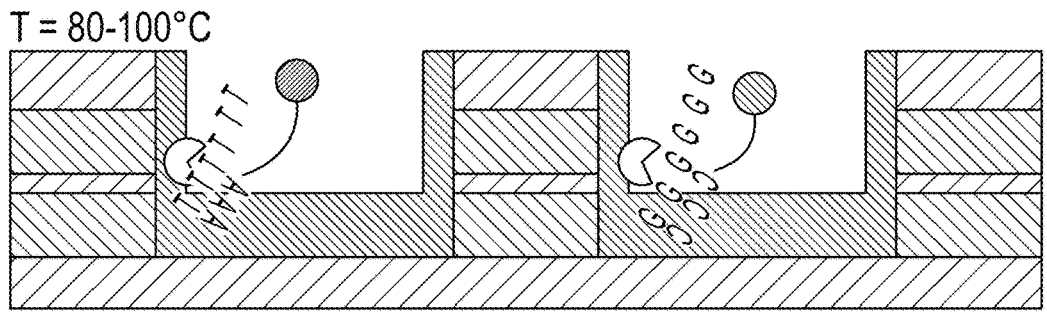
FIGS. 3A through 3E illustrate sequencing operations using different MNP types for nucleic acid sequencing in accordance with some embodiments.

As an example of the method 550, FIGS. 3A through 3E illustrate the sequencing operations using different MNP types for nucleic acid sequencing in accordance with some embodiments. FIG. 3A is a simplified illustration of two target DNA strands (templates) with polymerase bound to a fluidic channel of a sequencing device following incorporation of the MNP-labeled nucleotide precursors as described above. The labeled nucleotides that are complementary to the next unpaired bases in the target DNA strands are incorporated into the DNA strands. In FIG. 3A, an adenine (A) nucleotide precursor labeled by MNP1 has been incorporated in the DNA strand (fragment) at the site within the fluidic channel on the left-hand side of FIG. 3A, and a cytosine (C) nucleotide precursor labeled by MNP2 has been incorporated into the DNA strand (fragment) at the site on the right-hand side of FIG. 3A.

Figure 3B:
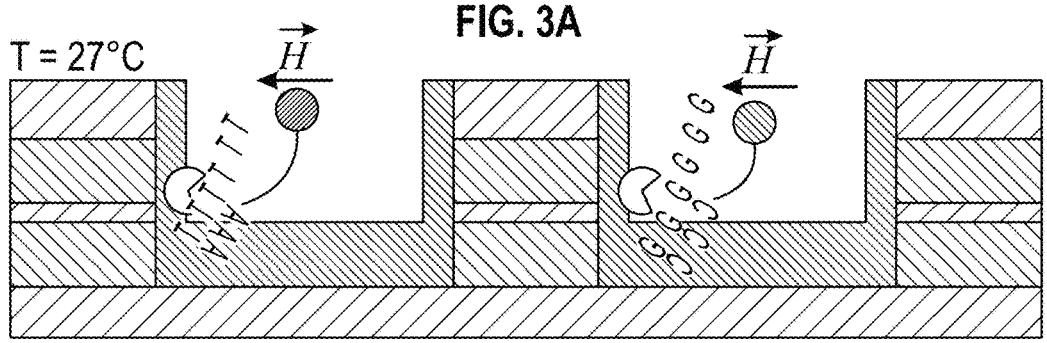

The system is then cooled, to a first temperature (for example, room temperature) to begin the sequencing cycle. As shown in FIG. 3B, assuming that the first temperature (shown as 27 degrees Celsius) is below the lowest Curie temperature of all of the MNP types, the MNPs labeling the incorporated nucleotide precursors emit magnetic fields (labeled by left-pointing arrows) having magnitudes that can be detected by magnetic sensors nearby.

Figure 3C:
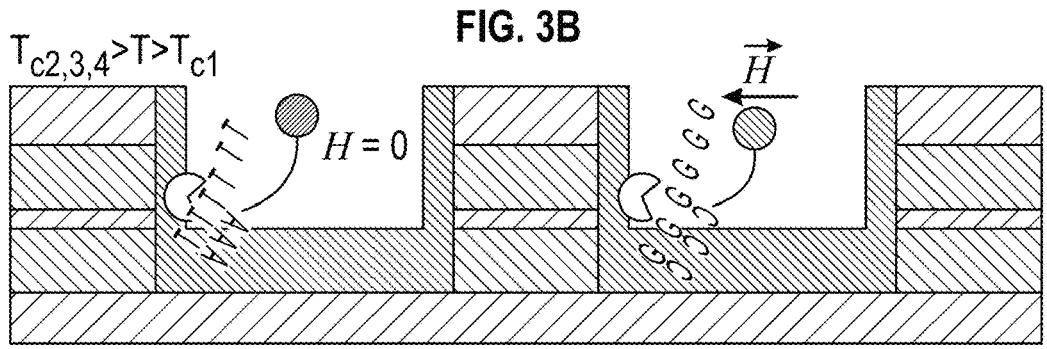

After detection at the first temperature is complete, the system is heated to a second temperature that is above the lowest Curie temperature of the four Curie temperatures but below the remaining three Curie temperatures. As shown in FIG. 3C, the MNP labeling the nucleotide precursor on the left-hand side of the drawing (MNP1) becomes paramagnetic and no longer generates a magnetic field above a first threshold. Assuming that the MNP labels adenine (A), it can be determined that magnetic sensors that detected a magnetic field magnitude above the first threshold at the first temperature but not at the second temperature detected A. Therefore, the last-paired base of the template DNA strand is the complementary base, T.

Figure 3D:
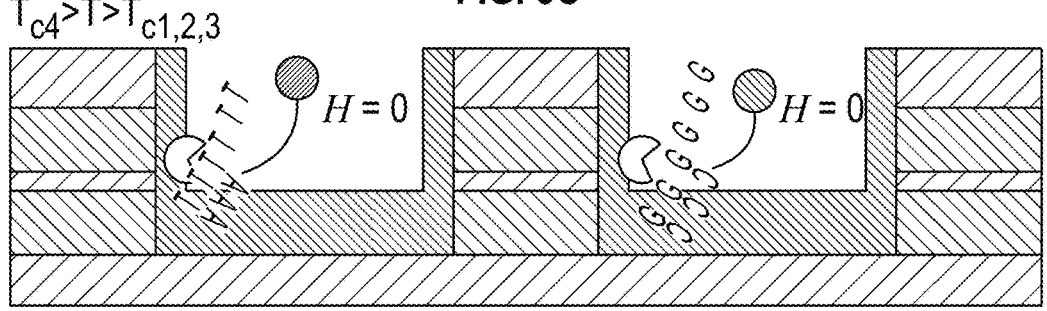
Figure 3E:
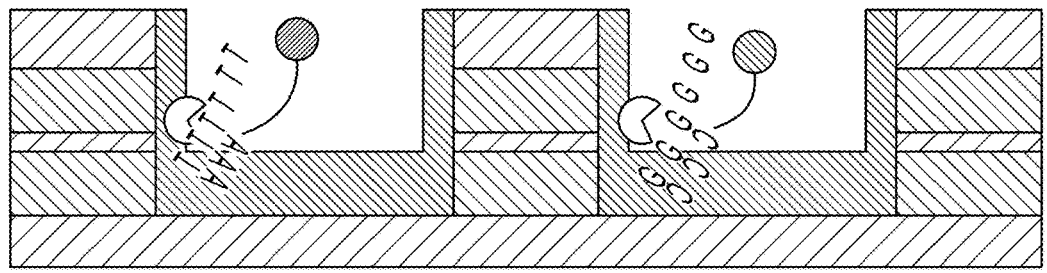

After detection at the second temperature is complete, the system is heated to a third temperature that is above the second-lowest Curie temperature of the four Curie temperatures but below the second-highest Curie temperature of the four Curie temperatures. As shown in FIG. 3D, the MNP labeling the nucleotide precursor incorporated into the DNA strand on the right-hand side of the drawing (MNP2) also becomes paramagnetic and no longer generates a magnetic field above a second threshold (which may be the same as or different from the first threshold used for the MNP types labeling other nucleotide precursors). Assuming the MNP labels cytosine (C), it can be determined that magnetic sensors that detected a magnetic field magnitude above the second threshold at the second temperature but not at the third temperature detected C. Therefore, it can be concluded that the last-paired base of the template DNA strand is the complementary base, G.

After detection at the third temperature is complete, the system is heated to a fourth temperature that is above all but the highest Curie temperature of the four Curie temperatures. At this temperature, MNP3 also becomes paramagnetic and no longer generates a magnetic field above a third threshold (which may be the same as or different from the first threshold used for MNP1 and/or the second threshold used for MNP2). Assuming MNP3 labels guanine (G), it can be determined that magnetic sensors that detected a magnetic field magnitude above the second threshold at the second temperature but not at the third temperature detected G. Therefore, it can be concluded that the last-paired base of the template DNA strand is the complementary base, C.

Following detection at the fourth temperature, the MNPs may be cleaved from the incorporated nucleotides and flushed out of the fluidic channel(s) in a chemistry step, which may, but is not required to, be performed at a temperature above the highest blocking temperature or Curie temperature to prevent clumping and magnetic interactions between MNPs being washed away. The process can then be repeated to identify the next unpaired bases in the target DNA strands. The system temperature can be raised to a temperature greater than the highest Curie or blocking temperature of the four MNPs, new samples of the labeled nucleotide precursors can be introduced, and the next sequencing cycle can begin. In embodiments such as the one illustrated in FIGS. 3A through 3E, the number of chemistry steps used is reduced to speed up the read process. The time required for each sequencing cycle is dependent on the heating/cooling time of the contents of the fluidic channel.

Although FIGS. 3A through 3E illustrate an exemplary DNA sequencing embodiment in which a single chemistry step enables detection of all four bases in a single step, as previously described, in other embodiments, a similar process may be performed using one type of MNP (or fewer than four MNP types) and introducing and detecting fewer than all bases at a time. For example, when a single MNP type is used, each individual base (nucleotide precursor) can be introduced and detected sequentially, one at a time. In such embodiments, detection may be accomplished in a binary manner, where the magnetic sensors detect whether or not there is a magnetic field magnitude indicative of the presence of the MNP type in the proximities of the magnetic sensors. This method may then be repeated for the remaining bases before cleaving/washing away the MNPs and repeating the process for the next unpaired base.

It is to be understood that it is not necessary to use four MNPs to perform detection using a single chemistry step. For example, in some DNA sequencing embodiments, one of the bases may be left unlabeled. Using the example above, and assuming that thymine (T) is left unlabeled, the table becomes Table B below:

TABLE B

| | Magnetic field magnitude emitted as a function of temperature (T) | | | | Base |
|---|---|---|---|---|---|
| MNP type | Range 1: $T < T_{C,1}$ | Range 2: $T_{c,1} < T < T_{c,2}$ | Range 3: $T_{c,2} < T < T_{c,3}$ | Range 4: $T > T_{c,3}$ | (Precursor) |
| None | ~0 | ~0 | ~0 | ~0 | T |
| 3 | >=Th3 | >=Th3 | >=Th3 | <Th3 | G |
| 2 | >=Th2 | >=Th2 | <Th2 | <Th2 | C |
| 1 | >=Th1 | <Th1 | <Th1 | <Th1 | A |

Relative to the example above, detection of the incorporation of A, C, and G is done as previously described, but the incorporation of T is detected by detecting the absence of a magnetic field in the vicinity of a magnetic sensor in each of the four temperature ranges. Optionally, a tolerance can be used to create the detection range for the unlabeled base to account for variations in stray magnetic fields in the vicinity of a magnetic sensor that is not near any MNP. Thus, if a magnetic field magnitude larger than each of the thresholds is not detected in any of the temperature ranges, the absence of detectable magnetic field (or detection of only a minimal magnetic field magnitude below what would be expected to be emitted by a MNP in the temperature range) can be interpreted as an indication that the last-incorporated nucleotide precursor is thymine (and, therefore, that the last-paired base in the DNA strand being sequenced is the complement to thymine, which is adenine (A)).

In embodiments in which three nucleotide precursors are labeled by different MNP types, each different MNP type having a different Curie temperature, and the fourth nucleotide precursor is left unlabeled, detection in the temperature range above the highest Curie temperature of the MNPs (Range 4 in the table above) may be skipped because, as shown in the table above, all of the three MNP types fail to emit magnetic fields having magnitudes exceeding their applicable thresholds, and the unlabeled nucleotide precursor also fails to emit a magnetic field. If Range 4 is skipped, it is possible to differentiate between a magnetic sensor that is not near any molecules being detected and a sensor that has detected the unlabeled nucleotide precursor (e.g., thymine in this example) during a particular sequencing cycle by comparing the results over a number of sequencing cycles. For example, in a DNA sequencing application, if, after some number of sequencing cycles (e.g., a number exceeding the maximum expected number of identical bases in a row for the DNA sample being sequenced) and in all of the temperature ranges, a particular sensor never detects a magnetic field having a magnitude exceeding one of the thresholds, it can be concluded that there is no DNA strand being sequenced in the region/area detectable by the particular sensor. But if a particular sensor sometimes detects a magnetic field having a magnitude that exceeds one of the thresholds in one or more of the temperature ranges (e.g., Ranges 1, 2, and 3), it can be concluded that in sequencing cycles in which the sensor does not detect a magnetic field with a magnitude exceeding any of the thresholds in any of the temperature ranges, thymine (T) was incorporated during the corresponding sequencing cycle.

After some or all magnetic sensors have been read in each of the temperature ranges, the MNPs may be cleaved from the incorporated magnetically-labeled nucleotide precursor using, for example, enzymatic or chemical cleavage, as is known in the art. The process can then be repeated for the next unpaired base in the strand being sequenced. For at least DNA sequencing applications, this embodiment allows for a single chemistry step per base read.

Figure 4:
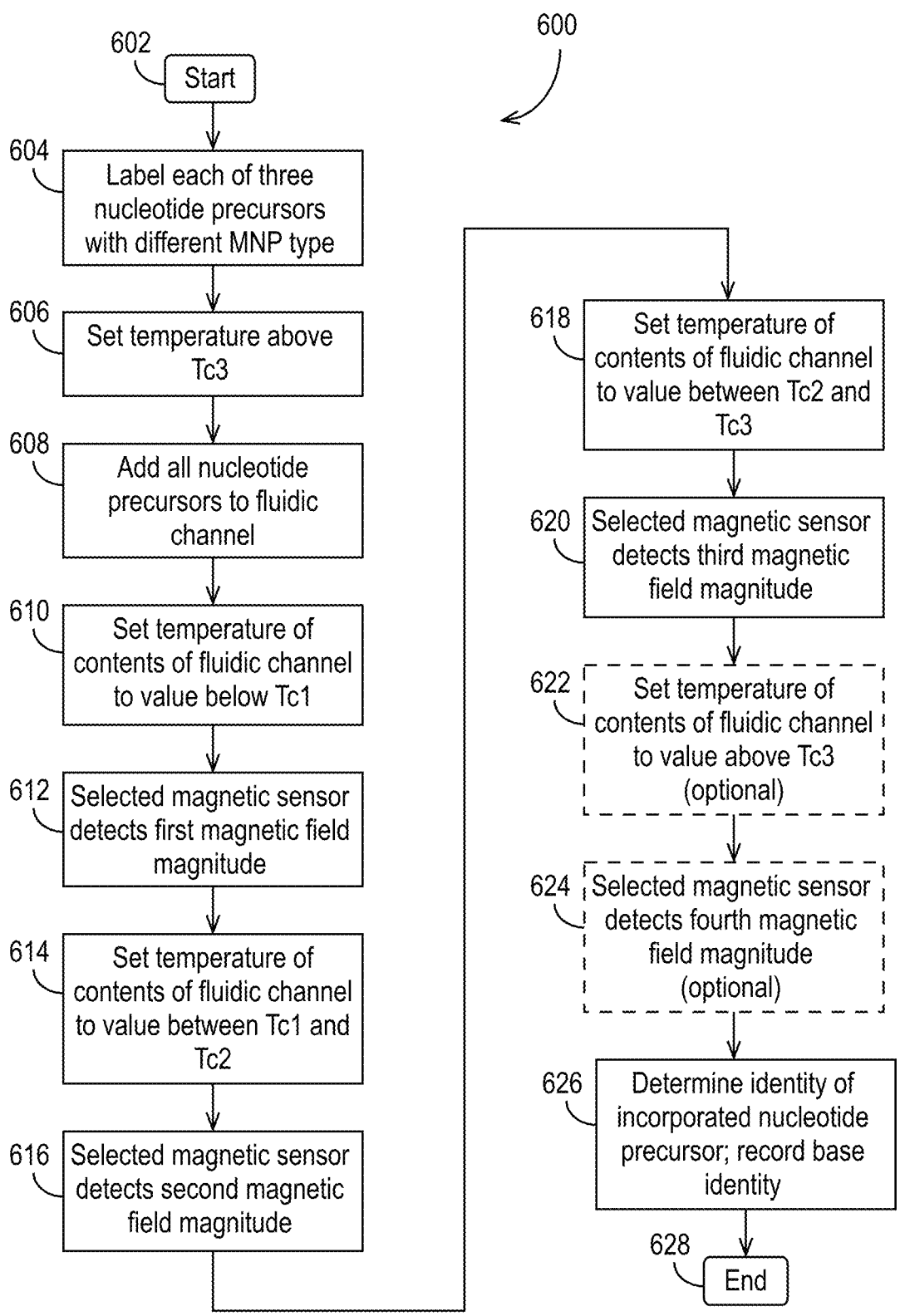
FIG. 4 illustrates another exemplary method suitable for DNA sequencing in accordance with some embodiments.

FIG. 4 illustrates an exemplary method 600 suitable for DNA sequencing in which three of the four nucleotide precursors are magnetically labeled and added to a fluidic channel of a detection device at the same (or substantially the same) time as a fourth, unlabeled nucleotide precursor in accordance with some embodiments. At 602, the method begins. At 604, each of three of the four nucleotide precursors is labeled by a different MNP type (e.g., A is labeled by MNP1, C by MNP2, and G by MNP3, where MNP1, MNP2, and MNP3 have distinguishable thermal stabilities). The fourth nucleotide precursor (e.g., T) is left unlabeled. For exemplary purposes, assume that the first MNP type ("MNP1") emits a magnetic field having a magnitude above a first threshold ("Th1") at temperatures below $T_{c,1}$ and below the first threshold at temperatures above $T_1$; the second MNP type ("MNP2") emits a magnetic field having a magnitude above a second threshold ("Th2") at temperatures below $T_{c,2}$ and below the second threshold at temperatures above $T_2$; and the third MNP type ("MNP3") emits a magnetic field having a magnitude above a third threshold ("Th3") at temperatures below $T_{c,3}$ and below the third threshold at temperatures above $T_{c,3}$.

At 606, the temperature of the mixture of nucleotide precursors (or the temperature of the fluidic channel of the detection device) is set to a value above the highest Curie temperature (or above the highest blocking temperature). With the assumptions set forth above, the highest Curie temperature is $T_{c,3}$. At this temperature, all of the MNPs labeling the nucleotide precursors are paramagnetic (or superparamagnetic) and are less likely to interact magnetically and cause clumping or clustering. At 608, all of the nucleotide precursors are added to the fluidic channel of the detection device (e.g., at the same time, at substantially the same time, or sequentially before step 410 begins). At 610, the temperature of the fluidic channel is set to a value below the lowest Curie temperature, $T_1$. At 612, each of a selected one or more magnetic sensors detects a first magnetic field magnitude in its vicinity (e.g., caused by MNPs within the fluidic channel). As explained above, the magnetic sensor(s) may sense the magnetic field emitted by one or more MNPs by detecting a resistance, a voltage, a current, a frequency, a noise, and/or a change in resistance, voltage, current, frequency, and/or noise. The sensed first magnetic field magnitude may be recorded.

At 614, the temperature of the fluidic channel is set to a value between the lowest Curie temperature, $T_1$, and the middle Curie temperature, $T_2$. At 616, each of the selected one or more magnetic sensors detects a second magnetic field magnitude in its vicinity (e.g., caused by MNPs within the fluidic channel). The sensed second magnetic field magnitude may be recorded.

At 618, the temperature of the fluidic channel is set to a value between the middle Curie temperature, $T_2$ and the highest Curie temperature, $T_{c,3}$. At 620, each of the selected one or more magnetic sensors detects a third magnetic field magnitude in its vicinity (e.g., caused by MNPs within the fluidic channel). The sensed third magnetic field magnitude may be recorded.

Optionally, at 622, the temperature of the fluidic channel is set to a value above the highest Curie temperature, $T_{c,3}$. Optionally, at 624, each of the selected one or more magnetic sensors detects a fourth magnetic field magnitude in its vicinity, which should be near zero because all of the MNPs added to the fluidic channel should be paramagnetic at temperatures above the highest Curie temperature. If steps 622 and 624 are performed, the sensed fourth magnetic field magnitude may be recorded.

At 626, the identity of the incorporated nucleotide precursor is determined based on an analysis of the first, second, third, and (if detected) fourth magnetic field magnitudes. The analysis may be conducted using a logic table similar to Table B shown above. Once the identity of the incorporated nucleotide precursor has been determined, it or the identity of the complementary base may be recorded.

It is to be understood that the order of certain of the steps shown in FIG. 4 can be modified. For example, although FIG. 4 shows the first temperature at which magnetic fields are detected as being below the lowest Curie temperature, it should be appreciated that the first temperature could be in any of the ranges defined by the Curie temperatures of the MNPs. Specifically, it may be convenient to set the first temperature to a value between $T_{c,2}$ and $T_{c,3}$ so that the temperature change between steps 606 and 610 is less than it would be if the first temperature were below $T_1$. Generally, temperature ranges may be tested in any order. Accordingly, it is to be understood the positions of steps 610 and 612, steps 614 and 616, steps 618 and 620, and (if performed) steps 622 and 624 relative to each other may be modified (e.g., steps 610 and 612 can be before or after any or all of steps 614 and 616, steps 618 and 620, and (if performed) steps 622 and 624).

After some or all magnetic sensors have been read in each of the temperature ranges, the MNPs may be cleaved from the incorporated magnetically-labeled nucleotide precursors using, for example, enzymatic or chemical cleavage, as is known in the art. The steps of the method 600 can then be repeated for the next unpaired base in the strand being sequenced. For at least DNA sequencing applications, this embodiment allows for a single chemistry step per base read.

Magnetic Sensors

Figure 5A:
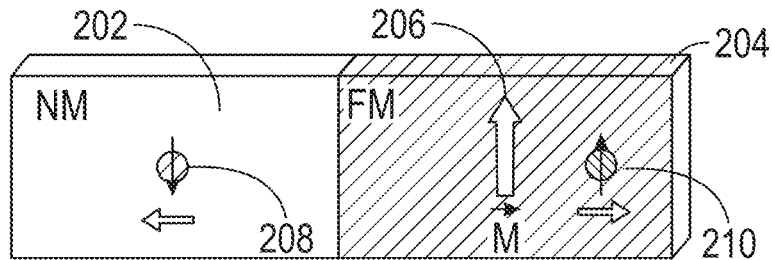
FIGS. 5A, 5B, and 5C illustrate the basic construction of a magnetoresistive (MR) device and how it can be used as a magnetic sensor in accordance with some embodiments.

The magnetic sensors used in embodiments described herein may be or comprise, for example, magnetoresistive (MR) sensors that exploit MR principles. To understand how a MR device works, consider how an electron in an electric current interacts with a thin film ferromagnetic (FM) layer. Quantum mechanics dictate that the probability is high that an electron interacting with the FM layer will cause the electron spin to be oriented preferentially parallel or antiparallel to the direction of the magnet's moment for transmitted and reflected electrons respectively, as shown in FIG. 5A. Electrons with spin parallel to the moment of the FM layer 204 preferentially pass through the FM layer 204 (spin 210), whereas those with spin antiparallel preferentially are reflected back (spin 208). Due to this phenomenon, the interface between a nonmagnetic (NM) layer 202 (assumed for purposes of this explanation to be a metal layer) and a FM layer 204 acts as a spin filter that can act to spin polarize (i.e., make one spin direction more preferential) an incoming electric current.

Figure 5B:
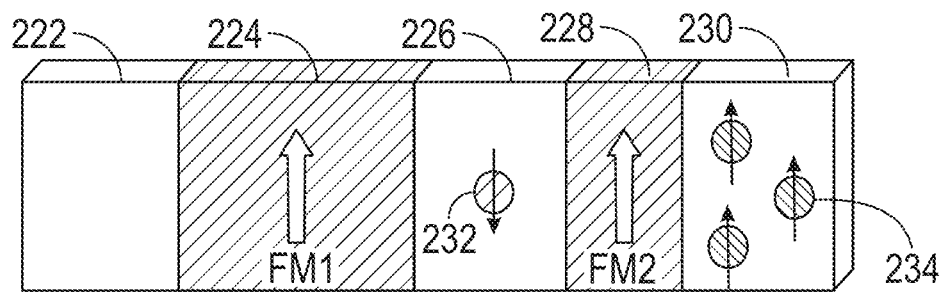
Figure 5C:
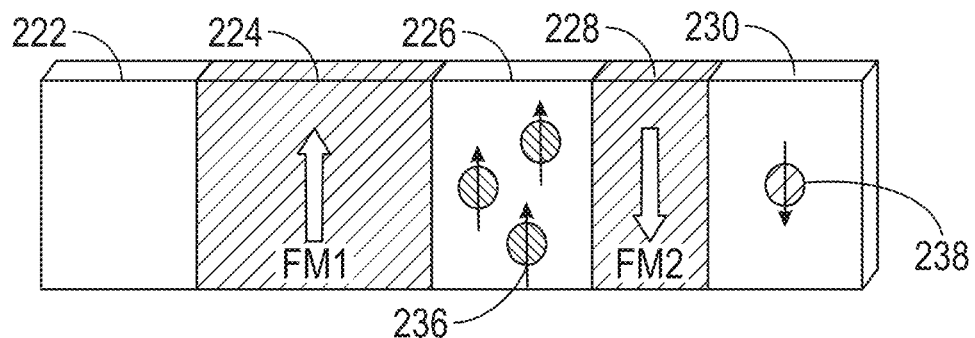

For a device with two FM layers 224 and 228 separated by a nonmagnetic metal layer 226 (spacer layer) as shown in FIGS. 5B and 5C, an incoming electric current spin polarized by the first FM layer (FM1) 224 interacts differently with the second FM layer (FM2) 228, depending on the orientation of that layer's magnetic moment. If the moments of both FM layers 224 and 228 are parallel to one another (FIG. 5B), then many electrons will pass through the device because many electrons in the current will have their spin oriented with the moment of the second FM 228 (spin 234). Few electrons will be reflected back (spin 232).

In the opposite case, where the moments of the two FM layers 224 and 228 are oriented in an anti-parallel fashion (FIG. 5C), many electrons will be blocked from passing through the second FM layer 228 (spin 236), and far fewer electrons will traverse the device (spin 238). This means the amount of current passing through the device is dependent on the orientation of the two FM layers 224 and 228 with respect to one another. Because the resistance of the device is proportional to the current, the resistance of the device is dependent on the orientation of the moments (i.e., the resistance is smaller when the moments are parallel than it is when they are antiparallel).

Whereas the above description presumes use of a non-magnetic metal spacer layer 226 separating the two FM layers 224 and 228 (a configuration also known as a spin valve (SV) or giant magnetoresistance (GMR) device), an insulating layer known as a tunneling barrier can alternatively be used as the spacer layer separating the FM layers. In such implementations, the spacer layer may be made of a nitride or oxide-based material. These types of devices are called magnetic tunnel junctions (MTJs), and they exhibit a similar resistance response (referred to as tunnel magnetoresistance or TMR) because of spin polarized tunneling as opposed to spin filtering.

MR devices have been used in many applications, including magnetic recording, magnetic field sensing, and magnetic memory. In these cases, it is usually preferable to design the MR device to have one FM layer be effectively "pinned" so that the direction in which its moment points in stays fixed and is not easily altered by the application of a magnetic field. This is usually achieved by placing an antiferromagnetic (AFM) layer adjacent to the pinned layer and using an effect called exchange coupling that provides strong unidirectional anisotropy for the FM layer's moment. The second FM layer is left "free" to rotate under the impulse of a magnetic field such that its moment rotates with respect to the fixed orientation of the pinned FM layer so that the resistance of the device becomes a detector of the magnetic field direction or amplitude by effectively acting as a magnetic-field-to-voltage transducer.

Magnetoresistance can be defined as $$MR = R_0 + \Delta R \sin^2\left(\frac{\theta}{2}\right),$$

where $R_0$ is the resistance of the device when the moments are oriented in a parallel configuration, $\Delta R$ is the difference between resistance in parallel and antiparallel orientations, and $\theta$ is the angle between the two moments. For magnetic field sensing applications, a linear response to the magnetic field is desired from the sensor. Considering the equation above, the sensor should ideally be designed and fabricated to have the two FM layers oriented approximately 90° with respect to one another. This may be achieved by exchange biasing the pinned layer with an antiferromagnet and using a "hard bias" coating to rotate the free layer approximately 90° away from the pinned layer. Further detail on this design, as applied to embodiments related to sequencing applications, will be given below.

Figure 6:
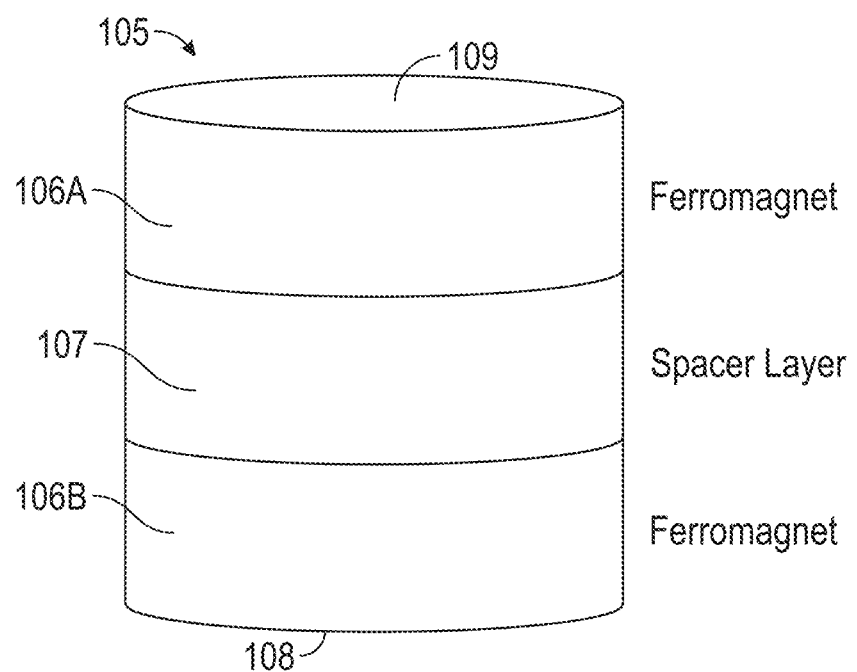
FIG. 6 illustrates a portion of a magnetic sensor in accordance with some embodiments.

FIG. 6 illustrates a portion of a magnetic sensor 105 in accordance with some embodiments. The exemplary magnetic sensor 105 of FIG. 6 has a bottom 108 and a top 109 and comprises three layers, e.g., two ferromagnetic layers 106A, 106B separated by a nonmagnetic spacer layer 107. The nonmagnetic spacer layer 107 may be, for example, a metallic material or combination of metallic materials, such as, for example, copper or silver, in which case the structure is called a spin valve (SV), or it may be an insulator such as, for example, alumina or magnesium oxide, in which case the structure is referred to as a magnetic tunnel junction (MTJ). Suitable materials for use in the ferromagnetic layers 106A, 106B include, for example, alloys of Co, Ni, and Fe (sometimes mixed with other elements). The example materials described above are merely exemplary and are not intended to be limiting. Materials suitable for use in MTJs are known to those having ordinary skill in the art.

In some embodiments, the magnetic sensor 105 is a thin-film device, and the ferromagnetic layers 106A, 106B are engineered to have their magnetic moments oriented either substantially in the plane of the film or substantially perpendicular to the plane of the film. Additional materials may be deposited below and/or above the three layers 106A, 106B, and 107 shown in FIG. 6 to serve purposes such as interface smoothing, texturing, and protection from processing used to pattern a detection device (described below), but the active region of the magnetic sensor 105 lies in the trilayer structure shown in FIG. 6. Thus, a component that is in contact with a magnetic sensor 105 may be in contact with one of the three illustrated layers 106A, 106B, or 107, or it may be in contact with another part of the magnetic sensor 105 that is not illustrated in FIG. 6.

Figure 7A:
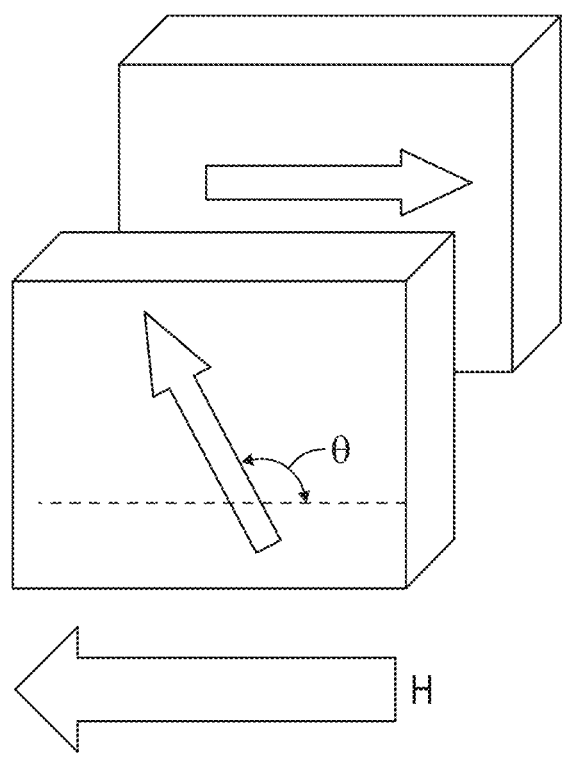
FIGS. 7A and 7B illustrate the resistance of MR sensors suitable for use in accordance with some embodiments.
Figure 7B:
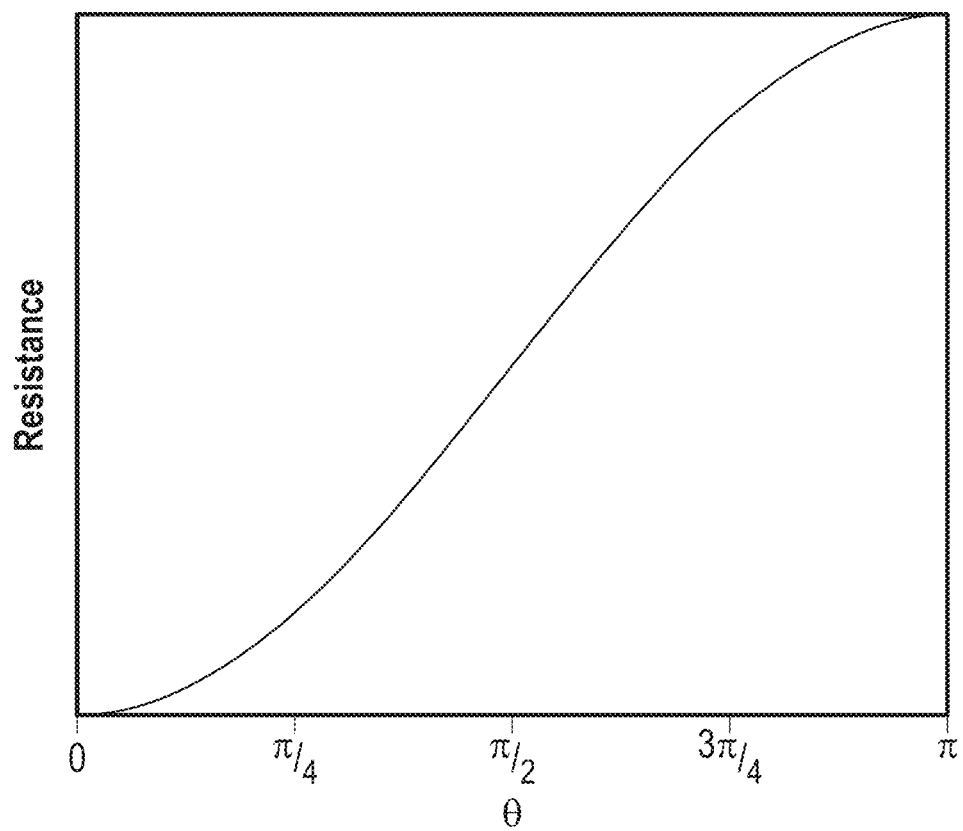

FIGS. 7A and 7B illustrate the resistance of MR sensors, which is proportional to $1-\cos(\theta)$, where $\theta$ is the angle between the moments of the two ferromagnetic layers 106A, 106B shown in FIG. 6. To maximize the signal generated by a magnetic field and provide a linear response of the magnetic sensor 105 to an applied magnetic field, the magnetic sensors 105 may be designed such that the moments of the two ferromagnetic layers 106A, 106B are oriented n/2 or 90 degrees with respect to one another in the absence of a magnetic field. This orientation can be achieved by any number of methods that are known in the art. As discussed above, one solution is to use an antiferromagnet to "pin" the magnetization direction of one of the ferromagnetic layers (either 106A or 106B, designated as "FM1") through an effect called exchange biasing and then coat the sensor with a bilayer that has an insulating layer and permanent magnet. The insulating layer avoids electrical shorting of the magnetic sensor 105, and the permanent magnet supplies a "hard bias" magnetic field perpendicular to the pinned direction of FM1 that will then rotate the second ferromagnet (either 106B or 106A, designated as "FM2") and produce the desired configuration. Magnetic fields parallel to FM1 then rotate FM2 about this 90 degree configuration, and the change in resistance results in a voltage signal that can be calibrated to measure the field acting upon the magnetic sensor 105. In this manner, the magnetic sensor 105 acts as a magnetic-field-to-voltage transducer.

Note that although the example discussed immediately above described the use of ferromagnets that have their moments oriented in the plane of the film at 90 degrees with respect to one another, a perpendicular configuration can alternatively be achieved by orienting the moment of one of the ferromagnetic layers 106A, 106B substantially out of the plane of the film, which may be accomplished using what is referred to as perpendicular magnetic anisotropy (PMA).

Accordingly, the magnetic sensors can have any of a number of configurations. For example, each of the magnetic sensors used in embodiments herein may be a thin-film device that uses the MR effect (e.g., it may be a MR sensor) to detect MNPs in a fluidic channel of a detection device (e.g., a DNA sequencing apparatus). Each magnetic sensor may operate as a potentiometer with a resistance that varies as the strength and/or direction of the sensed magnetic field changes. Each magnetic sensor may have dimensions of less than about 30 nm to detect magnetic fields on the order of a few millitesla (mT).

It is to be understood that although much of this disclosure focuses on the use of the resistance of magnetic sensors as a proxy for the magnetic field magnitude, the output provided by the magnetic sensors may be any suitable output, including, for example, a resistance, a voltage, a current, a frequency, a noise, and/or a change in resistance, voltage, current, frequency, and/or noise.

MR Sensor Array

FIGS. 8A through 8C illustrate an embodiment of a cross-point array architecture 300 that may be included in the detection device 100 in accordance with some embodiments. For illustration, the magnetic sensors 105 illustrated in FIGS. 8A through 8C comprise MTJ elements 308, but it is to be appreciated that other types of sensors (e.g., spin valve devices) may be used. It is to be appreciated that although various particular MR sensor types were described above, the description is not intended to exclude other MR sensor types.

Referring to FIG. 8A, the cross-point array architecture 300 includes top wires 318 and bottom wires 320. As shown in the exemplary embodiment of FIG. 8A, the top wires 318 are oriented at substantially 90° angles to the bottom wires 320 as shown. An example MTJ element 308 is situated between a crossing of the array. The example MTJ element 308 includes two or more FM layers separated by one or more non-magnetic layers 316 (e.g., MgO). As shown, one of the FM layers is a free layer 310 that will rotate in the presence of a magnetic field, and another of the FM layers is a pinned (or fixed) layer 314 that may be a single FM coupled to an AFM layer 312. Alternatively, a compound structure called a synthetic antiferromagnet (SAF) may be used. The SAF includes two FM layers separated by a magnetic coupling layer (e.g., ruthenium), with one of the two FM layers coupled to an AFM layer. It is to be understood that although the example layer arrangement of MTJ element 308 shows a general structure with layers over or under other layers, intervening layers not shown can be inserted.

To illustrate some of the features of the cross-point array architecture 300, FIG. 8B shows a cross-section of the cross-point array architecture 300 along the top wire 318 direction (indicated in FIG. 8A by the dash-dot line labeled "8B"), and FIG. 8C shows a cross-section of the cross-point array architecture 300 along the bottom wire 320 direction (indicated in FIG. 8A by the dashed line labeled "8C"). As shown, the sides of the MTJ elements 308 (which may be the magnetic sensors 105) are encapsulated by insulating material 336. Optionally, as shown in FIG. 8B, a hard bias magnetic material 338 may also be deposited between the MTJ elements 308. If present, the hard bias magnetic material 338 may be magnetized to point in a direction parallel to the direction of the top wire(s) 318. In embodiments including hard bias magnetic material 338, a thin layer of insulator 340 is also deposited on top of the hard bias magnetic material 338 to electrically insulate it from the top wire(s) 318.

In some embodiments, the orientation of the free layer 310 moment is at an angle approximately 90° from the pinned layer 314 moment (as shown in the left side panel of FIG. 13A, discussed further below), which can be achieved using one or more strategies. The first is by using a hard bias field in which the hard bias magnetized along the direction of the top magnet also applies a magnetic field across the MTJ elements 308 in the direction of the top wire 318. Because the pinned layer 314 is fixed using an AFM layer 312, its moment can be chosen to be perpendicular to the hard bias field, but the free layer 310 will rotate to be roughly parallel to the hard bias field.

A second way to achieve this orientation configuration is to pattern the MTJ elements 308 into rectangles or ellipses, where the long axis of the MTJ elements 308 is along the direction of the top wire(s) 318. Through the aspect ratio of these shapes, a shape anisotropy energy can be tuned, which creates an axis along the length of the top wire(s) 318 along which the free layer 310 magnetization will preferentially point in the absence of an external magnetic field.

A third way to achieve this orientation configuration is by etching the FM layers 310, 314 along an axis to induce texturing (see, e.g., U.S. Pat. No. 7,382,586), which can also create uniaxial anisotropy so that the free layer 310 moment will point along the length of the top wire(s) 318.

A fourth way to achieve this orientation configuration is to use perpendicular magnetic anisotropy to pull the free layer 310 out of plane while keeping the pinned layer 314 in the plane of the film, or vice versa. The anisotropy of the free layer 310 is kept small enough that a small in-plane field can rotate the free layer 310 in plane, which is qualitatively similar to the other methods described above. There are other methods to achieve a 90° orientation between the free and pinned layer moments in addition to those mentioned here, and achieving this orientation is not limited to these options.

Referring to FIG. 8C, the cross section shows the fluidic channels 115 (e.g., nanofluidic or microfluidic channels), which may be, for example, trenches etched in an insulator. As shown, a small amount of insulator 322 is left on the sidewalls of the magnetic sensors 105 (illustrated as MTJ elements 308) so that the MNPs do not electrically interact with the magnetic sensors 105. The portion of the insulator exposed to (and forming) the fluidic channel 115 may form the wall 117 to which polymerase molecules or molecules to be detected (e.g., nucleic acid samples) may be attached for sequencing.

Detection Devices

Figure 9A:
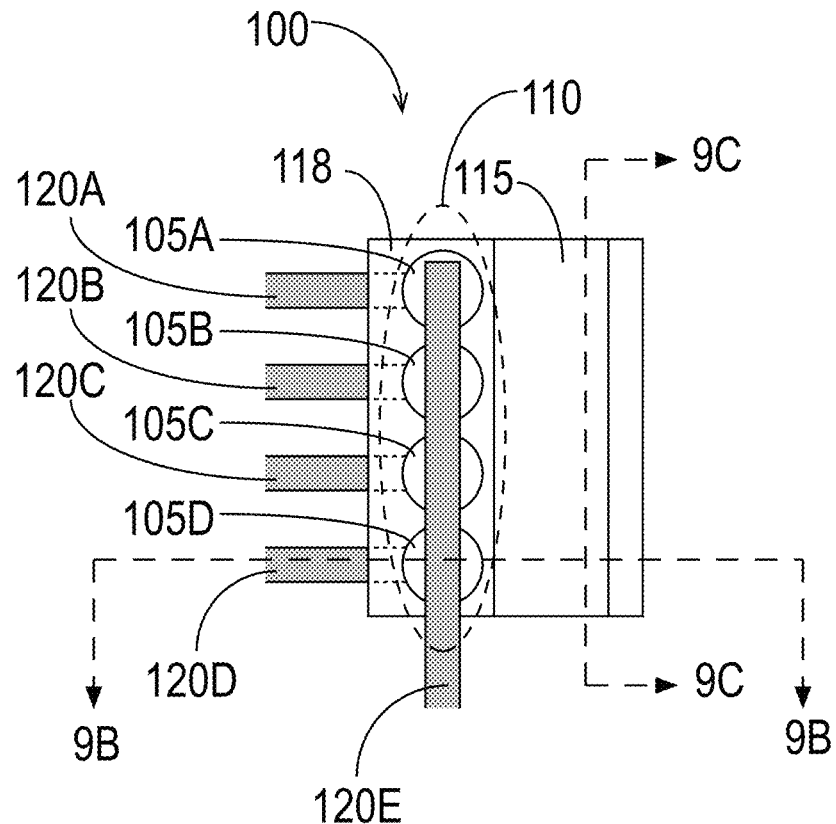
FIGS. 9A, 9B, and 9C illustrate an exemplary detection device in accordance with some embodiments.
Figure 9B:
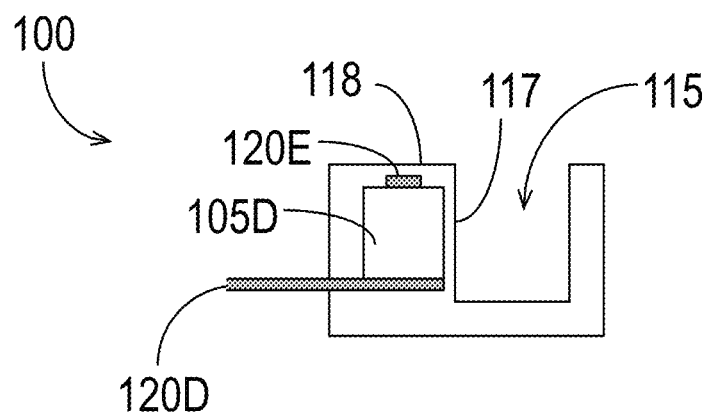
Figure 9C:
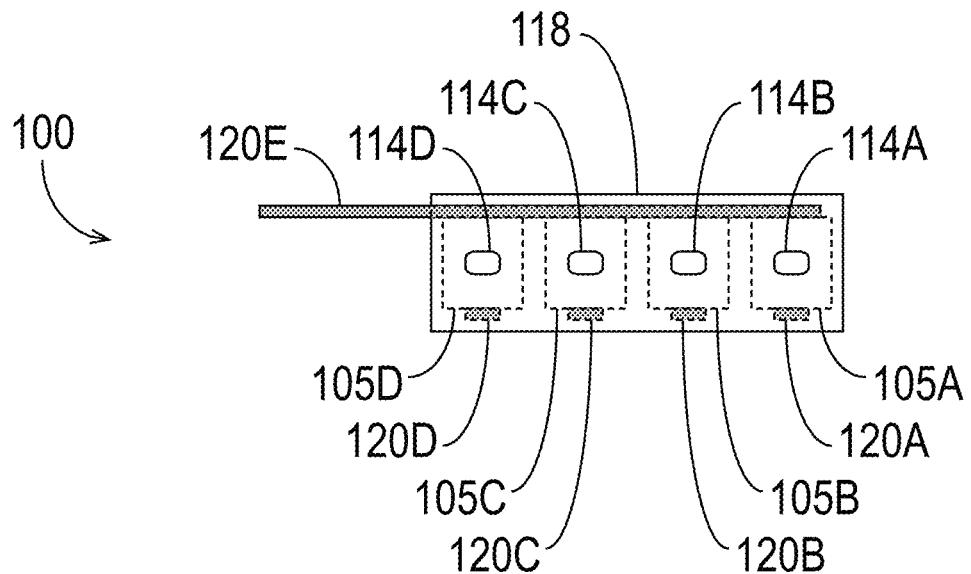

FIGS. 9A, 9B, and 9C illustrate an exemplary detection device 100 in accordance with some embodiments. The exemplary detection device 100, which is suitable for use with the methods described above, includes a plurality of magnetic sensors 105 arranged in an array 110 disposed adjacent to a fluidic channel 115. FIG. 9A is a top view of the apparatus, FIG. 9B is a cross-section view at the position indicated by the dashed line labeled "9B" in FIG. 9A, and FIG. 9C is another cross-section view at the position indicated by the dashed line labeled "9C" in FIG. 9A. Exemplary embodiments of the magnetic sensors 105 were described above.

As shown in FIGS. 9A, 9B, and 9C, the exemplary detection device 100 comprises a magnetic sensor array 110 that includes a plurality of magnetic sensors 105, with four magnetic sensors 105A, 105B, 105C, and 105D shown in FIG. 9A. (For simplicity, this document refers generally to the magnetic sensors by the reference number 105. Individual magnetic sensors are given the reference number 105 followed by a letter.) It is to be understood that the detection device 100 may include more or fewer than four magnetic sensors 105. The magnetic sensor array 110 illustrated in the exemplary embodiment of FIG. 9A is a linear array.

In some embodiments, each of the plurality of magnetic sensors 105 is coupled to at least one line 120 for reading an output from one or more of the magnetic sensors 105. (For simplicity, this document refers generally to the lines by the reference number 120. Individual lines are given the reference number 120 followed by a letter.) The output provides an indication of magnetic field magnitude or a change in magnetic field magnitude and may comprise, for example, a resistance, a voltage, a current, a frequency, a noise, and/or a change in resistance, voltage, current, frequency, and/or noise of the magnetic sensor 105. In the exemplary embodiment shown in FIG. 9A, each magnetic sensor 105 of the magnetic sensor array 110 is coupled to two lines 120. Specifically, the magnetic sensor 105A is coupled to the lines 120A and 120E, the magnetic sensor 105B is coupled to the lines 120B and 120E, the magnetic sensor 105C is coupled to the lines 120C and 120E, and the magnetic sensor 105D is coupled to the lines 120D and 120E. In the exemplary embodiment, the lines 120A, 120B, 120C, and 120D reside under the magnetic sensors 105A, 105B, 105C, and 105D, respectively, and the line 120E resides over the magnetic sensors 105. FIG. 9B shows the magnetic sensor 105D in relation to the lines 120D and 120E.

The detection device 100 also includes a fluidic channel 115 that is adjacent to the magnetic sensor array 110. As its name suggests, the fluidic channel 115 is configured to hold fluids (e.g., liquids, gases, plasmas) when the detection device 100 is in use. The fluidic channel 115 may by open (e.g., if its shape is rectangular, it may have three sides; if its shape is curved, it may have a shape that is a portion of a cylinder; etc.) or closed (e.g., if its shape is cuboid, it may have six sides; if its shape is curved, it may be cylindrical; etc.). The fluidic channel 115 may include at least one movable piece (e.g., a stopper, a flap, etc.) to allow fluid to enter into and/or exit the fluidic channel 115. The shape of the fluidic channel 115 may be regular or irregular. The fluidic channel 115 may include or may be coupled to a pump that forces fluids into and/or out of the fluidic channel 115 (e.g., through a membrane, opening, etc.). Alternatively, the fluidic channel 115 may be a passive receptacle (e.g., it merely receives fluids but is not coupled to a device that injects or removes fluids).

As shown in FIG. 9B, the fluidic channel 115 has a wall 117 that is adjacent to the magnetic sensor array 110. The wall 117 may be substantially vertical as illustrated in FIG. 9B. Alternatively, the wall 117 may be sloped at least in part (e.g., some or all of the interior of the fluidic channel 115 may be curved (e.g., in the shape of a portion or all of a cylinder) or non-vertical in part or in whole). In general, the fluidic channel 115 and wall 117 may have any shapes that allow the magnetic sensors 105 to detect the presence of MNPs near or attached to the wall 117, within the fluidic channel 115.

As described above, when the detection device 100 is in use, the magnetic sensors 105 are able to detect magnetic fields and/or changes in magnetic fields caused by MNPs that are in the fluidic channel 115. In some embodiments, the magnetic sensors 105 are able to detect magnetic field magnitudes caused by MNPs in the vicinity of the magnetic sensors 105.

The wall 117 has properties and characteristics that protect the magnetic sensors 105 from whatever fluid is in the fluidic channel 115 while still allowing the magnetic sensors 105 to detect magnetic fields and/or changes to magnetic fields in their vicinities due to MNPs that are within the fluidic channel 115. For example, the material of the wall 117 (and potentially of the rest of the fluidic channel 115) may be or comprise an insulator. For example, in some embodiments, a surface of the wall 117 comprises polypropylene, gold, glass, and/or silicon. In addition, the thickness of the wall 117 may be selected so that the magnetic sensors 105 can detect magnetic fields caused by MNPs within the fluidic channel 115. In some embodiments, the wall 117 is approximately 2 nm to approximately 20 nm thick. It is desirable for the MNPs coupled to molecules being detected to be close to the sensors 105 but separated from them by enough insulator to electrically passivate the magnetic sensors 105. The thickness of the wall 117 may be selected to meet this objective. Those having ordinary skill in the art will be able to select a suitable material and a suitable thickness of the wall 117.

FIG. 9C is a cross-section view of the detection device 100 along the dashed line labeled "9C" in FIG. 9A. Because the cross-section is taken at a point within the fluidic channel 115, the magnetic sensors 105 and lines 120 would not be visible and are, therefore, shown using dashed lines to illustrate their positions within the detection device 100. As shown in FIG. 9C, in some embodiments, the wall 117 has a support structure 114 (or multiple support structures 114) configured to anchor molecules to be sensed (e.g., nucleic acid or molecules of a nucleic acid polymerase) to the wall 117 near the magnetic sensors 105. FIG. 9C illustrates four individual support structures 114A, 114B, 114C, and 114D, each of which corresponds to a magnetic sensor 105 (e.g., support structure 114A corresponds to magnetic sensor 105A, support structure 114B corresponds to magnetic sensor 105B, etc.). The support structure 114 (or support structures 114) of the wall 117 may include a cavity or a ridge to which molecules may be attached or anchored. Although FIG. 9C shows individual support structures 114 corresponding to each of the magnetic sensors 105, the detection device 100 may have fewer or more support structures 114 than shown. For example, there may be more support structures 114 than magnetic sensors 105, such that each magnetic sensor 105 is near multiple support structures 114. As another example, multiple magnetic sensors 105 may share a single support structure 114. As yet another example, multiple magnetic sensors 105 may share multiple support structures 114. In embodiments in which the detection device 100 includes multiple support structures 114, those support structures 114 may be the same as or similar to each other, or they may be different from each other.

In some embodiments, it may be advantageous for each magnetic sensor 105 to detect MNPs coupled to a single respective support structure 114. For example, in some types of SBS, a long strand of DNA is (or a plurality of long strands of DNA from a single donor organism are) cut into smaller, random-length segments prior to sequencing. All of these smaller strands, which are from the same donor, are randomized sub-strands of the complete strand to be sequenced. For example, if the complete strand includes the sequence ATGGCTTAG, the smaller strands could include, for example, distinct sub-strands (e.g., ATGG and TTAG) as well as, if a plurality of the longer strands are cut into sub-strands, sub-strands that partially or completely overlap other sub-strands (e.g., GGCTT and ATGGCT). All of the smaller, randomized sub-strands may be sequenced at the same time, potentially after being amplified. In such applications, it will be appreciated that because the sub-strands do not represent the same sub-sequences, it may be desirable for each magnetic sensor 105 to detect magnetic fields and/or changes in magnetic fields caused by single MNPs because the sequencing of the sub-strands will not be coordinated (or synchronized) amongst sub-strands. For example, during a single sequencing cycle, a first sub-strand may incorporate cytosine, a second sub-strand might incorporate thymine, and a third sub-strand might incorporate adenine. In order to sequence multiple random segments of a larger nucleic acid strand, it is desirable, in each sequencing cycle, to determine whether and at which physical location(s) each dNTP type has been incorporated.

To simplify the explanation, FIGS. 9A, 9B, and 9C illustrate an exemplary detection device 100 with a single fluidic channel 115 and only four magnetic sensors 105A, 105B, 105C, 105D in the magnetic sensor array 110. It is to be appreciated that the detection device 100 may have many more magnetic sensors 105 in the magnetic sensor array 110, and it may have either additional fluidic channels 115 or a more intricate single fluidic channel 115 (e.g., with a different shape or with interconnected channels). In general, any configuration of magnetic sensors 105 and fluidic channel(s) 115 that allows the magnetic sensors 105 to detect temperature changes caused by MNPs in the fluidic channel(s) 115 may be used.

Figure 9D:
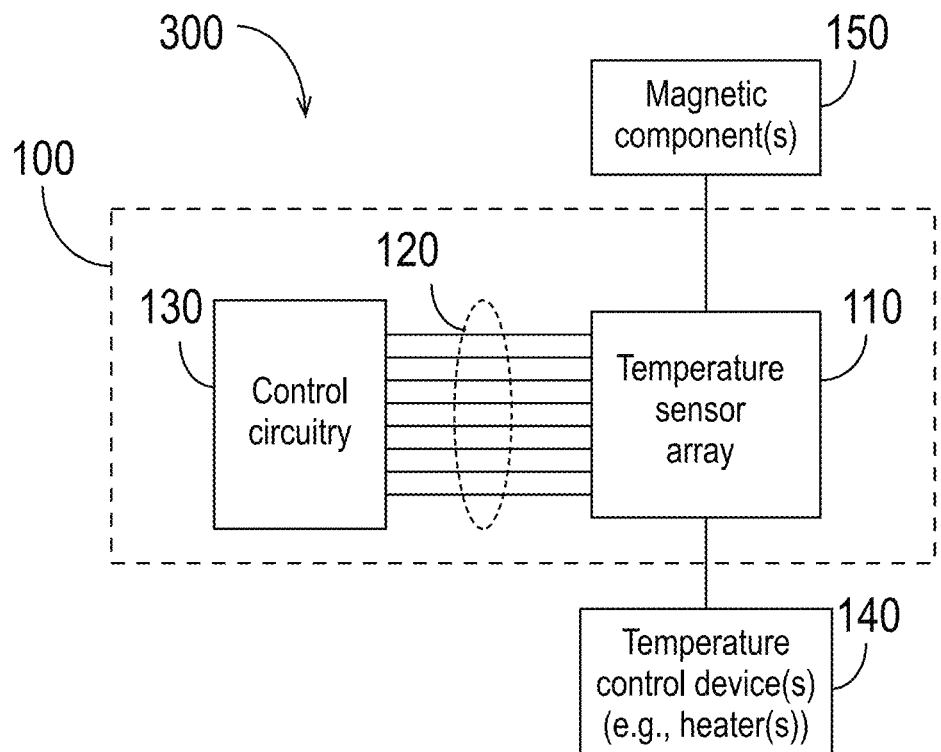
FIG. 9D is a block diagram showing an exemplary detection system for molecule detection in accordance with some embodiments.

FIG. 9D is a block diagram showing an exemplary detection system 300 for molecule detection in accordance with some embodiments. As illustrated in FIG. 9D, the system 300 includes a detection device 100. As shown in the exemplary embodiment of FIG. 9D, the detection device may comprise control circuitry 130 coupled to the magnetic sensor array 110 via the lines 120. The control circuitry 130 may comprise any suitable components, including, generally, suitable detection circuitry. Such control circuitry 130 may comprise hardware and/or software. The control circuitry 130 may include, for example, one or more of: a processor capable of executing machine-executable instructions, an application-specific integrated circuit (ASIC), a controller, a programmable circuit (e.g., FPGA), etc.

As also shown in FIG. 9D, the detection system 300 may also include one or more temperature control devices 140 (e.g., one or more heaters) and, optionally, one or more magnetic components 150. The magnetic component(s) 150 may comprise, for example, an electromagnet, a distributed coil, a solenoid, a permanent magnet, or a superconducting magnet. If present, the magnetic component 150 may provide a static (e.g., constant in time or DC) magnetic field to align the magnetic moments of the MNPs in the fluidic channel 115 in substantially the same direction. Although FIG. 9D illustrates the temperature control device(s) 140 and magnetic component(s) 150 as being separate from the detection device 100, one or more of the temperature control device(s) 140 and magnetic component(s) 150, if present, may be included in the detection device 100, or one or both of the temperature control device(s) 140 and magnetic component(s) 150 may be separate from the detection device 100.

Figure 10:
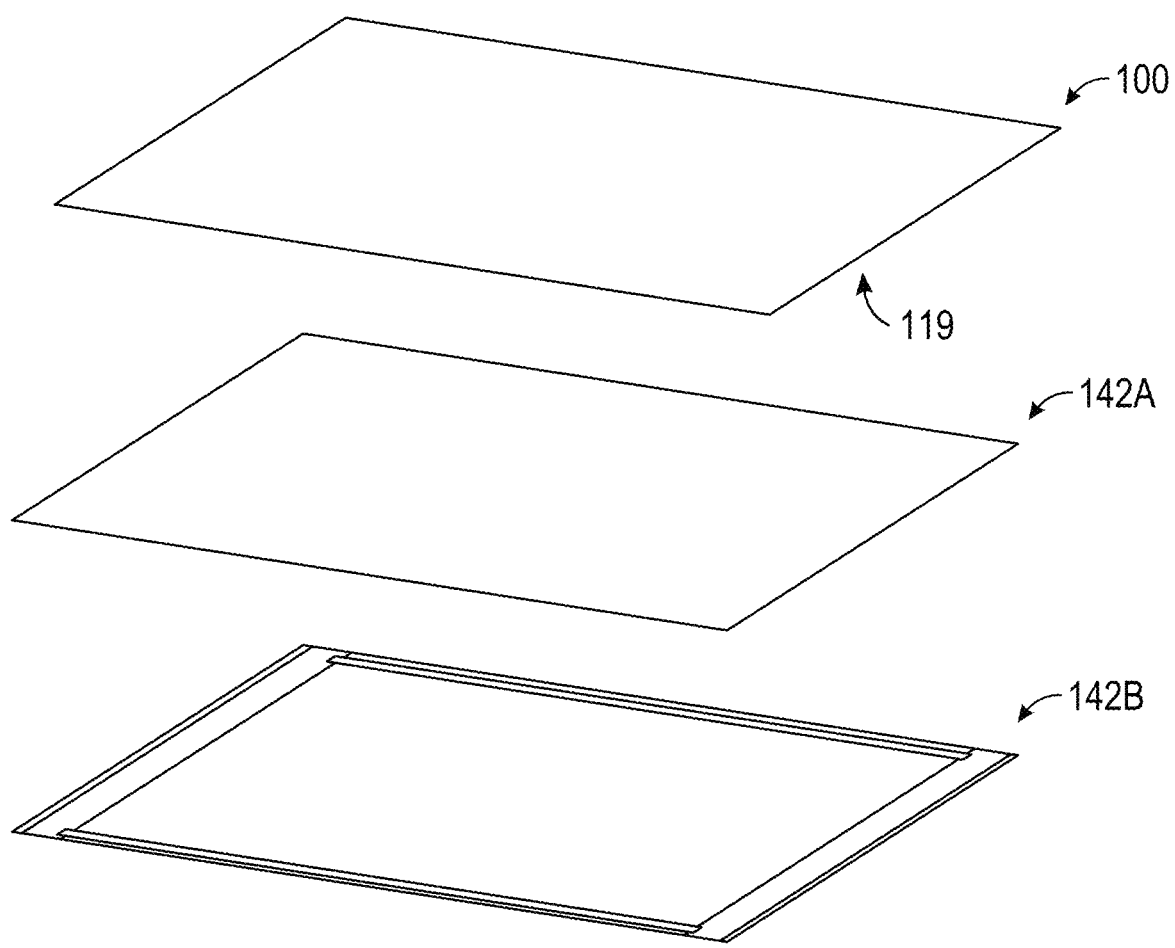
FIG. 10 is an exploded view of exemplary heating elements suitable for incorporation in or use with a detection device in accordance with some embodiments.

In some embodiments, the system 300 includes one or more temperature control device(s) 140, which may comprise, for example, one or more heating elements. For example, the system 300 may include a heat spreader, which may be coupled to the detection device 100. In some embodiments, the detection device 100 itself includes one or more heating elements 142 coupled, for example, to its bottom surface 119. FIG. 10 is an exploded view of exemplary heating elements 142 suitable for incorporation in or use with a detection device 100 in accordance with some embodiments. The detection device 100 shown in FIG. 10 includes or is coupled to a surface heater 142A that provides substantially uniform heating across the bottom surface 119 of the detection device 100. The detection device 100 shown in FIG. 10 also includes linear heaters 142B at or near the edges of the bottom surface 119 (see FIG. 12A), which may be used to remove a temperature gradient caused by the surrounding environment being at a different (e.g., cooler) temperature.

Figure 11:
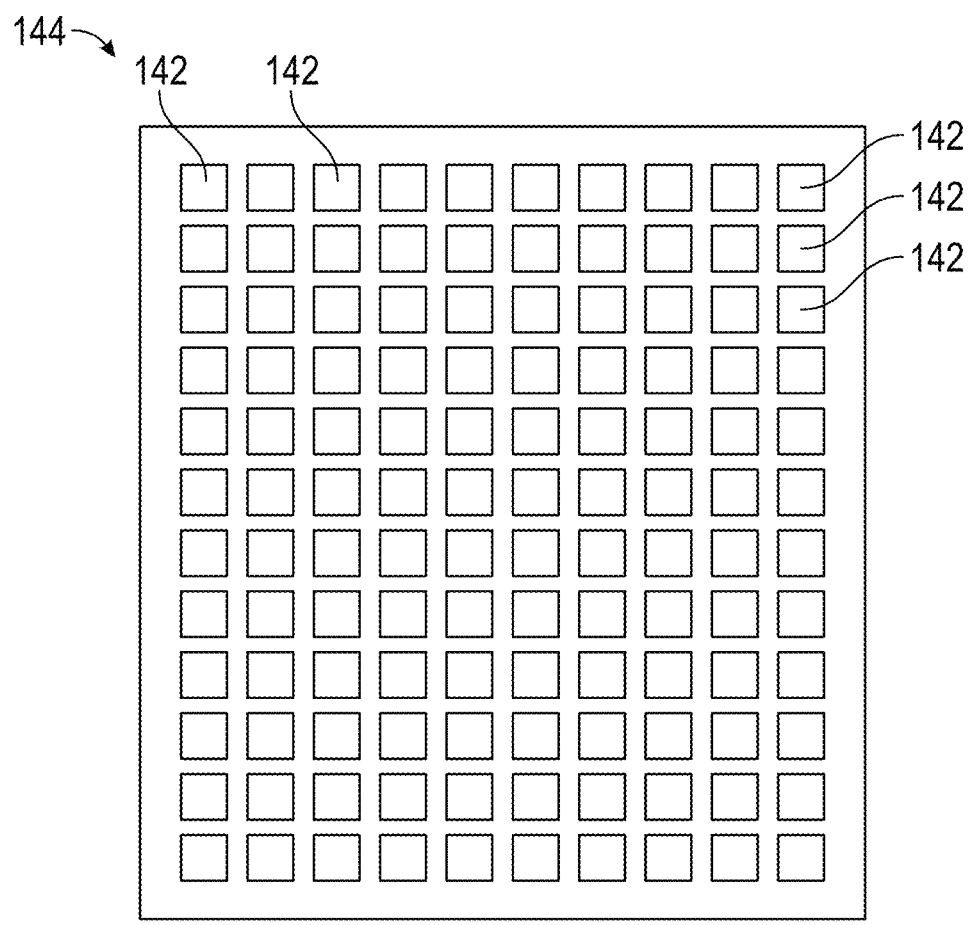
FIG. 11 illustrates an array of heating elements that may be coupled, for example, to the bottom surface of a detection device in accordance with some embodiments.

Alternatively or in addition, the detection device 100 may include an array of heating elements 142, which may be useful if fine temperature control is desirable. FIG. 11 illustrates an array 144 of heating elements 142 that may be coupled, for example, to the bottom surface 119 of the detection device 100 in accordance with some embodiments. To avoid obscuring the drawing, only a few of the heating elements 142 are shown with reference numbers.

As an example of a detection device 100 with a larger number of magnetic sensors 105 in the magnetic sensor array 110, FIGS. 12A, 12B, 12C, and 12D illustrate portions of an exemplary detection device 100 that includes several fluidic channels 115, one or more of which may be a separate fluidic channel 115 in accordance with some embodiments, or the aggregation of which may be considered a single fluidic channel 115. In the embodiment of the detection device 100 shown in FIGS. 12A, 12B, 12C, and 12D, the plurality of magnetic sensors 105 of the magnetic sensor array 110 is arranged in a rectangular grid pattern. Each of the lines 120 identifies a row or a column of the magnetic sensor array 110. It is to be understood that FIGS. 12A, 12B, 12C, and 12D show only a portion of the detection device 100 to avoid obscuring the parts of the detection device 100 being discussed. It is to be understood that the various illustrated components (e.g., lines 120, magnetic sensors 105, fluidic channels 115, etc.) might not be visible in a physical instantiation of the detection device 100 (e.g., some or all may be covered by protective material, such as an insulator). Moreover, as discussed herein, the detection device 100 may include other components not illustrated in FIGS. 12A, 12B, 12C, and 12D.

Figure 12A:
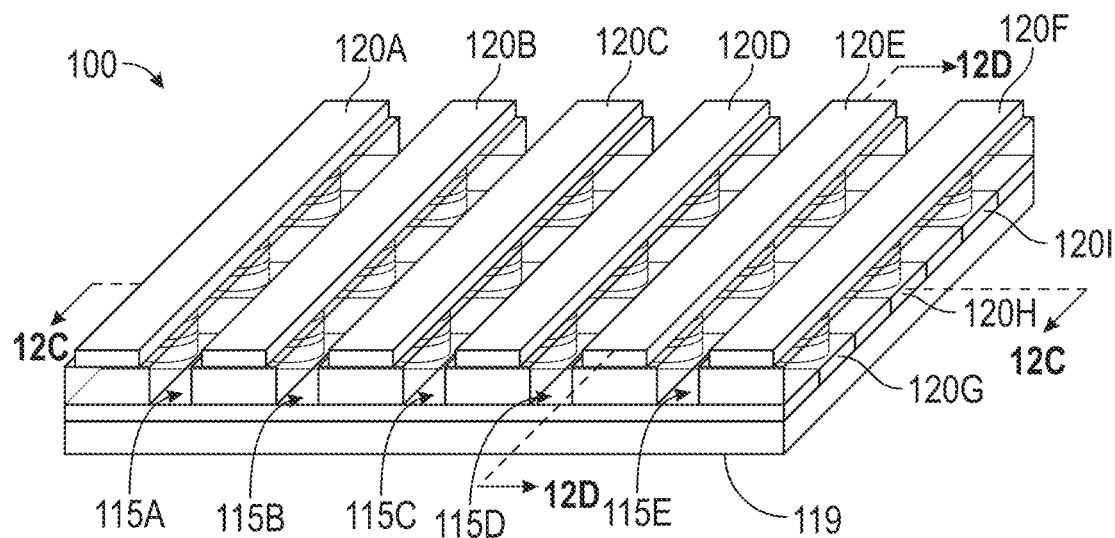
FIGS. 12A, 12B, 12C, and 12D illustrate portions of an exemplary detection device in accordance with some embodiments.

FIG. 12A is a perspective view of the exemplary detection device 100 in accordance with some embodiments. The exemplary detection device 100 includes nine lines 120, labeled as 120A, 120B, 120C, 120D, 120E, 120F, 120G, 120H, and 120I. It also includes five fluidic channels, labeled as 115A, 115B, 115C, 115D, and 115E. As explained above, the fluidic channels 115A, 115B, 115C, 115D, and 115E may be considered to be separate fluidic channels 115 or a single fluidic channel 115. The detection device 100 also has a bottom surface 119.

Figure 12B:
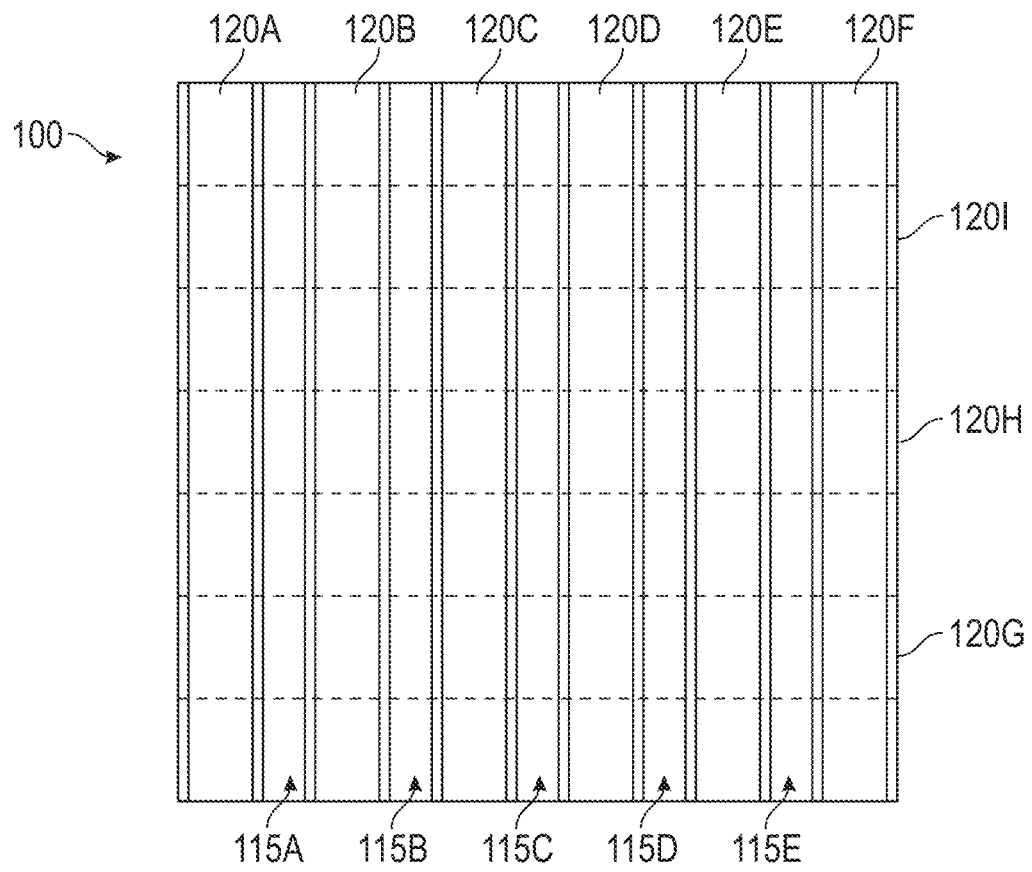

FIG. 12B is a top view of the exemplary detection device 100 shown in FIG. 12A. The lines 120G, 120H, and 120I, which are not visible from the top view, are shown using dashed lines to indicate their locations. The lines 120A-120F are shown in solid lines but, as explained above, the lines 120A-120F might also not be visible in the top view (e.g., they may be covered by protective material, such as an insulator).

Figure 12C:
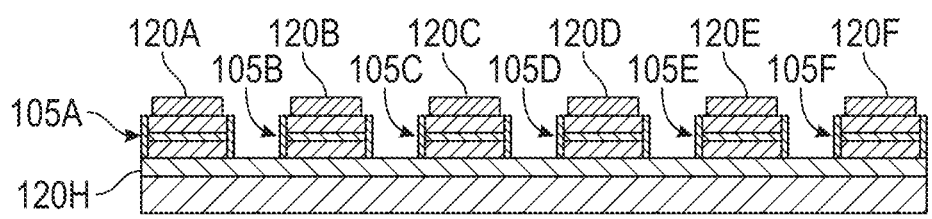

FIG. 12C is a cross-sectional view of the detection device 100 along the line labeled "12C" in FIG. 12A. As shown, each of the lines 120A, 120B, 120C, 120D, 120E, and 120F is in contact with the top of one of the magnetic sensors 105 along the cross-section (namely, line 120A is in contact with magnetic sensor 105A, line 120B is in contact with magnetic sensor 105B, line 120C is in contact with magnetic sensor 105C, line 120D is in contact with magnetic sensor 105D, line 120E is in contact with magnetic sensor 105E, and line 120F is in contact with magnetic sensor 105F). The line 120H is in contact with the bottom of each of the magnetic sensors 105A, 105B, 105C, 105D, 105E, and 105F. It is to be appreciated that although FIGS. 12A-12D illustrate the lines 120 in contact with the magnetic sensors 105, the lines 120 may, in general, be coupled to the magnetic sensors 105 (i.e., they may be directly connected, or there may be intervening components disposed between the lines 120 and the magnetic sensors 105).

Referring again to FIG. 12C, the magnetic sensors 105A and 105B are separated by the fluidic channel 115A (unlabeled in FIG. 12C but shown in FIG. 12A). Similarly, the magnetic sensors 105B and 105C are separated by the fluidic channel 115B, the magnetic sensors 105C and 105D are separated by the fluidic channel 115C, the magnetic sensors 105D and 105E are separated by the fluidic channel 115D, and the magnetic sensors 105E and 105F are separated by the fluidic channel 115E. As discussed further below, either or both of the vertical walls of each fluidic channel 115 may be the wall 117.

In some embodiments, each magnetic sensor 105 is assigned to a single fluidic channel 115. For example, in the exemplary device illustrated in FIGS. 12A-12D, the magnetic sensors 105 coupled to the line 120A may be configured to sense the presence or absence of MNPs in the fluidic channel 115A, the magnetic sensors 105 coupled to the line 120B may be configured to sense MNPs in the fluidic channel 115B, the magnetic sensors 105 coupled to the line 120C may be configured to sense MNPs in the fluidic channel 115C, the magnetic sensors 105 coupled to the line 120D may be configured to sense MNPs in the fluidic channel 115D, and the magnetic sensors 105 coupled to the line 120E may be configured to sense MNPs in the fluidic channel 115E.

In the exemplary embodiment illustrated in FIGS. 12A-12D, there are more columns of magnetic sensors 105 than there are fluidic channels 115 (i.e., in the exemplary embodiment shown, there are six columns corresponding to lines 120A-120F and only five fluidic channels 115A-115E). In such embodiments, each wall of one fluidic channel 115 may be the wall 117. In other words, a single fluidic channel 115 may be sensed by twice as many magnetic sensors 105 as each of the other fluidic channels 115. For example, in the exemplary embodiment of FIGS. 12A-12D, any of the fluidic channels 115 may be sensed by two columns of magnetic sensors 105. For example, the fluidic channel 115B may be sensed by the magnetic sensors 105 coupled to both lines 120B and 120C. In this example, the magnetic sensors 105 coupled to the line 120A would be assigned to sense the contents of the fluidic channel 120A, the magnetic sensors 105 coupled to the line 120D would be assigned to sense the contents of the fluidic channel 120C, the magnetic sensors 105 coupled to the line 120E would be assigned to sense the contents of the fluidic channel 120D, and the magnetic sensors 105 coupled to the line 120F would be assigned to sense the contents of the fluidic channel 120E.

Figure 12D:
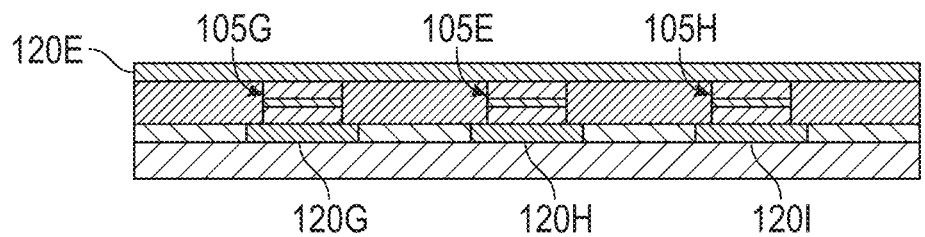

FIG. 12D is a cross-sectional view of the detection device 100 along the line labeled "12D" in FIG. 12A. As shown, the line 120E is in contact with the top of each of the sensors 105G, 105E, and 105H along the cross-section. Each of the lines 120G, 120H, and 120I is in contact with the bottom of one of the magnetic sensors 105 along the cross-section (namely, line 120G is in contact with magnetic sensor 105G, line 120H is in contact with magnetic sensor 105E, and line 120I is in contact with magnetic sensor 105H).

Figure 12E:
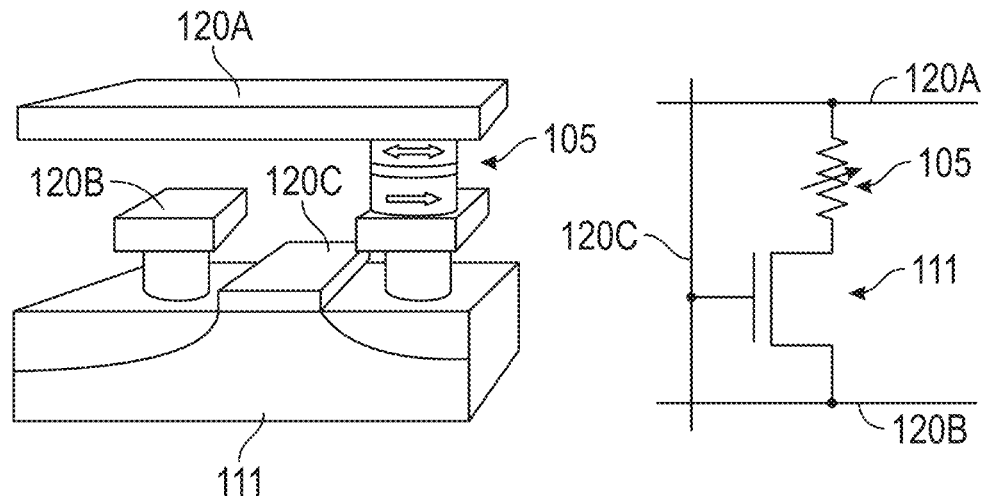
FIG. 12E illustrates an exemplary approach for selecting magnetic sensors in accordance with some embodiments.
Figure 12F:
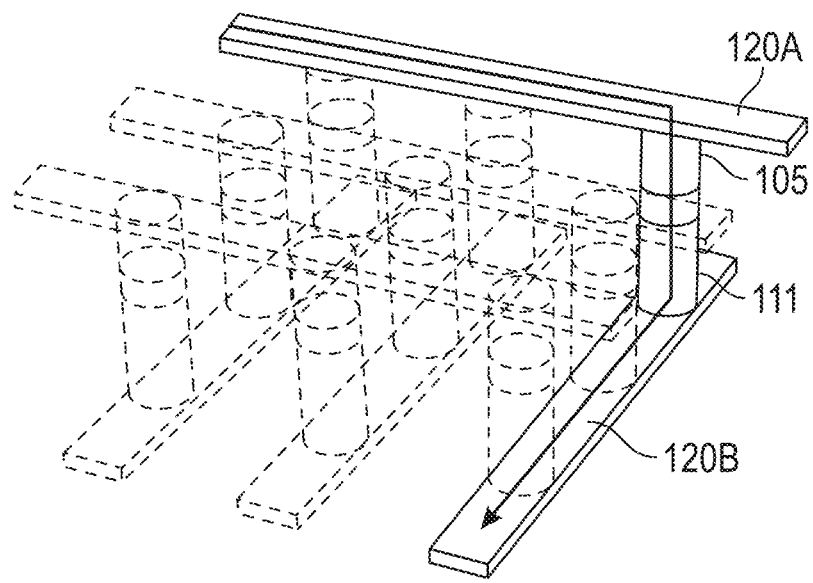
FIG. 12F illustrates another exemplary magnetic sensor selection approach in accordance with some embodiments.

As explained above, the lines 120 shown in FIG. 12D need not be in direct contact with the magnetic sensors 105; instead, they may be connected through intervening components. For example, in some embodiments, such as shown in FIGS. 12E and 12F, the detection device 100 includes a plurality of selector elements 111, each of which is coupled to a respective one of the magnetic sensors 105, where each of the selector elements 111 exhibits thresholding behavior such that for voltages above a particular value ($V_{th}$), the selector element 111 has high conductivity, and below that voltage the conductivity of the selector element 111 is effectively zero. The selector elements 111 may comprise, for example, transistors, diodes, etc. As will be appreciated by those having ordinary skill in the art, different schemes of addressing (selecting) the magnetic sensors 105 (individually or in groups) can be used that ensure only the voltage dropped across the intended magnetic sensor(s) 105 is above $V_{th}$. Accordingly, selector elements 111 may be used reduce the chances of "sneak" currents that could transmit through neighboring elements and degrade the performance of the detection device 100.

FIG. 12E illustrates an exemplary approach for selecting magnetic sensors 105 in accordance with some embodiments. In the exemplary embodiment shown in FIG. 12E, a respective selector element 111 (shown in the exemplary embodiment as a CMOS transistor) is coupled in series with the magnetic sensor 105. In this exemplary embodiment, three lines 120A, 120B, and 120C allow an output from the magnetic sensor 105 to be obtained or sensed. Conceptually, the line 120A may be considered to be a read-out line, the line 120C may be considered to be a control line, and the line 120B may be considered to be either or both a read-out line and a control line. Each magnetic sensor 105 of an array 110 may be coupled in series to a respective selector element 111. For more detail on configurations such as the exemplary one shown in FIG. 12E, see B. N. Engel, J. Akerman, B. Butcher, R. W. Dave, M. DeHerrera, M. Durlam, G. Grynkewich, J. Janesky, S. V. Pietambaram, N. D. Rizzo, J. M. Slaughter, K. Smith, J. J. Sun, and S. Tehrani, "A 4-Mb Toggle MRAM Based on a Novel Bit and Switching Method," IEEE Transactions on Magnetics, Vol. 41, 132 (2005).

FIG. 12F illustrates another exemplary magnetic sensor 105 selection approach in accordance with some embodiments. In the exemplary embodiment shown in FIG. 12F, a selector element 111 (e.g., a diode or a similar thresholding element, as is known in the art, such as semiconductor diodes, operational transconductance amplifiers (OTAs), vanadium oxide layers, capacitive threshold-logic gates, etc.) is deposited "in-stack" together with each of the magnetic sensors 105, which are placed into a cross-point architecture. Although FIG. 12F shows the in-stack selector elements 111 under the magnetic sensors 105, it is to be understood that the stacking of the in-stack selector elements 111 and the magnetic sensors 105 may be reversed (i.e., the in-stack selector elements 111 may be over the magnetic sensors 105). Respective selector devices (e.g., CMOS transistors) may be used to turn on the individual lines 120A, 120B to address/access individual magnetic sensors 105 in the detection device 100. The use of CMOS select transistors may be simple due to the prevalence of foundries available to fabricate the front end (e.g., the nanofabrication to build the CMOS transistors and underlying circuitry), but the types of currents used for operation may use a cross-point design to eventually reach the densities desired. Additional details on configurations suitable to select magnetic sensors 105 (e.g., in cross-point arrays) may be found in C. Chappert, A. Fert, and F. N. Van Daul, "The emergence of spin electronics in data storage," Nature Materials, Vol. 6, 813 (2007) and in J. Woo et al., "Selector-less RRAM with non-linearity of device for cross-point array applications," Microelectronic Engineering 109 (2013) 360-363.

In embodiments in which the magnetic sensors 105 are arranged in a cross-point array, entire columns or entire rows may be read simultaneously to improve the accuracy of the detection.

As described herein, the exemplary detection device(s) 100 shown and described herein (e.g., in reference to FIGS. 8A-12F) can be used with methods using SBS protocols that use magnetically-labeled nucleotide precursors. SBS involves binding of primer-hybridized template DNA, incorporation of a deoxynucleoside triphosphate (dNTP), and detection of incorporated dNTP. The detection device 100 can be used to expose the magnetic sensors 105 to sequencing reagents in the fluidic channel(s) 115 while protecting the magnetic sensors 105 using, for example, an electrically-insulating material. As described herein, DNA synthesis may be performed using polymerase molecules placed in the proximity of the magnetic sensors 105, which detect the presence of MNPs.

In particular, as described herein, either molecules of polymerase or fragments of single-strand nucleic acid may be attached to the side wall(s) 117 of the fluidic channel(s) 115 in the proximity of one or more of the magnetic sensors 105. Sequencing can then be performed by adding, to the fluidic channel(s) 115, a nucleic acid template (having a primer binding site and an extendable primer) and magnetically-labeled nucleotide precursors (at least some types of nucleotide precursor labeled by a distinguishable MNP), and sequencing the nucleic acid template by using the lines 120 to detect an output from the magnetic sensors 105. The output may indicate which of the magnetically-labeled nucleotide precursors has been incorporated into the extendable primer (e.g., if multiple nucleotide precursors, each labeled by a different MNP type, are added to the fluidic channel(s) 115 at substantially the same time), or it may indicate whether a particular magnetically-labeled nucleotide precursor has been incorporated into the extendable primer (e.g., if different nucleotide precursors labeled by MNPs (which may be the same type of MNP for each type of nucleotide precursor) are added to the fluidic channel(s) 115 sequentially). For DNA sequencing specifically, because adenine (A) pairs only with thymine (T), and cytosine (C) pairs only with guanine (G), detection of the MNPs enables the determination of which of the magnetically-labeled nucleotide precursors has been incorporated. In particular, if the MNP labeling A is detected, the recorded base is T (and vice versa), and if the MNP labeling C is detected, the recorded base is G (and vice versa).

Figure 13A:
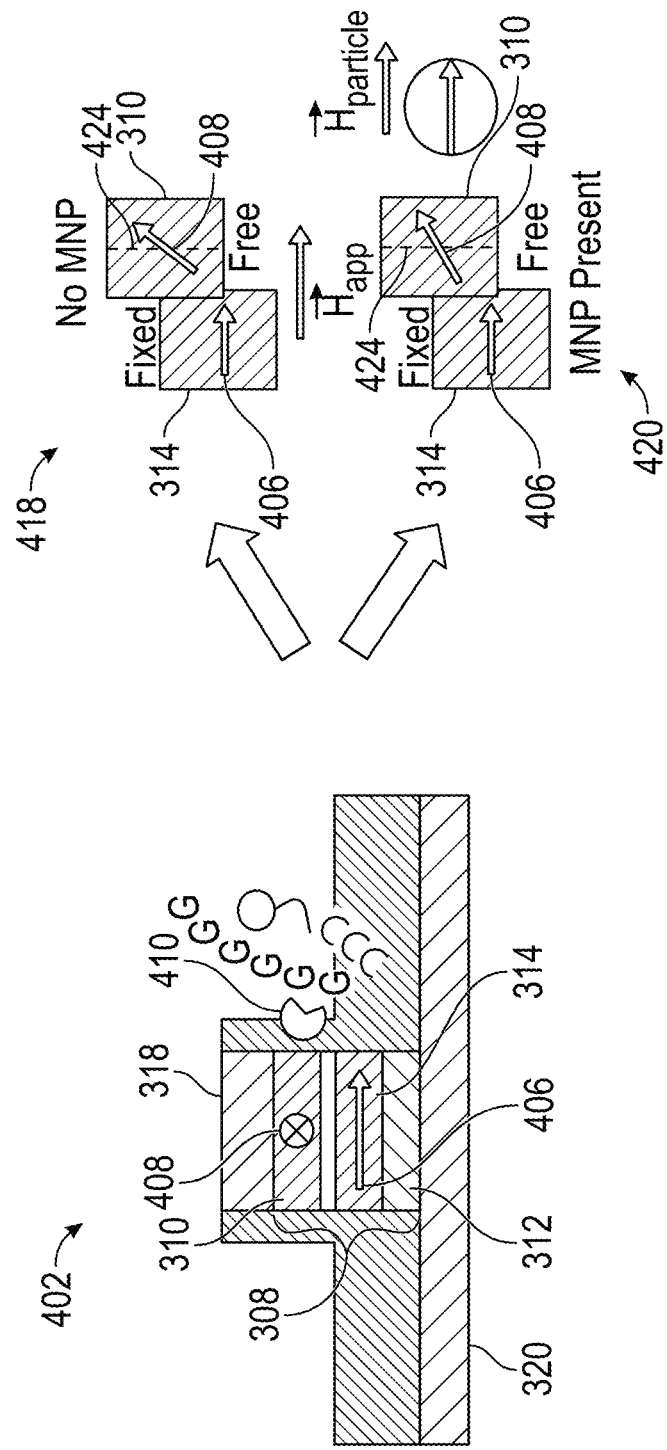
FIGS. 13A and 13B illustrate a magnetic sensor and detection using that magnetic sensor in accordance with some embodiments.

In some embodiments, target molecules to be detected (e.g., nucleic acid strands to be sequenced) are attached to the walls 117 of the fluidic channels 115 as shown in the left panel of FIG. 13A and may have polymerase 410 introduced at this point. Individual bases with attached MNPs may then be introduced into the fluidic channels 115. The appropriate (complementary) base pair (i.e., for DNA sequencing, cytosine (C) with guanine (G) or adenine (A) with thymine (T)) will then be incorporated and can be detected. Assuming this process is done one base pair at a time, sub-panel 402 (left) of FIG. 13A illustrates a detection method according to an embodiment in which the presence or absence of the MNP, and therefore the base, can be determined using the various device embodiments of, for example, FIGS. 8A-12F. As shown in sub-panel 402, polymerase 410 is bound to the wall 117 and is used to capture induced DNA bases for detection.

Sequencing can occurs by applying a magnetic field (Happ) across the MTJ element 308 (an example of the magnetic sensor 105). The magnetic field may be applied using an electromagnet, e.g., by placing the pole pieces on either side of the detection device), a distributed coil, a solenoid oriented perpendicular to the fluidic channel 115, etc. to generate the magnetic field in the direction of the pinned layer's moment 406. The means for generating the magnetic field may be mounted, for example, on the bottom surface 119 of the detection device 100. As another example, the means for generating a magnetic field may be included in a system that includes the detection device 100. It is to be understood that other suitable means of generating the magnetic field, such as, for example, by using permanent magnets or super-conducting magnets, are possible, are specifically contemplated herein, and are not excluded.

The applied magnetic field can achieve at least two objectives: (1) it aligns the moments of all the MNPs in a common direction so that the measured signals due to the presence of a MNP are similar, and (2) it rotates the free layer's moment 408 toward (or away from, depending on the field orientation) the pinned layer's moment 406 and thus changes the resistance of the magnetic sensor 105 from its equilibrium resistance.

The right-hand portion of FIG. 13A illustrates the pinned layer 314 (labeled "fixed") and free layer 310 as if viewing sub-panel 402 from above. The pinned layer 314 and free layer 310 are drawn offset from each other to illustrate their moments. The dashed line 424 shown in the free layer 310 is the equilibrium direction of the free layer 310's moment. In the absence of a MNP near the MTJ element 308 (or, more generally, the magnetic sensor 105), illustrated as case 418 (top) on the right-hand side of FIG. 13A, the magnetic field can rotate the magnetic moment 408 of the free layer 310 into the direction of the magnetic moment 406 of the pinned layer 314 (depending on the details of the MTJ element 308/magnetic sensor 105 design). In the presence of a MNP near the MTJ element 308 (or, more generally, the magnetic sensor 105), illustrated as case 420 (bottom) on the right-hand side of FIG. 13A, fringing fields (Hparticle) will be created. These fringing fields will be in the same direction as the applied field and, therefore, can add significantly to the applied field locally near the magnetic sensor 105 (shown as a MTJ element 308). The magnetic moment 408 of the free layer 310 will then rotate more substantially from its equilibrium position (dashed line 424), as shown in case 420. Therefore, by connecting the magnetic sensors 105 to detection electronics that measure the resistance of the magnetic sensors 105 (or a proxy for the resistance, such as, for example, the voltage across the magnetic sensors 105 for a given current), the presence or absence of a MNP can be detected. The detection can be accomplished by either measuring the absolute resistance of each magnetic sensor 105 (e.g., each MTJ element 308) or by comparing the resistances to a reference cell or bit (e.g., a magnetic sensor 105 that is completely encapsulated such that it is not exposed to or affected by the field from a MNP).

Figure 13B:
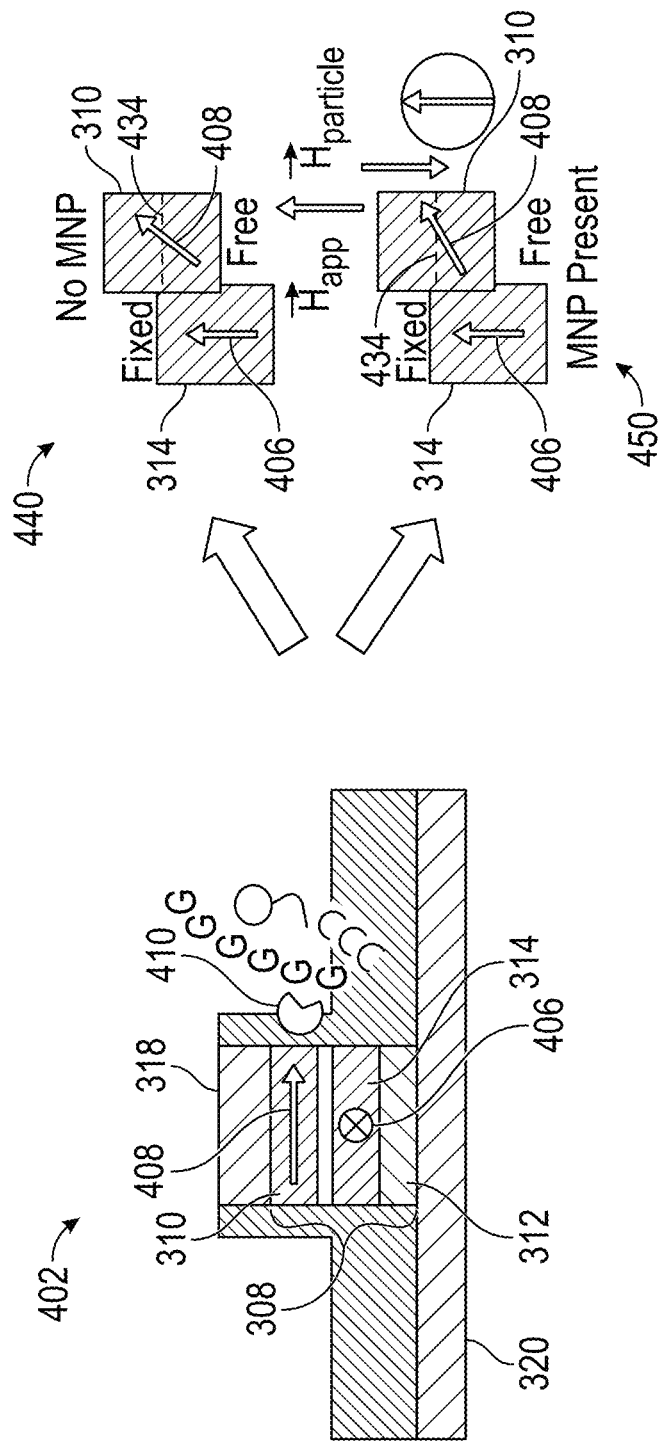

FIG. 13B illustrates another embodiment in which the magnetic moments 408 and 406 of, respectively, the free layer 310 and pinned layer 314 are reversed in arrangement relative to FIG. 13A. The dashed line 434 shown in the free layer 310 is the equilibrium direction of the free layer 310's moment. As FIG. 13B illustrates, if the applied field Happ is in the direction along the fluidic channel 115, the fringing field Hparticle will be in an opposite direction to the applied field Happ. Thus, in the absence of a MNP near the MTJ element 308 (or, more generally, the magnetic sensor 105), illustrated as case 440 (top) on the right-hand side of FIG. 13B, the magnetic field can rotate the magnetic moment 408 of the free layer 310 into the direction of the magnetic moment 406 of the pinned layer 314 (depending on the details of the MTJ element 308/magnetic sensor 105 design). In the presence of a MNP, however, the magnetic moments 408 and 406 will be closer to a 90-degree alignment as shown in the bottom portion of the right-hand side of FIG. 13B (case 450).

Method of Manufacturing Detection Device

Figure 14:
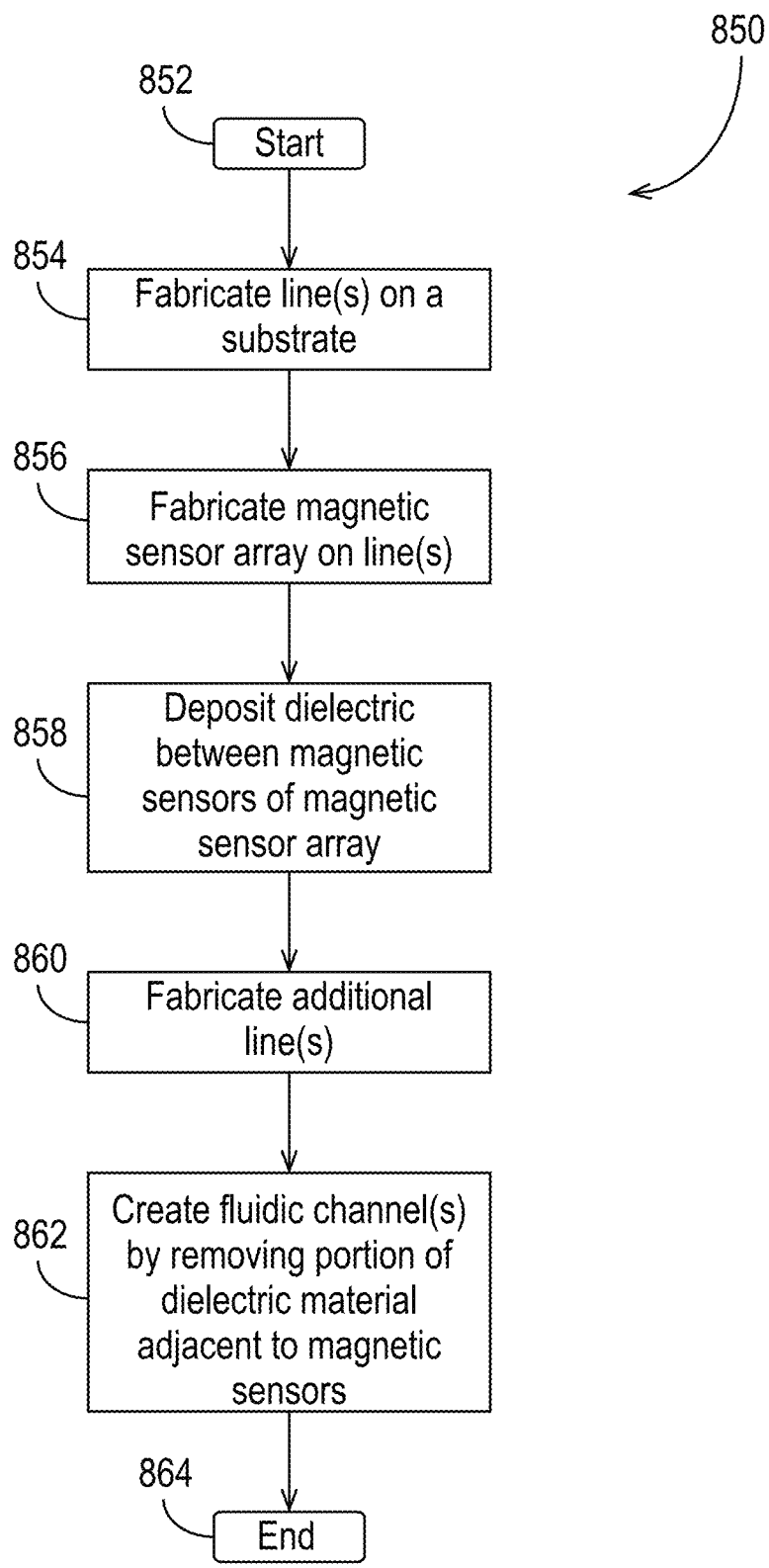
FIG. 14 illustrates a method of manufacturing a detection device in accordance with some embodiments.
Figure 15:
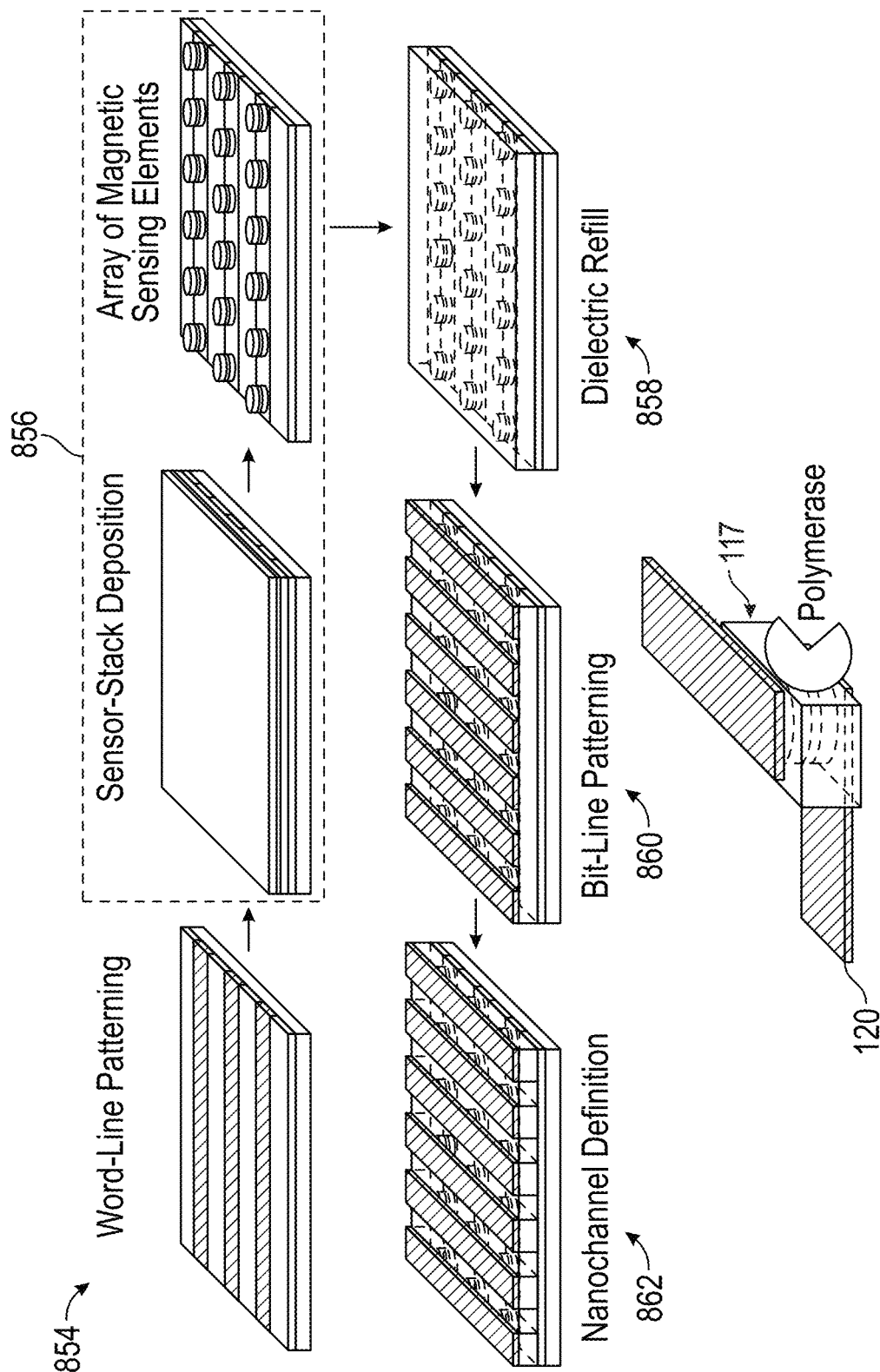
FIG. 15 illustrates the results of each step of the fabrication process of FIG. 14 in accordance with some embodiments.

In some embodiments, a detection device 100 is fabricated using photolithographic processes and thin film deposition. FIG. 14 illustrates a method 850 of manufacturing the detection device 100, and FIG. 15 illustrates the results of each step of the fabrication process 850 with a final panel showing polymerase bound to the wall 117 proximate to a magnetic sensor 105 in accordance with some embodiments (e.g., when the detection device 100 is used for nucleic acid sequencing). At 852, the method begins. At 854, at least one line 120 is fabricated on a substrate, for example, by depositing one or more metal layers, using, for example, photolithography to pattern an array of lines and spaces in a polymer layer applied on top of the metal layers, using that polymer layer as a mask for etching the metal layers into an array of lines, depositing an insulating dielectric material, stripping the polymer layer and dielectric material over the lines, and performing chemical mechanical polishing to planarize the surface. At 856, the magnetic sensor array 110 is fabricated on the at least one line 120. Each magnetic sensor 105 of the magnetic sensor array 110 has a bottom portion 108 and a top portion 109. (See FIG. 6.) The bottom portion 108 is coupled to the at least one line 120. In some embodiments, the bottom portion 108 of each magnetic sensor 105 is in contact with the at least one line 120.

At 858, dielectric material is deposited between the magnetic sensors 105 of the magnetic sensor array 110. At 860, additional lines 120 are fabricated. Each of these additional lines 120 is coupled to the top portion 109 of at least one magnetic sensor 105 in the magnetic sensor array 110. In some embodiments, the top portion 109 of each magnetic sensor 105 is in contact with a line 120. In some embodiments, the bottom portion 108 of a magnetic sensor 105 is in contact with a first line 120A, and the top portion 109 of the magnetic sensor 105 is in contact with a second line 120B. At 862, a portion of the dielectric material adjacent to the magnetic sensors 105 is removed (e.g., by milling, etching, or any other suitable removal process) to create the fluidic channel 115. At 864, the process 850 ends.

The embodiments disclosed herein offer several advantages. For example, as previously explained, an advantage of some embodiments is that they simplify the introduction and incorporations of bases into the microfluidic cell by forcing the magnetic nanoparticles used as tags to become paramagnetic when added to the fluidic channel of a detection device, so that they do not interact with each other through magnetic forces.

Another advantage of some embodiments is that they allow for simultaneous tagging of all four nucleotide precursors in a manner that allows them to be distinguished. This means a single chemistry step can be used to read a single base in the target DNA strand with either three or four subsequent measurements at, respectively, three or four different temperatures selected to exploit the temperature-dependence of MNPs (e.g., that they are paramagnetic above the Curie temperature and ferromagnetic below it). Because individual chemistry steps and take the order of minutes, the disclosed embodiments can significantly speed up molecule detection, such as DNA sequencing, without affecting the read error rates.

As explained previously, although the description herein focuses on DNA, the various embodiments described can be applied to nucleic acid sequencing in general. Similarly, although SBS is used for illustrative purposes in the description, the various embodiments are not so limited to SBS sequencing protocols (e.g., dynamic sequencing could be used instead). The resulting array of magnetic sensors 105 (e.g., as shown in FIG. 6) can be used with a method that uses SBS protocols involving DNA bases (nucleotide precursors) labeled with MNPs. The array of magnetic sensors coupled with an array of etched nanochannels (e.g., as shown in FIGS. 9 and 12A) may advantageously be used to expose individual magnetic sensors 105 to sequencing reagents while protecting the magnetic sensors 105 with electrically insulating material. DNA synthesis may be performed by polymerase molecules placed in the proximity of densely-packed magnetic field sensing elements (e.g., magnetic sensors 105). SBS involves binding of primer-hybridized template DNA, insertion and incorporation of a deoxynucleoside triphosphate (dNTP).

In particular, polymerase can be attached to the nanochannel side-walls of a detection device 100 in the proximity of one or more magnetic sensor elements within the array. For example, sequencing can be performed by adding magnetic nanoparticles with DNA bases (four types of nanoparticles, each group of nanoparticles containing only one kind of tethered base) into the nanofluidic or microfluidic channels, one type of nanoparticles at a time. Since MNPs will only bind to polymerase with primer-hybridized template DNA when the appropriate base pair is incorporated (i.e., cytosine (C) with guanine (G) or adenine (A) with thymine (T)), the detection of a magnetic particle will allow for determination of the base at the unterminated end of the template DNA.

In the foregoing description and in the accompanying drawings, specific terminology has been set forth to provide a thorough understanding of the disclosed embodiments. In some instances, the terminology or drawings may imply specific details that are not required to practice the invention.

To avoid obscuring the present disclosure unnecessarily, well-known components are shown in block diagram form and/or are not discussed in detail or, in some cases, at all.

Unless otherwise specifically defined herein, all terms are to be given their broadest possible interpretation, including meanings implied from the specification and drawings and meanings understood by those skilled in the art and/or as defined in dictionaries, treatises, etc. As set forth explicitly herein, some terms may not comport with their ordinary or customary meanings.

As used in the specification and the appended claims, the singular forms "a," "an" and "the" do not exclude plural referents unless otherwise specified. Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

The word "or" is to be interpreted as inclusive unless otherwise specified. Thus, the phrase "A or B" is to be interpreted as meaning all of the following: "both A and B," "A but not B," and "B but not A." Any use of "and/or" herein does not mean that the word "or" alone connotes exclusivity.

As used in the specification and the appended claims, phrases of the form "at least one of A, B, and C," "at least one of A, B, or C," "one or more of A, B, or C," and "one or more of A, B, and C" are interchangeable, and each encompasses all of the following meanings: "A only," "B only," "C only," "A and B but not C," "A and C but not B," "B and C but not A," and "all of A, B, and C."

To the extent that the terms "include(s)," "having," "has," "with," and variants thereof are used in the detailed description or the claims, such terms are intended to be inclusive in a manner similar to the term "comprising," i.e., meaning "including but not limited to." The terms "exemplary" and "embodiment" are used to express examples, not preferences or requirements.

The terms "over," "under," "between," and "on" are used herein refer to a relative position of one feature with respect to other features. For example, one feature disposed "over" or "under" another feature may be directly in contact with the other feature or may have intervening material. Moreover, one feature disposed "between" two features may be directly in contact with the two features or may have one or more intervening features or materials. In contrast, a first feature "on" a second feature is in contact with that second feature.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment.

The above detailed description has shown, described, and pointed out novel features as applied to various embodiments, but it is to be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others.

The drawings are not necessarily to scale, and the dimensions, shapes, and sizes of the features may differ substantially from how they are depicted in the drawings.

Although specific embodiments have been disclosed, it will be evident that various modifications and changes may be made thereto without departing from the broader spirit and scope of the disclosure. For example, features or aspects of any of the embodiments may be applied, at least where practicable, in combination with any other of the embodiments or in place of counterpart features or aspects thereof. Accordingly, the specification and drawings are to be regarded in an illustrative rather than a restrictive sense.

We claim:

1. A method of detecting molecules using a sequencing device comprising at least one fluidic channel and a plurality of magnetic sensors configured to detect magnetic nanoparticles (MNPs) within the at least one fluidic channel, the method comprising:
adding, to the at least one fluidic channel:
(i) a first plurality of molecules to be detected, at least some of the first plurality of molecules to be detected being labeled by a first type of MNP, wherein the first type of MNP has a first characteristic temperature such that, in a first temperature range below the first characteristic temperature, a magnitude of a magnetic field generated by the first type of MNP is greater than or equal to a first threshold, and, in a second temperature range above the first characteristic temperature, the magnitude of the magnetic field generated by the first type of MNP is less than the first threshold, and
(ii) a second plurality of molecules to be detected, at least some of the second plurality of molecules to be detected being labeled by a second type of MNP, wherein the second type of MNP has a second characteristic temperature, the second characteristic temperature being higher than the first characteristic temperature and higher than the second temperature range, such that, in the first temperature range and in the second temperature range, a magnitude of a magnetic field generated by the second type of MNP is greater than or equal to a second threshold;
setting a temperature within the at least one fluidic channel to be within the first temperature range;
obtaining a first output from a selected one of the plurality of magnetic sensors while the temperature of the at least one fluidic channel is within the first temperature range, the first output indicating a magnitude of a first detected magnetic field;
setting the temperature within the at least one fluidic channel to be within the second temperature range;
obtaining a second output from the selected one of the plurality of magnetic sensors while the temperature of the at least one fluidic channel is within the second temperature range, the second output indicating a magnitude of a second detected magnetic field; and
determining, based at least in part on the magnitude of the first detected magnetic field and the magnitude of the second detected magnetic field, whether the first type of MNP or the second type of MNP has been detected by the selected one of the plurality of magnetic sensors, to detect a presence of either the first or second plurality of molecules.

2. The method of claim 1, wherein at least one of the first output or the second output comprises one or more of a resistance, a voltage, a current, a frequency, a noise, or a change in resistance, voltage, current, frequency, or noise.

3. The method of claim 1, wherein the first threshold differs from the second threshold.

4. The method of claim 1, wherein determining, based at least in part on the magnitude of the first detected magnetic field and the magnitude of the second detected magnetic field, whether the first type of MNP or the second type of MNP has been detected by the selected one of the plurality of magnetic sensors comprises:
in response to the magnitude of the first detected magnetic field being greater than or equal to the first threshold and the magnitude of the second detected magnetic field being less than the first threshold, determining that the first type of MNP has been detected by the selected one of the plurality of magnetic sensors, or
in response to the magnitude of the first detected magnetic field being greater than or equal to the second threshold and the magnitude of the second detected magnetic field being greater than or equal to the second threshold, determining that the second type of MNP has been detected by the selected one of the plurality of magnetic sensors.

5. The method of claim 1, wherein the first characteristic temperature is a first Curie temperature and the second characteristic temperature is a second Curie temperature.

6. The method of claim 5, further comprising:
before adding, to the at least one fluidic channel, the first and second pluralities of molecules to be detected, setting the temperature within the at least one fluidic channel to a temperature value higher than both the first Curie temperature and the second Curie temperature, and wherein adding, to the at least one fluidic channel, the first and second pluralities of molecules to be detected occurs while the temperature within the at least one fluidic channel is at the temperature value higher than the first Curie temperature and the second Curie temperature.

7. The method of claim 6, wherein the temperature value is a first temperature value, and further comprising:
before adding, to the at least one fluidic channel, the first and second pluralities of molecules to be detected, setting a temperature of a mixture of the first and second pluralities of molecules to be detected to a second temperature value higher than both the first Curie temperature and the second Curie temperature, the second temperature value being identical to or different from the first temperature value.

8. The method of claim 1, wherein the first characteristic temperature is a first blocking temperature and the second characteristic temperature is a second blocking temperature.

9. The method of claim 8, further comprising:
before adding, to the at least one fluidic channel, the first and second pluralities of molecules to be detected, setting the temperature within the at least one fluidic channel to a temperature value higher than both the first blocking temperature and the second blocking temperature, and wherein adding, to the at least one fluidic channel, the first and second pluralities of molecules to be detected occurs while the temperature within the at least one fluidic channel is at the temperature value higher than both the first blocking temperature and the second blocking temperature.

10. The method of claim 8, further comprising:
before adding, to the at least one fluidic channel, the first and second pluralities of molecules to be detected, setting a temperature of a mixture of the first and second pluralities of molecules to be detected to a temperature value higher than both the first blocking temperature and the second blocking temperature.

11. The method of claim 1, wherein:
the magnitude of the magnetic field generated by the first type of MNP is less than the first threshold in a third temperature range, the third temperature range being higher than the second temperature range, higher than the second characteristic temperature, and lower than a third characteristic temperature of a third type of MNP, and the magnitude of the magnetic field generated by the second type of MNP is less than the second threshold in the third temperature range, and further comprising:
adding, to the at least one fluidic channel, a third plurality of molecules to be detected, at least some of the third plurality of molecules to be detected being labeled by the third type of MNP, wherein in the first, second, and third temperature ranges, a magnitude of a magnetic field generated by the third type of MNP is greater than or equal to a third threshold;
setting the temperature within the at least one fluidic channel to be within the third temperature range;
obtaining a third output from the selected one of the plurality of magnetic sensors while the temperature of the at least one fluidic channel is within the third temperature range, the third output indicating a magnitude of a third detected magnetic field; and determining, based at least in part on the magnitude of the third detected magnetic field, whether the third type of MNP has been detected by the selected one of the plurality of magnetic sensors.

12. The method of claim 11, wherein determining, based at least in part on the magnitude of the third detected magnetic field, whether the third type of MNP has been detected by the selected one of the plurality of magnetic sensors comprises:
in response to the magnitude of the first detected magnetic field being greater than or equal to the third threshold, and the magnitude of the second detected magnetic field being greater than or equal to the third threshold, and the magnitude of the third detected magnetic field being greater than or equal to the third threshold, determining that the third type of MNP has been detected by the selected one of the plurality of magnetic sensors.

13. The method of claim 11, wherein the first, second, and third pluralities of molecules are added to the at least one fluidic channel at a substantially same time.

14. The method of claim 11, wherein at least two of the first, second, and third thresholds are different.

15. The method of claim 11, wherein the first characteristic temperature is a first Curie temperature, the second characteristic temperature is a second Curie temperature, and
the third characteristic temperature is a third Curie temperature, wherein:
the third Curie temperature is higher than the second Curie temperature, and
the second Curie temperature is higher than the first Curie temperature.

16. The method of claim 15, further comprising:
before adding, to the at least one fluidic channel, the first, second, and third pluralities of molecules to be detected, setting the temperature within the at least one fluidic channel to a temperature value higher than the first Curie temperature, the second Curie temperature, and the third Curie temperature, and wherein adding, to the at least one fluidic channel, the first, second, and third pluralities of molecules to be detected occurs while the temperature within the at least one fluidic channel is at the temperature value higher than the first Curie temperature, the second Curie temperature, and the third Curie temperature.

17. The method of claim 11, wherein the first characteristic temperature is a first blocking temperature, the second characteristic temperature is a second blocking temperature, and the third characteristic temperature is a third blocking temperature:
the third blocking temperature differs from the second blocking temperature, and
the second blocking temperature differs from the first blocking temperature.

18. The method of claim 11, wherein:
the magnitude of the magnetic field generated by the first type of MNP is less than the first threshold in a fourth temperature range, the fourth temperature range being higher than the third temperature range, higher than the third characteristic temperature, and lower than a fourth characteristic temperature of a fourth type of MNP,
the magnitude of the magnetic field generated by the second type of MNP is less than the second threshold in the fourth temperature range, and the magnitude of the magnetic field generated by the third type of MNP is less than the third threshold in the fourth temperature range,
and further comprising:
adding, to the at least one fluidic channel, a fourth plurality of molecules to be detected, at least some of the fourth plurality of molecules to be detected being labeled by the fourth type of MNP, wherein in the first, second, third, and fourth temperature ranges, a magnitude of a magnetic field generated by the fourth type of MNP is greater than or equal to a fourth threshold;
setting the temperature within the at least one fluidic channel to be within the fourth temperature range;
obtaining a fourth output from the selected one of the plurality of magnetic sensors while the temperature of the at least one fluidic channel is within the fourth temperature range, the fourth output indicating a magnitude of a fourth detected magnetic field; and
determining, based at least in part on the magnitude of the fourth detected magnetic field, whether the fourth type of MNP has been detected by the selected one of the plurality of magnetic sensors.

19. The method of claim 18, wherein determining, based at least in part on the magnitude of the fourth detected magnetic field, whether the fourth type of MNP has been detected by the selected one of the plurality of magnetic sensors comprises:
in response to the magnitude of the first detected magnetic field being greater than or equal to the fourth threshold, and the magnitude of the second detected magnetic field being greater than or equal to the fourth threshold, and the magnitude of the third detected magnetic field being greater than or equal to the fourth threshold, and the magnitude of the fourth detected magnetic field being greater than or equal to the fourth threshold, determining that the fourth type of MNP has been detected by the selected one of the plurality of magnetic sensors.

20. The method of claim 18, wherein two or more of the first, second, third, and fourth thresholds are different.

21. The method of claim 18, wherein the first, second, third, and fourth pluralities of molecules to be detected are added to the at least one fluidic channel at a substantially same time.

22. The method of claim 18, wherein the first characteristic temperature is a first Curie temperature, the second characteristic temperature is a second Curie temperature, the third characteristic temperature is a third Curie temperature, and the fourth characteristic temperature is a fourth Curie temperature.

23. The method of claim 22, further comprising:
before adding, to the at least one fluidic channel, the first, second, third, and fourth pluralities of molecules to be detected, setting the temperature within the at least one fluidic channel to a temperature value higher than all of the first Curie temperature, the second Curie temperature, the third Curie temperature, and the fourth Curie temperature,
and wherein adding, to the at least one fluidic channel, the first, second, third, and fourth pluralities of molecules to be detected occurs while the temperature within the at least one fluidic channel is at the temperature value higher than all of the first Curie temperature, the second Curie temperature, the third Curie temperature, and the fourth Curie temperature.

24. The method of claim 18, wherein the first characteristic temperature is a first blocking temperature, the second characteristic temperature is a second blocking temperature, the third characteristic temperature is a third blocking temperature, and the fourth characteristic temperature is a fourth blocking temperature.

25. The method of claim 11, wherein:
the magnitude of the magnetic field generated by the first type of MNP is less than the first threshold in a fourth temperature range, the fourth temperature range being higher than the third temperature range and higher than the third characteristic temperature,
the magnitude of the magnetic field generated by the second type of MNP is less than the second threshold in the fourth temperature range, and
the magnitude of the magnetic field generated by the third type of MNP is less than the third threshold in the fourth temperature range,
and further comprising:
adding, to the at least one fluidic channel, a fourth, unlabeled plurality of molecules to be detected;
setting the temperature within the at least one fluidic channel to be within the fourth temperature range;
obtaining a fourth output from the selected one of the plurality of magnetic sensors while the temperature of the at least one fluidic channel is within the fourth temperature range, the fourth output indicating a magnitude of a fourth detected magnetic field; and
in response to the magnitude of the fourth detected magnetic field being less than the first threshold, less than the second threshold, and less than the third threshold, determining that none of the first, second, or third type of MNP has been detected by the selected one of the plurality of magnetic sensors.

26. The method of claim 11, wherein:
the magnitude of the magnetic field generated by the first type of MNP is less than the first threshold in a fourth temperature range, the fourth temperature range being higher than the third temperature range and higher than the third characteristic temperature,
the magnitude of the magnetic field generated by the second type of MNP is less than the second threshold in the fourth temperature range, and
the magnitude of the magnetic field generated by the third type of MNP is less than the third threshold in the fourth temperature range,
and further comprising:
adding, to the at least one fluidic channel, a fourth, unlabeled plurality of molecules to be detected;
setting the temperature within the at least one fluidic channel to be within the fourth temperature range;
obtaining a fourth output from the selected one of the plurality of magnetic sensors while the temperature of the at least one fluidic channel is within the fourth temperature range, the fourth output indicating a magnitude of a fourth detected magnetic field; and
in response to the magnitude of the fourth detected magnetic field being less than the first threshold, less than the second threshold, and less than the third threshold, determining that at least one of the fourth, unlabeled plurality of molecules has been detected by the selected one of the plurality of magnetic sensors.

\* \* \* \* \*